United States Patent
Mohr

(10) Patent No.: US 10,967,015 B2
(45) Date of Patent: Apr. 6, 2021

(54) METHOD OF TREATMENT USING ONCOLYTIC VIRUSES

(71) Applicant: New York University, New York, NY (US)

(72) Inventor: Ian J Mohr, New York, NY (US)

(73) Assignee: New York University, New York, NY (US)

( * ) Notice: Subject to any disclaimer, the term of this patent is extended or adjusted under 35 U.S.C. 154(b) by 51 days.

(21) Appl. No.: 15/735,845

(22) PCT Filed: Jun. 15, 2016

(86) PCT No.: PCT/US2016/037712
§ 371 (c)(1),
(2) Date: Dec. 12, 2017

(87) PCT Pub. No.: WO2016/205429
PCT Pub. Date: Dec. 22, 2016

(65) Prior Publication Data
US 2018/0318366 A1    Nov. 8, 2018

Related U.S. Application Data

(60) Provisional application No. 62/175,797, filed on Jun. 15, 2015.

(51) Int. Cl.
| | | |
|---|---|---|
| *A61K 39/275* | (2006.01) | |
| *C12N 7/00* | (2006.01) | |
| *A61K 35/768* | (2015.01) | |
| *C07K 14/005* | (2006.01) | |
| *A61K 38/19* | (2006.01) | |

(52) U.S. Cl.
CPC ............ *A61K 35/768* (2013.01); *A61K 38/19* (2013.01); *C07K 14/005* (2013.01); *C12N 7/00* (2013.01); *C12N 2710/24021* (2013.01); *C12N 2710/24122* (2013.01); *C12N 2710/24132* (2013.01);
(Continued)

(58) Field of Classification Search
None
See application file for complete search history.

(56) References Cited

U.S. PATENT DOCUMENTS

| | | | |
|---|---|---|---|
| 4,814,470 A | 3/1989 | Colin et al. | |
| 4,818,694 A | 4/1989 | Watson et al. | |

(Continued)

FOREIGN PATENT DOCUMENTS

| | | |
|---|---|---|
| CA | 2381056 | 2/2001 |
| EP | 253738 | 1/1990 |

(Continued)

OTHER PUBLICATIONS

ATCC, "Vaccinia Virus (ATCC® VR-1354TM)", found on the Internet at https://www.atcc.org/en/Products/All/VR-1354.aspx, (Year: 2020).*

(Continued)

*Primary Examiner* — M Franco G Salvoza
(74) *Attorney, Agent, or Firm* — Fish & Richardson P.C.

(57) ABSTRACT

A method for treating a tumor by administering to a subject in need of such treatment an effective amount for treating the tumor of a Poxviridae decapping deficient mutant virus. Also disclosed are mutant Poxviridae and pharmaceutical formulations for use in the method.

19 Claims, 17 Drawing Sheets

Specification includes a Sequence Listing.

(52) U.S. Cl.
CPC .............. *C12N 2710/24221* (2013.01); *C12N 2710/24222* (2013.01)

(56) References Cited

U.S. PATENT DOCUMENTS

| | | | |
|---|---|---|---|
| 4,857,653 | A | 8/1989 | Colin et al. |
| 4,924,011 | A | 5/1990 | Denis et al. |
| 5,071,743 | A | 12/1991 | Slilaty et al. |
| 5,290,957 | A | 3/1994 | Correa et al. |
| 5,292,921 | A | 3/1994 | Correa et al. |
| 5,438,072 | A | 8/1995 | Bobee et al. |
| 5,554,601 | A | 9/1996 | Simpkins et al. |
| 5,587,493 | A | 12/1996 | Bouchard et al. |
| 5,702,931 | A | 12/1997 | Andrews et al. |
| 5,780,270 | A | 7/1998 | Lesley |
| 5,789,166 | A | 8/1998 | Bauer et al. |
| 5,824,318 | A | 10/1998 | Mohr et al. |
| 5,932,419 | A | 8/1999 | Bauer et al. |
| 6,242,222 | B1 | 6/2001 | Gifford |
| 7,208,313 | B2 | 4/2007 | McCart et al. |
| 7,553,483 | B2* | 6/2009 | Proudfoot ............ C07K 14/523 424/185.1 |
| 7,731,952 | B2 | 6/2010 | Mohr et al. |
| 7,981,669 | B2 | 7/2011 | Coffin et al. |
| 8,252,277 | B2 | 8/2012 | Mohr et al. |
| 8,709,397 | B2 | 4/2014 | Mohr et al. |
| 2005/0129700 | A1* | 6/2005 | Rosengard ............ C07H 21/04 424/159.1 |
| 2006/0039894 | A1 | 2/2006 | Mohr et al. |
| 2007/0264282 | A1 | 11/2007 | Coffin |
| 2009/0053178 | A1 | 2/2009 | Rabkin et al. |
| 2009/0220460 | A1 | 9/2009 | Coffin |
| 2010/0092435 | A1 | 4/2010 | Wiertz et al. |
| 2010/0151492 | A1* | 6/2010 | Ahmed ............... A61K 31/7105 435/7.2 |
| 2011/0070262 | A1 | 3/2011 | Johnson et al. |
| 2011/0236415 | A1 | 9/2011 | Mohr et al. |
| 2012/0276053 | A1 | 11/2012 | Kirn |
| 2012/0308484 | A1* | 12/2012 | Szalay ..................... C12N 7/00 424/9.3 |
| 2013/0034586 | A1 | 2/2013 | Mohr et al. |

FOREIGN PATENT DOCUMENTS

| | | |
|---|---|---|
| WO | WO 1991/17976 | 11/1991 |
| WO | WO 1993/00928 | 1/1993 |
| WO | WO 1993/00929 | 1/1993 |
| WO | WO 1996/01815 | 1/1996 |
| WO | WO 00/75292 | 12/2000 |
| WO | WO 02/076216 | 10/2002 |
| WO | WO 2005/011715 | 2/2005 |
| WO | WO 2006/002394 | 1/2006 |
| WO | WO 2013/038066 | 3/2013 |

OTHER PUBLICATIONS

Sharon et al., "Immune checkpoint inhibitors in clinical trials,", Chin J Cancer 33(9): 434-44 (Year: 2014).*
Bengali et al., "Vaccinia virus strain differences in cell attachment and entry," Virology 389(1-2): 132-140 (Year: 2009).*
Extended European Search report in Application No. 16812381.8, dated Nov. 29, 2018, 7 pages.
Guse et al., "Oncolytic vaccinia virus for the treatment of cancer," Expert Opinion on Biological Therapy, May 2011, 11: 595-608.
Liu et al., "Poxvirus decapping enzymes enhance virulence by preventing the accumulation of dsRNA and the induction of innate antiviral responses," Cell host & microbe 17.3 (Mar. 11, 2015):320-331. Entire document, especially summary, p. 321, p. 327, p. 328.
Silverman, "Caps off to poxviruses," Cell host & microbe 17.3 (Mar. 2015):287-289, entire document.
International Search Report and Written Opinion of ISA/US for PCT/US2016/037712 (dated Nov. 16, 2016).
Afonso et al., "Genome of crocodilepox virus", J. Virol., vol. 80 No. 10, 4978-4991, 2006.
Aloni et al., "Symmetrical in vivo transcription of polyoma DNA and the separation of self-complementary viral and cell RNA", Virology 54, 495-505, 1973.
Aloni, Y., "Extensive Symmetrical Transcription of Simian Virus 40 DNA in Virus-Yielding Cells", Proc. Natl. Acad. Sci. USA, 69, 2404-2409, 1972.
Arribas-Layton et al., "Structural and functional control of the eukaryotic mRNA decapping machinery.", Biochim Biophys Acta 1829, 580-589, 2013.
Baez et al., "Complete nucleotide sequence of the influenza A/PR/8/34 virus NS gene and comparison with the NS genes of the A/Udorn/72 and A/FPV/Rostock/34 strains", Nucleic Acids Res. 8: 5845-5858, 1980.
Beckham et al., "P Bodies, Stress Granules, and Viral Life Cycles", Cell Host Microbe 3, 206-212, 2008.
Bessman et al., "The MutT Proteins or "Nudix" Hydrolases, a Family of Versatile, Widely Distributed, "Housecleaning" Enzymes", J Biol Chem 271: 25059-25062, 1996.
Boone et al., "Intermolecular Duplexes Formed from Polyadenylylated Vaccinia Virus RNA", J. Virol., 30, 365-374, 1979.
Braun et al., "A direct interaction between DCP1 and XRN1 couples mRNA decapping to 5' exonucleolytic degradation", Nat Struct Mol Biol 19, 1324-1331, 2012.
Burgess et al., "Cellular 5'-3' mRNA Exonuclease Xrn1 Controls Double-Stranded RNA Accumulation and Anti-Viral Responses", Cell Host Microbe. 11; 17(3): 332-44, 2015.
Chang et al., "The E3L gene of vaccinia virus encodes an inhibitor of the interferon-induced, double-stranded RNA-dependent protein kinase", Proc Natl Acad Sci USA 89, 4825-4829, 1992.
Chapman et al., "The Structural Basis of Pathogenic Subgenomic Flavivirus RNA (sfRNA) Production.", Science 344, 307-310, 2014.
Chee et al., "Analysis of the Protein-Coding Content of the Sequence of Human Cytomegalovirus Strain AD169", Curr. Top. Microbiol. Immunol. 154:125-170, 1990.
Chroboczek et al., "The sequence of the genome of adenovirus type 5 and its comparison with the genome of adenovirus type 2", Virology, 186(1): 280-5, 1992.
Cohen et al., "Dcp2 Decaps m2,2,7GpppN-capped RNAs, and its activity is sequence and context dependent.", Mal Cell Biol 25: 8779-8791, 2005.
Covarrubias et al., "Coordinated Destruction of Cellular Messages in Translation Complexes by the Gammaherpesvirus Host Shutoff Factor and the Mammalian Exonuclease Xrn1", PLoS Pathog 7, e1002339, 2011.
Darby et al., "Sensitivity of Viruses to Phosphorylated 9-(2-hydroxyethoxymethyl)Guanine Revealed in TK-transformed Cells", J. Gen. Virol. 48: 451-454, 1980.
Daugherty et al., Rules of engagement: molecular insights from host-virus arms races. Annu Rev Genet 46, 677-700, 2012.
Decker et al., "A turnover pathway for both stable and unstable mRNAs in yeast: evidence for a requirement for deadenylation.", Genes Dev 7, 1632-1643, 1993.
Demaria et al., "Immune-Mediated Inhibition of Metastases after Treatment with Local Radiation and CTLA-4 Blockade in a Mouse Model of Breast Cancer", Clin. Cancer Res., 11: 728-734, 2005.
Deurholt et al., "Novel immortalized human fetal liver cell line, cBAL111, has the potential to differentiate into functional hepatocytes.", BMC Biotechnol. 9:89. doi: 10. 1186/1472-6750-9-89, 2009.
Dougherty et al., "Poliovirus-Mediated Disruption of Cytoplasmic Processing Bodies", J Virol 85, 64-75, 2011.
Dunckley et al., "The DCP2 protein is required for mRNA decapping in *Saccharomyces cerevisiae* and contains a functional MutT motif", EMBO J. 18: 5411-5422, 1999.
Elgadi et al., "The Herpes Simplex Virus vhs Protein Induces Endoribonucleolytic Cleavage of Target RNAs in Cell Extracts", J Virol 73, 7153-7164, 1999.
Everly et al., "mRNA Degradation by the Virion Host Shutoff (Vhs) Protein of Herpes Simplex Virus: Genetic and Biochemical Evidence that Vhs Is a Nuclease", J Virol 76, 8560-8571, 2002.
Gaglia et al., "A common strategy for host RNA degradation by divergent viruses", J Virol 86, 9527-9530, 2012.

(56) References Cited

OTHER PUBLICATIONS

Gaglia et al., "Viruses and the cellular RNA decay machinery", Wiley Interdiscip Rev RNA 1, 47-59, 2010.
Gallardo-Romer et al., "The pox in the North American backyard: Volepox virus pathogenesis in California mice (*Peromyscus californicus*)", PLoS One., 7(8): e43881, 2012.
Gameau et al., "The highways and byways of mRNA decay.", Nat Rev Mol Cell Biol 8, 113-126, 2007.
Gershon et al., "Poly(A) polymerase and a dissociable polyadenylation stimulatory factor encoded by vaccinia virus", Cell 66, 1269-1278, 1991.
Giantini et al., "Reovirus type 3 genome segment S4: nucleotide sequence of the gene encoding a major virion surface protein.." J Virol. Dec; 52(3):984-7, 1984.
Haralambieva et al., "High-Dimensional Gene Expression Profiling Studies in High and Low Responders to Primary Smallpox Vaccination", J Infect Dis 206, 1512-1520, 2012.
He et al., "The gamma(1)34.5 protein of herpes simplex virus 1 complexes with protein phosphatase 1alpha to dephosphorylate the alpha subunit of the eukaryotic translation initiation factor 2 and preclude the shutoff of protein synthesis by double-stranded RNA-activated protein kinase ", PNAS, 94, 843-848, 1997.
Hsieh et al., "Unusual pox lesions found in Chinese jungle mynahs (Acridotheres cristatellus).", Avian Pathol., 34(5):415-7, 2005.
Jacobs et al., "When two strands are better than one: the mediators and modulators of the cellular responses to double-stranded RNA", Virology 219, 339-349, 1996.
Jacquemont et al., "RNA synthesis in cells infected with herpes simplex virus. X. Properties of viral symmetric transcripts and of double-stranded RNA prepared from them", J Virol 15, 707-713, 1975.
Jagger et al., "An Overlapping Protein-Coding Region in Influenza A Virus Segment 3 Modulates the Host Response" Science 337, 199-204, 2012.
Jinek et al., "Coupled 5' Nucleotide Recognition and Processivity in Xrn1-Mediated mRNA Decay", Mol Cell 41, 600-608, 2011.
Jonas et al., "The role of disordered protein regions in the assembly of decapping complexes and RNP granules.", Genes Dev 27, 2628-2641, 2013.
Kamitani et al., "Severe acute respiratory syndrome coronavirus nsp1 protein suppresses host gene expression by promoting host mRNA degradation", Proc Natl Acad Sci USA 103, 12885-12890, 2006.
Katsafanas et al., "Colocalization of Transcription and Translation within Cytoplasmic Poxvirus Factories Coordinates Viral Expression and Subjugates Host Functions", Cell Host Microbe 2, 221-228, 2007.
Kim, "Replicating poxviruses for human cancer therapy", Journal of Microbiology, 53: 209-218, 2015.
Koonin EV., "A highly conserved sequence motif defining the family of MutT-related proteins from eubacteria, eukaryotes and viruses.", Nucleic Acids Res 21:4847, 1993.
Kwong et al., "Herpes simplex virus-infected cells contain a function(s) that destabilizes both host and viral mRNAs", Proc Natl Acad Sci USA 84, 1926-1930, 1987.
Laidlaw et al., "Comparison of the genome sequence of FP9, an attenuated, tissue culture-adapted European strain of Fowlpox virus, with those of virulent American and European viruses", J Gen. Viral. 85:305-322, 2004.
Langer, "New methods of drug delivery", Science 249:1527-1533, 1990.
Li et al., "Dcp2 decapping protein modulates mRNA stability of the critical intereferon response factor, IRF-7", Mol Cell Biol 32, 1164-1172, 2012.
Liu et al., "The D10 Decapping Enzyme of Vaccinia Virus Contributes to Decay of Cellular and Viral mRNAs and to Virulence in Mice", J Virol 88, 202-211, 2014.
Lucas et al., "Identification of double-stranded virus-specific ribonucleic acid in KB cells infected with type 2 adenovirus.", Biochem Biophys Res Commun 49, 39-44, 1972.

Manarolla et al., "Molecular biological characterization of avian poxvirus strains isolated from different avian species.", Veterinary Microbiology vol. 140, Issues 1-2, Jan. 6, 2010, pp. 1-8.
Maran et al., "Characterization of the double-stranded RNA implicated in the inhibition of protein synthesis in cells infected with a mutant adenovirus defective for VA RNA", Virology 164, 106-113, 1988.
McGeoch et al., "Sequence determination and genetic content of the short unique region in the genome of herpes simplex virus type 1", Journal of Molecular Biology 181,1-13, 1985.
Mohr et al., "A herpesvirus genetic element which affects translation in the absence of the viral GADD34 function", 2; 15(17): 4759-66, 1996.
Mohr et al., "Host Translation at the Nexus of Infection and Immunity ", Cell Host Microbe 12, 470-483, 2012.
Mohr, "To replicate or not to replicate: achieving selective oncolytic virus replication in cancer cells through translational control", Oncogene 24(52): 7697-709, 2005.
Morgan et al., "Identification of the DNA sequences encoding the large subunit of the mRNA-capping enzyme of vaccinia virus.", J Virol 52, 206-214, 1984.
Moss et al., "Characterization of a Polyriboadenylate Polymerase from Vaccinia Virions.", J Biol Chem 250, 4722-4729, 1975.
Moss, "Poxvirus DNA replication.", Cold Spring Harb Perspect Biol 5, 2013.
Mulvey et al., "A Herpesvirus Ribosome-Associated, RNA-Binding Protein Confers a Growth Advantage upon Mutants Deficient in a GADD34-Related Function", J Virol.73(4): 3375-85, 1998.
Mulvey et al., "Regulation of eIF2α Phosphorylation by Different Functions That Act during Discrete Phases in the Herpes Simplex Virus Type 1 Life Cycle", J Viral 77, 10917-10928, 2003.
Nagarajan et al., "XRN 5' -→ 3' exoribonucleases: Structure, mechanisms and functions", Biochim Biophys Acta 1829, 590-603, 2013.
Nevins et al., "Isolation and partial characterization of the poly(A) polymerases from HeLa cells infected with vaccinia virus", J Biol Chem 252, 6939-6947, 1977.
Niles et al., "Vaccinia virus gene D12L encodes the small subunit of the viral mRNA capping enzyme", Virology 172, 513-522, 1989.
Orban et al., "Decay of mRNAs targeted by RISC requires XRN1, the Ski complex, and the exosome", RNA 11, 459-469, 2005.
Panicali et al., "Construction of poxviruses as cloning vectors: insertion of the thymidine kinase gene from herpes simplex virus into the DNA of infectious vaccinia virus", Proc. Natl. Acad. Sci. USA 79: 4927-4931, 1982.
Parker et al., "The enzymes and control of eukaryotic mRNA turnover.", Nat Struct Mol Biol 11, 121-127, 2004.
Parrish et al., "Characterization of a Second Vaccinia Virus mRNA-Decapping Enzyme Conserved in Poxviruses", J Viral. 81: 12973-12978, 2007.
Parrish et al., "Characterization of a Vaccinia Virus Mutant with a Deletion of the D10R Gene Encoding a Putative Negative Regulator of Gene Expression", J Virol 80, 553-561, 2006.
Parrish et al., "Vaccinia virus D10 protein has mRNA decapping activity, providing a mechanism for control of host and viral gene expression", Proc Natl Acad Sci US A 104, 2139-2144, 2007.
Plotch et al., "A unique cap(m7GpppXm)-dependent influenza virion endonuclease cleaves capped RNAs to generate the primers that initiate viral RNA transcription.", Cell 23, 847-858, 1981.
Poole et al., "Structural Modifications of RNA Influence the 5' Exoribonucleolytic Hydrolysis by XRN1 and HKE1 of *Saccharomyces cerevisiae*", Biochem Biophys Res Commun 235, 799-805, 1997.
Read et al., "Herpes simplex virus mutants defective in the virion-associated shutoff of host polypeptide synthesis and exhibiting abnormal synthesis of alpha (immediate early) viral polypeptides", J Virol 46, 498-512, 1983.
Read, "Virus-encoded endonucleases: expected and novel functions", Wiley Interdiscip Rev RNA 4, 693-708, 2013.
Rerks-Ngarm et al., "Vaccination with ALVAC and AIDSVAX to Prevent HIV-1 Infection in Thailand ", N. Engl. J. Med. 361, 2209-2220, 2009.

(56) References Cited

OTHER PUBLICATIONS

Rivas et al., "Vaccinia virus E3L protein is an inhibitor of the interferon (i.fn.)-induced 2-5A synthetase enzyme.", Virology 243, 406-414, 1998.
Robinson et al., "Parapoxvirus of Red Deer: Evidence for Its Inclusion as a New Member in the Genus Parapoxvirus", Virology 208, 812-815, 1995.
Sadler et al., "Interferon-inducible antiviral effectors", Nat Rev Immunol 8, 559-568, 2008.
Schnitzlein et al., "Genomic and antigenic characterization of avipoxviruses," Virus Re, Apr. 1988, 10: 65-75.
Sciortino et al., "The virion host shutoff RNase plays a key role in blocking the activation of protein kinase R in cells infected with herpes simplex virus 1.", J Virol 87, 3271-3276, 2013.
Senzer et al., "Phase II clinical trial of a granulocyte-macrophage colony-stimulating factor-encoding, second-generation oncolytic herpesvirus in patients with unresectable metastatic melanoma", J Clin Oncol 27(34): 5763-5771, 2009.
Seo et al., "Protein kinase PKR mutants resistant to the poxvirus pseudosubstrate K3L protein", Proc Natl Acad Sci USA 105, 16894-16899, 2008.
Shuman et al., "Purification and characterization of a GTP-pyrophosphate exchange activity from vaccinia virions. Association of the GTP-pyrophosphate exchange activity with vaccinia mRNA guanylyltransferase . RNA (guanine-7-)methyltransferase complex (capping enzyme)." J Biol Chem 255, 11588-11598, 1980.
Silva et al., "An RNA Pseudoknot Is Required for Production of Yellow Fever Virus Subgenomic RNA by the Host Nuclease XRN1", J Virol 84, 11395-11406, 2010.
Sivan et al., "Human genome-wide RNAi screen reveals a role for nuclear pore proteins in poxvirus morphogenesis", Proc Natl Acad Sci USA 110, 3519-3524, 2013.
Stoecklin et al., "ARE-mRNA degradation requires the 5'-3' decay pathway", EMBO Rep 7, 72-77, 2006.
Taneja et al., "Enhanced antitumor efficacy of a herpes simplex virus mutant isolated by genetic selection in cancer cells", Proc Natl Acad Sci USA, 98(15):8804-8, 2001.
Treat et al., "Liposomal Encapsulated Doxorubicin—Its Role in Cancer Chemotherapy," in Liposomes in the Therapy of Infectious Disease and Cancer, Lopez-Berestein and Fidler, New York, Feb. 1988, p. 257.
Tulman et al., "Genome of lumpy skin disease virus", J. Virol. vol. 75 No. 15 7122-7130, 2001.
Tulman et al., "The Genomes of Sheeppox and Goatpox Viruses", J Virol., 76(12): 6054-6061, 2002.
Van Dijk et al., "Human Dcp2: a catalytically active mRNA decapping enzyme located in specific cytoplasmic structures", EMBO J 21: 6915-6924, 2002.
Venkatesan et al., "Modification of the 5' end of mRNA", J Biol Chem 255, 903-908, 1980.
Walsh et al., "Eukaryotic Translation Initiation Factor 4F Architectural Alterations Accompany Translation Initiation Factor Redistribution in Poxvirus-Infected Cells", Apr.; 28(8): 2648-58, 2008.
Walsh et al., "Phosphorylation of eIF4E by Mnk-1 enhances HSV-1 translation and replication in quiescent cells", Mar. 15; 18(6): 660-72, 2004.
Walsh et al., "Tinkering with Translation: Protein Synthesis in Virus-Infected Cells", Cold Spring Harb Perspect Biol 5, a012351, 2013.
Walsh et al., "Viral subversion of the host protein synthesis machinery", Nat Rev Microbiol 9, 860-875, 2011.
Wang et al., "The hDcp2 protein is a mammalian mRNA decapping enzyme", Proc Natl Acad Sci USA 99: 12663-12668, 2002.
Warren et al., "Reverse Genetic Analysis of Poxvirus Intermediate Transcription Factors", J Virol 86, 9514-9519, 2012.
Weber et al., "Double-Stranded RNA is Produced by Positive-Strand RNA Viruses and DNA Viruses but Not in Detectable Amounts by Negative-Strand RNA Viruses", J Virol 80, 5059-5064, 2006.
Winterfield et al., "Avian Pox: Infection and Immunity with Quail, Psittacine, Fowl, and Pigeon Pox Viruses", Poultry Science 64:65-70, 1985.
Aghi & Martuza, "Oncolytic Viral Therapies—The Clinical Experience," Oncogene, 2005, 24:7802-7816.
Altschul et al., "Basic Local Alignment Search Tool," J. Mol. Biol, 1990, 215: 403.
Altschul et al., "Gapped BLAST and PSI-BLAST: a new generation of protein database search programs," Nucleic Acids Res, 1997, 25:3389.
Andag and Schutz, "General Method for Site-Directed Mutagenesis," Biotech, 2001, 30: 486-488.
Barettino et al., "Improved Method for PCR-mediated Site-Directed Mutagenesis," Nuc. Acids. Res, 1993, 22: 541-542.
Benencia et al., "Herpes Vims Oncolytic Therapy Reduces Tumor Immune Dysfunction and Facilitates Tumor Antigen Presentation," Cancer Biology & Therapy, 2008, 7: 1194-205.
Boles and Miogsa, "A Rapid and Highly Efficient Method for PCR-based Site-Directed Mutagenesis Using Only One New Primer," Curr. Genet, 1995, 28: 197-198.
Bruggeman et al., "Bmil Controls Tumor Development . . . ," Cancer Cell; 2007, 12(4):328-341.
Chahlavi et al., "Effect of prior exposure to herpes simplex vims 1 on viral vector-mediated tumor therapy in immunocompetent mice," Gene Ther, 1999, 6: 17 51-8.
Chalikonda et al., "Oncolytic virotherapy for ovarian carcinonlatosis using a replication-selective vaccinia virus armed with a yeast cytosine deaininase gene," Cancer Gene Thcr, 2008, 15:115-25.
Chou et al., "Association of a Mr 90,000 phosphoprotein with protein kinase PKR in cells exhibiting enhanced phosphorylation of translation initiation factor eIF-2 alpha and premature shutoff of protein synthesis after infection with y134.5- mutants of herpes simplex virus 1," Proc. Natl. Acad. Sci. USA, 1995, 92:10516-10520.
Chou et. al., "Mapping of herpes simplex virus-1 neurovirulence to gamma 134.5, a gene nonessential for growth in culture," Science, 1990, 250: 1262-1266.
Fukuoka et al., "LifJBnd Bindin9 Sites on Guinea Pig C3aR: Point and Deletion Mutations in the Large Extracellular Loop and Vicinity," Biochem. Biophys. Res. Commun, 1999, 263: 357-360.
GenBank Accession No. X14112, "Human herpesvirus 1 complete genome," Jun. 1992, 55 pages.
Goldsmith et al., "Infected Cell Protein (ICP)47 Enhances Herpes Simplex Virus Neurovirulence by Blocking the CD8+ T Cell Response" J. Exp. Med, 1998, 187:341-348.
Gossen et al., "Transcriptional activation by tetracyclines in mammalian cells," Science, 1995, 268:1766-1769.
Gossen et al., Tight control of gene expression in mammalian cells by tetracycline-responsive promoters, Proc. Natl. Acad. Sci. USA, 89: 5547-5551, 1992.
Gruffat et al., "Herpesvirus Late Gene Expression: A Viral-Specific Pre-initiation Complex Is Key," Frontiers in Microbiology, Jun. 2016, vol. 7, Article 869, 15 pages.
Hansen et al., "Evasion of CD8+ T Cells is Critical for Superinfection by Cytomegalovirus," Science, 2010, 328: 102-106.
He et al., "The γ134.5 protein of herpes simplex virus 1 complexes with protein phosphatase 1α to dephosphorylate the α subunit of the eukaryotic translation initiation factor 2 and preclude the shutoff of protein synthesis by double-stranded RNA-activated protein kinase," Proc. Natl. Acad. Sci. USA, 1997, 94:843-848.
Hellums et al., "Increased efficacy of an interleukin-12-secreting herpes simplex virus in a syngeneic intracranial murine glioma model," Neuro-oncology, 2005, 7:213-24.
Hogrefe, "Mutagenesis: An Important Tool for Proteomics," Strategies, 2001, 143: 74-75.
Honess et al., "Regulation ofHerpesvims Macromolecular Synthesis I. Cascade Regulation of the Synthesis of Three Groups of Viral Proleins1", Journal of Virology, Jul. 1974, vol. 14, No. 1, pp. 8-19.
Hung et al. "Vaccinia virus preferentially infects and controls human and murine ovarian tumors in mice," Gene Ther, 2007;14:20-9.
International Search Report and Written Opinion for PCT/US2012/054206 dated Jan. 28, 2013. 16 pages.

(56) References Cited

OTHER PUBLICATIONS

Kang et al., "Rapid PCR Method for Site-Directed Mutagenesis on Double-Stranded Plasmid DNA," Biotech, 1996, 20: 44-46.
Karlin and Altschul, "Methods for assessing the statistical significance of molecular sequence features by using general scoring schemes," PNAS, 1990, 87:2264-2268.
Karlin and Altschul, "Applications and statistics for multiple high-scoring segments in molecular sequences," PNAS, 1993, 90:5873-5877.
Kavanagh et al., "The Multiple Immune-evasion Genes ofMurine Cytomegalovims are Not Redundant:m4 and m152 Inhibit Antigen Presentation in a Complementary and Cooperative Fashion," JExp. Med, 2001, 194(7):967-78.
Kim and Maas, "Multiple Site Mutagenesis with High Targeting Efficiency in One Cloning Step," BioTech, 2000, 28: 196-198.
Kirsch and Joly, "An improved PCR-mutagenesis strategy for two-site mutagenesis or sequence swapping between related genes," Nuc. Acids. Res, 1998, 26: 1848-1850.
Koppers-Lalic et al., "Varicellovims UL49.5 Proteins Differentially Affect the Function of the Transporter . . . ," PLoS, 2008, 4(5): e1000080.
Kunkel, "Rapid and Efficient Site-specific Mutagenesis Without Phenotypic Selection," Proc. Natl. Acad. Sci. USA, 1985, 82: 488-492.
Lipinska et al., "Bovine Herpesvims 1 UL49.5 Protein Inhibits the Transporter Associated with Antigen Processing despite Complex Formation with Glycoprotein M," J Virol, 2006, 80:5822-32.
Liu et al. "ICP34.5 deleted herpes simplex virus with enhanced oncolytic, immune stimulating, and anti-tumour properties", Gene Therapy, 2003, vol. 10, pp. 292-303.
Lopez-Berestein, "Treatment of Systemic Fungal Infections With Liposomal-Amphotericin B," Liposomes in the Therapy of Infectious Disease and Cancer 1989, pp. 317-327.
Markert et al., "Preclinical Evaluation of a Genetically Engineered Herpes Simplex Vims Expressing Interleukin-12," J. Virol., 2012; 86:5304-13.
Marumoto et al., "Development of a Novel Mouse Glioma Model Using Lentiviral Vectors," Nat Med, 2009, 15(1):110-6.
Meignier et al., "In vivo behaviour of genetically engineered heipes simplex viruses R 7017 and R7020: construction and evaluation in rodents," J. Infect. Dis., 1988, 158(3): 602-614.
Rehm et al., "Membrane Topology of the Outer Membrane Protein OprH from Pseudomonas aemginosa: PCRMediated Site-Directed Insertion and Deletion Mutagenesis," Journal of Bacteriology, 1996, 3346-3349.
Mohr et al. "A Herpes Simplex Virus Type 1 y34.5 Second-Site Suppressor Mutant That Exhibits Enhanced Growth in Cultured Glioblastoma Cells is Severely Attenuated in Animals", Journal of Virology, Jun. 2001, pp. 5189-5196.
Needleman and Wunsch, "A General Method Applicable to the Search for Similarities in the Amino Acid Sequence of Two Proteins," J. Mol. Biol, 1970, 48:444-453.
Office Action which dated Apr. 9, 2015 in corresponding European counterpart application No. 12830105.8.
Ogel and McPherson, "Efficient Deletion Mutagenesis by PCR," Protein Engineer, 1992, 5: 467-468.
Oosten et al. "TAP-inhibiting proteins US6, ICP47 and UL49.5 differentially affect minor and major histocompatibility antigen-specific recognition by cytotoxic T lymphocytes", International Immunology, 2007, vol. 19, No. 9, pp. 1115-1122.

Parikh and Guengerich, "Random Mutagenesis by Whole-Plasmid PCR Amplification," Bio Tech, 1998, 24: 428-431.
Pons et al., "PCR Site-Directed Mutagenesls Using Pyrococcus sp GB-D Polymerase Coupled to a Rapid Screening Procedure," Meth. Molec. Biol, 1997, 67: 209-218.
Ray and Nickoloff, "Site-Specific Mutagenesis of Almost Any Plasmid Using a PCR-Based Version of Unique Site Elimination," Bio Tech, 1992. 13: 342-346.
Rhem and Hancock, "Membrane Topology of the Outer Membrane Protein OprH from Pseudomonas aeruginosa: PCR-Mediated Site-Directed Insertion and Deletion Mutagenesis," J. Bacteriol, 1996, 178: 3346-3349.
Simpson et al., "Combination of a Fusogenic Glycoprotein, Prodmg Activation, and Oncolytic Herpes Simplex Vims for Enhanced Local Tumor Control," Cancer Res, 2006, 66:9: 4835-4842.
Spector et al. "Mutational analysis of the promoter region of the a27 gene of herpes simplex virus 1 within the context of the viral genome," Proc. Natl. Acad. Sci. USA, Jul. 1990, vol. 87, pp. 5268-5272.
Taneja et. al., "Enhanced antitumor efficacy of a herpes simplex virus mutant isolated by genetic selection in cancer cells," Proc. Natl. Acad. Sci. USA, 2001, 98:8804-8808.
Tessier and Thomas, "PCR-Assisted Mutagenesis for Site-Directed Insertion/Deletion of Large DNA Segments," Meths. Molec. Biol, 1996, 57: 229-237.
Thompson et al., "DNA sequence and RNA transcription through a site of recombination in a nonneurovimlent herpes simplex vims intertypic recombinant," Vims Genes, 1998, 1(3): 275-286.
Toda et al. "Herpes simplex vims as an in situ cancer vaccine for the induction of specific antitumor immunity." Hum Gene Ther, 1999, 10:385-93.
Todo et al., "Systemic Antitumor Immunity in Experimental Brain Tumor Therapy Using a Multimutated, Replication-Competent Herpes Simplex Vims," Hum Gene Ther, 1999, 10:2741-55.
Todo et al., "Oncolytic herpes simplex virus vector with enhanced MHC class I presentation and tumor cell killing," Proc Natl Acad Sci U SA, 2001, 98(11 ):6396-401.
Todo, "Oncolytic virus therapy using genetically engineered herpes simplex viruses," Front Biosci, 2008, 13:2060-4.
Treat et al., Liposome Encapsulated Doxobubicin Preliminary Results of Phase I and II Trials, in Liposomes in the Therapy of Infectious Disease and Cancer, Lopez-Berestein and Fidler (eds.), Liss: New York, pp. 353-365 (1989).
Van Hall et al., The Varicellovims-Encoded TAP Inhibitor UL49.5 Regulates the Presentation of CTL Epitopes by Qa-lbl, J. Immunology (2007) 178:657-662.
Verweij et al., "Structural and functional analysis of the TAP-inhibiting UL49.5 proteins of varicellovimses," Mol. Immunol., 2011, 48: 2038-2051.
Wang and Malcolm, "Two-Stage PCR Protocol Allowing Introduction of Multiple Mutations, Deletions and Insertions Using . . . ," BioTech, 1999, 26: 680-682.
Wang and Wilkinson, "Site-Directed Mutagenesis of Large (13-kb) Plasmids in a Single-PCR Procedure," Biotech, 2000, 29: 976-978.
Wang et al., Multiple Mutant cDNAs from One Reaction Mixture Using Asymmetric Primers in PC, BioTech. 19: 556-559 (1995).
Xu and Gong, "Adaptation of Inverse PCR to Generate an Internal Deletion," BioTech, 1999,. 26:639-641.
Zamarin et al., "Genetically engineered Newcastle disease vims for malignant melanoma therapy," Gene Ther, 2009, 16:796-804.

* cited by examiner

METHOD OF TREATMENT USING ONCOLYTIC VIRUSES

This invention was made with government support under Grant Nos. AI073898 and GM056927 awarded by the National Institutes of Health. The government has certain rights in the invention.

CROSS REFERENCE TO RELATED APPLICATIONS

This application is a non-provisional application of U.S. Provisional Application No. 62/175,797 filed Jun. 15, 2015, which is incorporated herein by reference in its entirety.

FIELD OF THE INVENTION

The present invention pertains to methods of treatment using oncolytic viruses and more particularly to methods of treating tumors in mammals using decapping deficient mutant virus strains. Pharmaceutical formulations containing oncolytic viruses are also disclosed.

BACKGROUND OF THE INVENTION

Emergent biological therapies may command tremendous advantages over traditional cancer chemotherapy and radiation, whose efficacies are restricted by toxicity and resistance. Besides reduced toxicity and greater selectivity for tumor cells, new therapies reliant on multiple methods of cell killing distinct from conventional antineoplastic agents and capable of eliciting systemic anti-tumor immune responses promise durable cures and overall survival benefits. Capitalizing on their inherent ability to invade cells, reprogram them to produce infectious progeny, and spread, viruses can be tailored to selectively destroy tumor cells by modifying their genomes. The resulting engineered viruses are attenuated due to deletion of key virulence genes, yet retain the ability to replicate productively in and destroy cancer cells. Such variants, which do not cause disease but are selectively virulent in tumors are termed oncolytic viruses (OVs). Tumor destruction driven, in part, by active viral replication within cancer cells is referred to herein as viral oncolysis. In addition to direct oncolytic action, OVs stimulate systemic, anti-tumor immune responses and are likewise potent immuno-therapeutic agents on their own and in conjunction with immune checkpoint blockade immunotherapy (Zamarin et al., 2014; Zamarin & Wolchok, 2014).

To thwart production of host defense molecules and stimulate viral mRNA translation, viruses often subvert cellular mRNA decay pathways and manipulate Xrn1 (Gaglia and Glaunsinger, 2010; Read, 2013). While some RNA viruses circumvent Xrn1 action to preserve their genomic integrity (Chapman et al., 2014; Dougherty et al., 2011; Silva et al., 2010), others that produce $m^7GTP$-capped mRNAs harness the mRNA exonucleolytic powers of Xrn1 to accelerate host and viral mRNA decay (Gaglia et al., 2012). Besides restricting host protein synthetic capabilities by reducing mRNA abundance, accelerating viral mRNA turnover sharpens transitions between different kinetic classes of temporally transcribed mRNAs and shapes the viral developmental gene expression profile (Kwong and Frenkel, 1987; Read and Frenkel, 1983). This is exemplified by mRNA endonucleases encoded by certain herpesviruses, which produce exposed 5'-monophosphate-containing RNA fragments that are degraded by Xrn1 (Covarrubias et al., 2011; Elgadi et al., 1999; Everly et al., 2002; Gaglia et al., 2012). Other viruses including influenza and coronaviruses also encode mRNA endonucleases (Jagger et al., 2012; Kamitani et al., 2006; Plotch et al., 1981); however a role for Xrn1 and the host decay machinery has only been shown for the SARS coronavirus nsp1 (Gaglia et al., 2012). In contrast, vaccinia virus (VacV) encodes two nudix domain-containing polypeptides related to the cellular Dcp2 decapping enzyme that accelerate mRNA turnover (Parrish and Moss, 2006, 2007; Parrish et al., 2007).

Decapping enzymes catalyze a reaction whereby the monomethyl guanosine cap ($m^7G$) on the 5'-termini of eukaryotic mRNA is cleaved to generate a 5'-monophosphate mRNA. Poxviridae family members encode decapping enzymes that utilize both viral and host mRNAs as substrates. The prototypical Poxviridae family member Vaccinia virus (VACV) encodes two decapping enzymes, D9 and D10, each of which contains an approximately 23 amino acid conserved motif called the nudix hydrolase motif (or alternatively referred to as the MuT motif). This nudix hydrolase or MutT motif is found in a variety of pyrophosphatases and is a signature functional motif required for decapping enzyme activity (Koonin, 1993; Bessman et al, 1996; Dunckley & Parker, 1999; Van Dijk et al., 2002; Wang et al., 2002; Cohen et al., 2005; Parrish et al., 2007). Significantly, genes orthologous to VACV D9 and/or D10 that contain a nudix hydrolase or MutT motif are found in many Poxviridae family members.

As a large DNA virus that replicates exclusively within the cytoplasm, Poxviruses like VacV encode the components required to produce capped, polyadenylated mRNAs (Moss, 2013). A virus-encoded heterodimeric cap methyltransferase (Morgan et al., 1984; Niles et al., 1989; Shuman et al., 1980; Venkatesan et al., 1980) and a poly (A) polymerase (Gershon et al., 1991; Moss et al., 1975; Nevins and Joklik, 1977) effectively mark nascent mRNAs with structural features vital for their stability and capacity to be translated. These mRNAs accumulate in discrete subcellular replication compartments together with select host proteins, including translation initiation factors (Katsafanas and Moss, 2007; Walsh et al., 2008). Remarkably, the D9 and D10 open reading frames (ORFs) encode proteins that stimulate mRNA turnover in infected and uninfected cells and function as decapping enzymes in vitro (Parrish and Moss, 2006, 2007; Parrish et al., 2007). While D9 is expressed early in the viral lifecycle, D10 is expressed later and its expression correlates with the virus-induced suppression of host protein synthesis (Parrish and Moss, 2006). Indeed, the kinetics of host protein synthesis suppression was delayed in cells infected with a D10-deficient virus and a D10 mutant virus was attenuated for virulence in mice (Liu et al., 2014; Parrish and Moss, 2006). D10 may also regulate viral gene expression since it prefers m7GpppG over m7GpppA substrates in vitro and the latter are only found on intermediate and late genes (Parrish et al., 2007). While decapped mRNAs like those produced by D9/10 are posited targets for Xrn1, precisely how Xrn1 might impact infected cell biology has not been investigated. Disclosed herein is the discovery that Xrn1 plays an unexpected role in VacV biology, as all ongoing protein synthesis ceased in Xrn1-depleted primary human fibroblasts infected with VacV, severely restricting virus growth. This occurred prior to completion of the viral lifecycle and was exacerbated by the absence of D9 decapping enzyme. Moreover, it coincided with dsRNA accumulation and activation of host dsRNA-responsive defenses controlled by PKR, which phosphorylates and inactivates the critical translation initiation factor eIF2, and 2'-5' oligoadenylate synthetase, which stimulates rRNA cleavage by RNase L. Significantly, Xrn1-depletion even sensitized uninfected cells to dsRNA treatment. Thus, a key host mRNA decay enzyme, Xrn1, is required to regulate cytoplasmic dsRNA accumulation and signaling through critical host dsRNA-responsive innate immune sensing pathways in uninfected and VacV infected cells. As VacV, like many viruses, encodes a dsRNA binding protein to limit dsRNA accumulation and signaling, it has now been found that the host Xrn1 functionally controls dsRNA homeostasis in infected cells, despite the presence of a viral dsRNA binding protein. This challenges existing notions regarding the potency of viral dsRNA antagonists.

SUMMARY OF THE INVENTION

It has now been discovered that Poxviridae decapping deficient mutants serve as oncolytic agents for use in the treatment of tumors in mammals. As used herein, the term Poxviridae decapping deficient mutant means a Poxviridae amily member that is missing or does not encode at least one functional decapping enzyme that contains a nudix hydrolase or MutT motif.

By accelerating global mRNA decay, many viruses impair host protein synthesis to limit host defense molecule production and stimulate virus mRNA translation. For example, the prototypical Poxvirus Vaccinia (VacV) encodes two decapping enzymes (D9, D10) presumed to generate substrates degraded by the host 5'-3'-mRNA exonuclease Xrn1. Surprisingly, VacV-infection of Xrn1-depleted primary cells resulted in the inhibition of ongoing protein synthesis, severely compromising virus growth. This was aggravated by D9-deficiency and dependent upon a specific virus transcription factor required for intermediate and late mRNA biogenesis. Considerable dsRNA accumulation in Xrn1-depleted cells accompanied activation of host dsRNA-responsive defenses controlled by PKR, which inactivates the translation initiation factor eIF2, and 2'-5'-oligoadenylate synthetase, which stimulates rRNA cleavage by RNase L. Moreover, Xrn1-depletion even sensitized uninfected cells to dsRNA treatment. This identifies the mRNA decay enzyme, Xrn1, as a critical cellular factor regulating dsRNA accumulation and host dsRNA-responsive innate immune effectors in uninfected and VacV-infected cells.

It has now been discovered that the growth of Poxviridae decapping deficient mutant viruses in normal cells is impaired because these viruses, while attenuated, potently activate cellular innate anti-viral defenses (Burgess & Mohr, 2015; Liu et al, 2015), likely accounting for their reduced virulence in animals (Liu et al, 2014; 2015). In contrast, intrinsic, anti-viral defenses are impaired in numerous cancer cells and allow the growth of attenuated viruses that are unable to counteract host defenses including PKR and RNase L. While Poxviridae decapping deficient mutant viruses are attenuated in mice, they remain capable of destroying cancer cells because these tumor cells have deficiencies in many intrinsic host defenses.

In one aspect, disclosed herein is a method for treating a tumor which comprises administering to a subject in need of such treatment an effective amount for treating the tumor of a Poxviridae decapping deficient mutant virus.

In another aspect, disclosed herein is a method wherein the Poxviridae decapping deficient mutant virus is deficient in one or more genes that encode at least one polypeptide with a nudix hydrolase or MuT motif.

In another aspect, the Poxviridae decapping deficient mutant virus is a member of the sub-family chordopoxviridae.

In another aspect, the chordopoxviridae is a vaccinia virus.

In another aspect, the vaccinia virus is selected from the group consisting of D9, D10, and D9/10 doubly deficient mutants.

In another aspect, the vaccinia virus is deficient in a D9 gene or D10 gene or both.

In another aspect, the effective amount comprises between about $10^4$ pfu per kg body weight to about $3\times10^7$ pfu per kg body weight of the subject.

In another aspect, the subject is a mammal.

Also disclosed herein is a Poxviridae decapping deficient mutant virus.

Further disclosed herein is a Poxviridae decapping deficient mutant virus deficient in one or more genes that encode at least one polypeptide with a nudix hydrolase or a MuT motif.

In another aspect, the tumor is a member selected from the group consisting of cancer of the breast, brain, cervix, colon, head & neck, liver, kidney, lung, non-small cell lung, melanoma, mesothelioma, ovary, sarcoma, stomach, uterus and medulloblastoma. neuroblastoma, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

In another aspect, the Poxviridae decapping deficient mutant virus is administered in a pharmaceutical formulation.

In another aspect, the formulation is administered systemically.

In another aspect, formulation is administered parenterally.

In another aspect, said formulation is administered by direct injection into the tumor.

In another aspect, the formulation comprises a pharmaceutically acceptable carrier or diluent.

In another aspect, a checkpoint inhibitor s administered

In another aspect, the checkpoint inhibitor is co-administered with the In another aspect, the checkpoint inhibitor is administered separately from the pharmaceutical formulation.

In another aspect, the method further comprising treating said subject with an anti-cancer therapy selected from the group consisting of chemotherapy, radiation therapy, thermotherapy and TACE (transarterial chemoembolization).

In another aspect, the subject is a human.

In another aspect, the subject is an animal.

In another aspect, the vaccinia virus (VacV) is selected from the group consisting of VacV strains Western Reserve (ATCC VR-1354), NYCBofH-Wyeth (ATCC VR-1536), Modified Vaccinia Virus Ankara (ATCC VR-1566) and Lister (ATCC In another aspect, the Poxviridae decapping deficient mutant further comprise an immune stimulating cytokine selected from the group consisting of IL-1, IL-2, IL-3, IL-4, IL-5, IL-6, IL-7, IL-8, IL-9, IL-10, IL-11, IL-12, IL-13, IL-14, IL-15, IL-16, IL-17 and IL-18-IL-36.

In another aspect, said immune stimulating cytokine is selected from the group consisting of a TAP inhibitor, granulocyte macrophage colony stimulating factor (GM-CSF). In another aspect, the Poxviridae decapping deficient mutant further comprises a chemokine selected from the group consisting of CC chemokines, CXC chemokines, C chemokines, and $CX_3C$ chemokines. In another aspect, said Poxviridae decapping deficient mutant comprises a PKR/Ribonuclease L inhibitor selected from the group consisting of Herpes Simplex virus Type 1 (HSV1) Us11, human cytomegalovirus (HCMV) TRS1, reovirus sigma 3, influenza virus NS1, vaccinia virus E3L or K3L genes.

In another aspect, the Poxviridae decapping deficient mutant comprises a thymidine kinase (tk) gene.

In another aspect, the thymidine kinase (tk) gene is from Herpes Simplex virus.

In another aspect disclosed herein is a pharmaceutical formulation comprising a Poxviridae decapping deficient mutant virus and a pharmaceutically acceptable carrier or diluent.

In another aspect the pharmaceutical formulation includes an immune checkpoint inhibitor.

In another embodiment, the immune checkpoint inhibitor comprises an antibody.

In a further embodiment, the antibody is directed against a cellular protein selected from the group consisting of PD1, PDL1, CTLA4, Tim-3, BTLA, Lag-3 and Tigit.

In a further embodiment, the Poxviridae decapping deficient mutant is deficient in one or more genes which encode at least one polypeptide with a nudix hydrolase or MuT motif.

In a further embodiment the pharmaceutical formulation contains a decapping deficient mutant that is a member of the sub family chordopoxviridae.

In another embodiment, the chordopoxviridae sub-family member is a vaccinia virus (VacV).

In another embodiment the VacV is selected from the group consisting of strains Western Reserve (ATCC VR-1354), NYCBofH-Wyeth (ATCC VR-1536), Modified Vaccinia Virus Ankara (ATCC VR-1566) and Lister (ATCC VR-1549.

In a still further embodiment, the VacV further comprises an immune stimulating cytokine that is a member selected from the group consisting of IL-1, IL-2, IL-3, IL-4, IL-5, IL-6, IL-7, IL-8, IL-9, IL-10, IL-11, IL-12, IL-13, IL-14, IL-15, IL-16, IL-17 and IL-18-IL-36.

In another embodiment, the immune stimulating cytokine is a member selected from the group consisting of a TAP inhibitor, granulocyte macrophage colony stimulating factor (GM-CSF).

In yet another embodiment, the Poxviridae decapping deficient mutant further comprises a chemokine selected from the group consisting of CC chemokines, CXC chemokines, C chemokines, and $CX_3C$ chemokines.

In a still further embodiment, the Poxviridae decapping deficient mutant comprises a PKR/Ribonuclease L inhibitor selected from the group consisting of Herpes Simplex virus Type 1 (HSV1) Us11, human cytomegalovirus (HCMV) TRS1, reovirus sigma 3 and influenza virus NS1 genes.

In another embodiment disclosed herein is a method for reducing the tumor burden in a mammal by administering to a mammal in need of such treatment an effective amount for reducing the tumor burden of the mammal of a Poxviridae mutant deficient for one or more viral genes that encode decapping enzymes.

In another embodiment of the method, the Poxviridae decapping deficient mutant is deficient in one or more genes which encode at least one polypeptide with a nudix hydrolase or MuT motif.

In another embodiment of the method, the Poxviridae decapping deficient mutant is a member of the sub family chordopoxviridae.

In a still further embodiment of the method, the chordopoxviridae is a vaccinia virus.

In a still further embodiment of the method, the vaccinia virus is a member selected from the group consisting of D9, D10, and D9/10 doubly deficient mutants.

In yet another embodiment of the method, the mammal is a human.

In another embodiment of the method, the vaccinia virus is deficient in a D9 gene or D10 gene or both.

In a further embodiment the method comprises administering a pharmaceutical formulation comprising the Poxviridae decapping deficient mutant and a pharmaceutically acceptable excipient.

In a further embodiment of the method, the pharmaceutical formulation comprises an immune checkpoint inhibitor.

In a still further embodiment of the method, the immune checkpoint inhibitor comprises an antibody.

In a further embodiment the method comprises administering the immune checkpoint inhibitor separately from the pharmaceutical formulation.

These and other aspects and embodiments of the present invention will be apparent to those of ordinary skill in the art in light of the present description, claims and drawings.

The details of one or more embodiments of the invention are set forth in the accompanying drawings and the description below. Other features, objects, and advantages of the invention will be apparent from the description and drawings, and from the claims.

Figure 1:
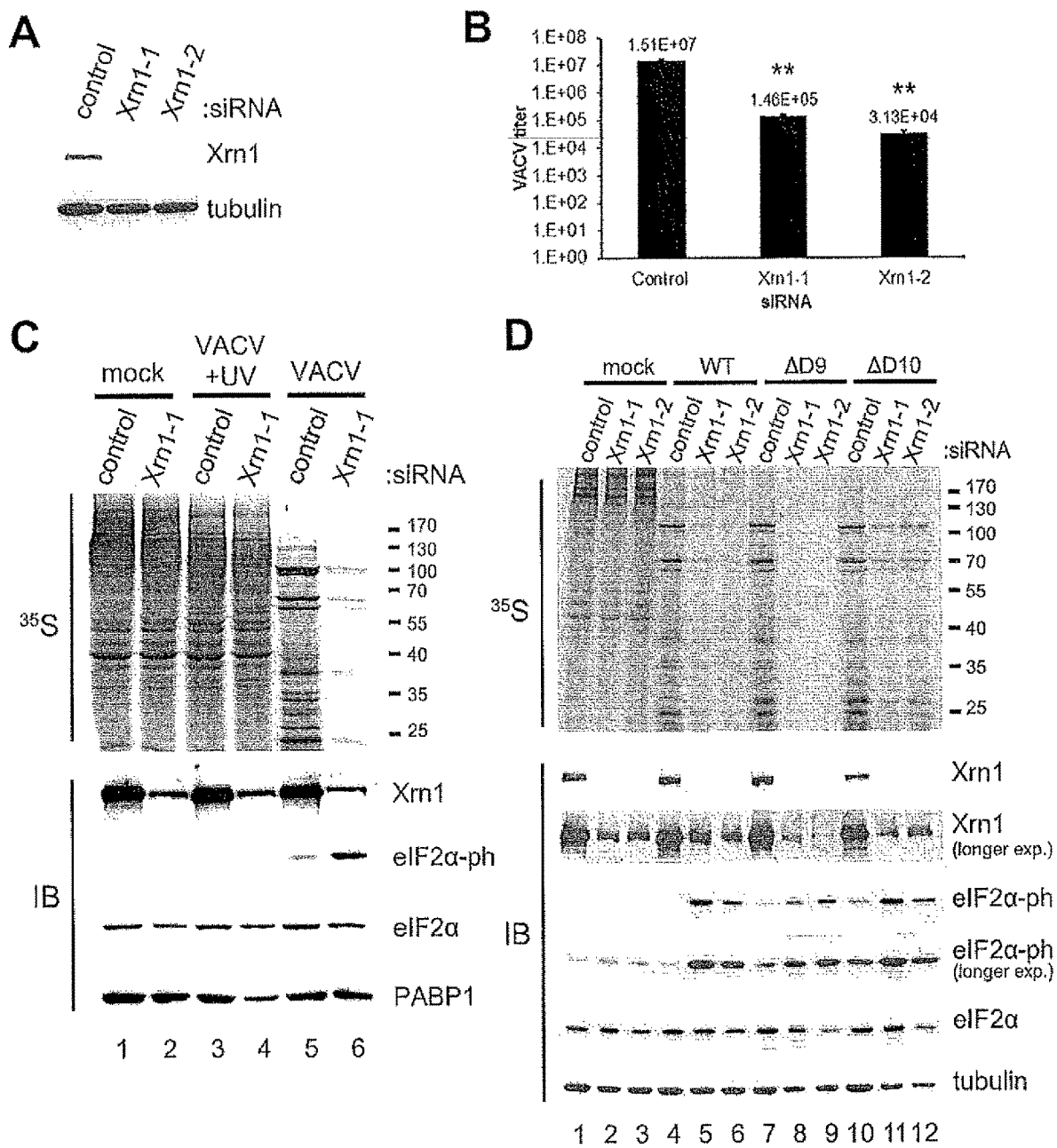
FIG. 1A-1D. Inhibition of protein synthesis and VacV replication by Xrn1-depletion. (1A) Normal human dermal fibroblasts (NHDFs) were transfected with non-silencing (ns) control or one of two Xrn1-specific siRNAs (−1 and −2). After 3 days, total protein was collected and Xrn1 levels analyzed by immmunoblotting. Tubulin served as a loading control. (1B) NHDFs treated with siRNAs as in 1A were infected with VacV (MOI=$5 \times 10^{-4}$). Infectious virus produced after 3 days was quantified by plaque assay. Means of 3 independent experiments are plotted ±SEM. ** indicates P≤0.01 by paired student's t-test compared to control siRNA-treated samples. (1C) NHDFs treated with siRNAs as in 1A were mock-infected or infected with VacV or UV-inactivated VacV (MOI=5). At 18 hours post-infection (hpi), cells were metabolically pulse-labeled with [$^{35}$S]Met-Cys for 30 min. Total protein was collected, separated by SDS-PAGE and [$^{35}$S]-labeled proteins visualized by exposing the fixed, dried gel to X-ray film. Molecular mass standards (in kDa) are shown to the right (upper panel). The same lysates were analyzed by immunoblotting (IB) with the indicated antibodies (lower panel). PABP1 served as a loading control. (1D) As in 1C except NHDFs were infected with WT VacV or D9- (ΔD9) or D10- (ΔD10) deficient VacV viruses (MOI=3). HSC70 was used as a loading control. See also FIG. 8.

Applicant hereby submits that the enclosed Sequence Listing fulfills the requirements under 37 C.F.R. § 1.821-1.825. The amendments in the specification merely insert the paper copy of the Sequence Listing and sequence identifiers in the specification. No new matter has been added.

DETAILED DESCRIPTION OF THE INVENTION

The present invention is based on the unexpected discovery that Poxviridae decapping deficient mutants can be used as oncolytic agents for treating mammals afflicted with tumors. This was unexpected because, as described below, the growth of these Poxviridae decapping deficient mutants in normal cells and their virulence in animals is impaired because this virus, while attenuated, potently activates cellular intrinsic anti-viral defenses.

Disclosed herein is the use of Poxviridae and viruses from the subgenus chordopoxviridae in particular, deficient in one or more virus-encoded decapping functions for oncolytic virus (OV) immunotherapy. While many different virus platforms are being considered for OV therapy, Poxviruses are considered the best platform for systemic, intravenous delivery of OVs because they can withstand innate defenses in serum (including complement). They are also effective following local administration and can generate systemic anti-tumor immune responses. Many Poxviruses have been made safe by removing the viral gene for thymidine kinase (tk), or ribonucleotide reductase, which restricts growth in dividing cells but also may over-attenuate the virus, crippling its capacity to destroy tumor cells and limiting its ability to induce a systemic anti-tumor immune response. Using modified Poxviridae family members, such as Vaccinia virus (VacV) strains deficient in the VacV decapping enzymes D9, D10, or both D9/D10 represents a safe, effective approach for using Poxvirus OVs that can be further modified to i) increase tumor cell killing; and ii) induce a systemic anti-tumor immune response. These D9, D10, and D9/D10 doubly-deficient derivatives can be created in a variety of standard VacV viral strains suitable for use in patients (including but not limited to Western Reserve (ATCC VR-1354), NYCBofH-Wyeth (ATCC VR-1536), Modified Vaccinia Virus Ankara (ATCC VR-1566) and Lister (ATCC VR-1549).

It has now been discovered that depleting the host mRNA decay enzyme Xrn1, a 5'-3' exoribonuclease, restricts VacV replication (Burgess & Mohr, 2015). This phenotype shows a synthetic genetic interaction with deficiencies in the virus-encoded decapping enzymes encoded by the D9 and D10 genes, consistent with their participating in the same genetic pathway (Burgess & Mohr 2015). The block to viral replication in the absence of the host enzyme Xrn1 or in the absence of virus-encoded decapping enzymes D9, D10, or a doubly-deficient D9/D10 mutant results from accumulation of double-stranded RNA (dsRNA) in infected cells, a danger signal indicative of virus infection that in turn activates host antiviral defense molecules including PKR and RNase L (Burgess & Mohr, 2015; Liu et al, 2015). By inactivating the host protein synthesis machinery, stimulation of PKR and RNase L arrests virus replication. Significantly, the growth of Poxvirus D9, D10 or D9/10 double mutants in normal cells and their virulence in animals (Liu et al, 2014; 2015) is impaired because this virus, while attenuated, potently activates cellular intrinsic anti-viral defenses (Burgess & Mohr, 2015; Liu et al, 2015). In contrast, intrinsic anti-viral defenses are impaired in numerous cancer cells and allow the growth of attenuated viruses that are unable to counteract host defenses including PKR and RNase L. Previously, it had been established that herpes simplex virus-1 (HSV-1) ICP34.5-deficient derivatives, which are defective in controlling PKR and RNase L, are useful oncolytic viruses. While HSV1 ICP34.5-deficient viruses and derivative strains remain attenuated and do not cause disease, they remain capable of destroying cancer cells because these tumor cells have deficiencies in many innate host defenses. There are no homologues of ICP34.5 in VacV or any other Poxviridae family member and the prior art did not implicate Poxviridae genes that encode decapping enzymes in controlling host defenses PKR and RNase L. In fact, this was taught against by much work demonstrating that the VacV genes E3L and K3L were critical for countering PKR activity. Without wishing to be bound by theory, it is believed that since Poxviridae decapping deficient mutants are unable to counter the antiviral host defenses in normal cells, they can preferentially replicate in many cancer cells that lack normal host defenses (including PKR, RNase L) and interferon responsiveness. Thus, attenuated decapping deficient Poxviridae family member are ideally suited for use as therapeutic oncolytic viruses.

While Poxviridae decapping deficient mutant viruses can replicate in and kill many types of cancer cells, it is conceivable that their oncolytic activity may be restricted in other types of cancer cells and that they are in effect over-attenuated. Thus, they may require further modification to kill cancer cells effectively. To achieve this, the virus is passaged multiple times through restrictive, non-permissive cancer cells, such as U373 (SKU 08061901, available from Sigma-Aldrich) or U-251 MG (SKU 09063001, available from Sigma-Aldrich) glioma cells or SKN-SH neuroblastoma cells (available from the American Type Culture Collection [ATCC, Manassas, Va.)] as HTB-11), that are known to restrict the growth of viruses unable to counter PKR and RNase L. Such viruses remain attenuated for virulence in animals but selectively kills cancer cells. The genetic alterations responsible for this phenotype can be mapped by standard methods known to those of ordinary skill in the art and the genetic changes responsible for enhanced cancer cell killing precisely defined. As described in U.S. Pat. No. 5,824,318, this method has been successfully used to enhance the oncolytic activity of HSV1 ICP34.5-deficient viruses.

In one preferred embodiment, a recombinant Vaccinia virus deficient in D9, D10, or D9/10 is engineered to express a heterologous [e.g., HSV1 Us11 (McGeoch, D. J., Dolan A., Donald, S. & Rixon, F. J., 1985), Human Cytomegalovirus (HCMV) TRS1 (Chee, M. S., A. T. Bankier, S. Beck, R. Bohni, C. M. Brown, R. Cerny, T. Horsnell, C. A. I. Hutchison, T. Kouzarides, J. A. Martignetti, E. Preddie, S. C. Satchwell, P. Tomlinson, K. M. Weston, and B. G. Barrell. 1990), reovirus sigma 3 (Giantini, M., Seliger, L. S., Furuichi, Y., Shatkin, A. J., 1984), influenza virus NS1-1 (Baez, M., Taussig, R., Zazra, J. J., Young, J. F., Palese, P., Reisfeld, A., Skalka, A. M., 1980), and adenovirus VA RNA (Chroboczek, J. 1, Bieber, F., Jacrot, B., (1992)] or a homologous inhibitor of PKR/RNase L as an early protein (Poxvirus E3L, K3L), prior to the initiation of viral DNA synthesis. By producing or overexpressing a viral antagonist of PKR/RNase L as an early protein before DNA replication commences, the D9, D10 or D9/10 doubly deficient Vaccinia virus can antagonize PKR and RNase L and more effectively kill cancer cells.

Because the Poxviridae decapping deficient mutant replicates more slowly, it remains vulnerable to clearance by the adaptive immune response that develops post-treatment. The longer the attenuated Poxvirus persists, the greater chance it will have to destroy tumor cells and stimulate a systemic, immunotherapeutic anti-tumor response. In one particularly preferred embodiment, the D9, D10, or D9/10 doubly-deficient Vaccinia virus mutant derivatives (including those modified by passage through cancer cells or those engineered to express a heterologous or homologous PKR/RNase L antagonist as a Poxvirus early protein) are modified to enhance their efficacy as immunotherapeutic agents by engineering a recombinant that expresses a virus-encoded TAP inhibitor+/−GM-CSF (as described in co-pending application Ser. No. 14/343,108) from a Poxvirus promoter into their genome. This is inserted into any Poxvirus gene not essential for replication in cell culture, or into the endogenous D9, D10 locus, or into a different locus to provide for additional safety if desired (Poxvirus tk gene, ribonucleotide reductase gene, Poxvirus growth factor gene). By expressing the TAP inhibitor+/−GMCSF, the attenuated D9, D10, and D9/10 doubly-deficient Poxvirus derivatives will persist longer in immune competent hosts and more effectively stimulate systemic immunotherapeutic responses.

The present invention is directed to the use of any Poxviridae decapping deficient mutant virus. This includes deletions of one or more viral genes encoding decapping enzymes, replacement of genes encoding decapping enzymes with reporters like EGFP, and catalytically inactive alleles such as point mutations or insertions into the genes encoding decapping enzymes that disrupt their coding capacity. Poxviridae decapping deficient mutants can also be combined with other mutations in the viral genome—for example: a thymidine kinase (tk) mutant, a Poxvirus growth factor mutant, a ribonucleotide reductase mutant, or any combination of these mutants. In fact any Poxvirus that is deficient in D9 and/or D10 decapping genes or their orthologues that encode decapping enzymes in chordopoxviridae subfamily members (described below) can be used as oncolytic viruses in the present invention, irrespective of other mutations present in the Poxvirus genome backbone.

Among the poxviruses usable in practicing the invention are members of the chordopoxviridae subfamily. Poxviridae is a virus family. Two subfamilies comprise the family Poxviridae: chordopoxviridae, which infect vertebrates, and Entomopoxviridae, which infect invertebrates. Presently, the International Committee on Taxonomy of Viruses (ICTV) recognizes ten assigned and one unassigned genera within the chordopoxviridae subfamily: avipoxviruses (species: Canarypox virus, Fowlpox virus, Juncopox virus, Mynahpox virus, Pigeonpox virus, Psittacinepox virus, Qailpox virus, Sparrowpox virus, Starlingpox virus, Turkeypox virus); Capripoxviruses (species: Goatpox virus, Sheeppox virus, Lumpy skin disease virus); Cervidpox virus (species: Mule deerpox virus); Crocodylidpoxvirus (species: Nile crocodile poxvirus); Leporipoxviruses (species: Hare fibroma virus, Myxoma virus, Rabbit fibroma virus, squirrel fibroma virus); Molluscipoxvirus (species: Molluscum contagiosum virus); Orthopoxviruses (Camelpox virus, cowpox virus, Ectromelia virus, Monkeypox virus, Racoonpox virus, Skunkpox virus, Taterapox virus, Vaccinia Virus, Volepox virus, Variola virus); Parapoxviruses (species: Bovine popular stomatitis virus, Orf virus, Parapoxvirus of red deer in New Zealand, Pseudocowpox virus); Suipoxvirus (species: swinepox virus); Unassigned (species: squirrelpox virus); Yatapoxviruses (species: Tanapoxvirus, Yaba monkey tumor virus, Yaba-like disease (YLD) virus).

Sequencing representative members of each genus has established that most contain two adjacent open reading frames that encode polypeptides with a nudix hydrolase or MuT motif, a conserved 23 amino acid sequence $GX_5$-$EX_5$ [UA]XREX$_2$-EEXGU where U represents an aliphatic, hydrophobic residue and X represents any amino acid. The Nudix hydrolase motif is found in a variety of pyrophosphatases and is a signature functional motif required for decapping enzyme activity (Koonin, 1993; Bessman et al, 1996; Dunckley & Parker, 1999; Van Dijk et al., 2002; Wang et al., 2002; Cohen et al., 2005; Parrish et al., 2007). Moreover, the glycine (G), glutamate (E), and arginine (R) residues are perfectly conserved in orthologs of VACV D9 and D10. Comparison of chordopoxvirus genomes revealed an ortholog of VACV D10 in all sequenced chordopoxvirus species (Parrish & Moss 2007). An ortholog of VACV D9, however, was absent from bovine popular stomatitis virus, orf virus, members of the parapoxvirus genus and from an attenuated, highly passaged Fowlpox vaccine strain (Parrish & Moss, 2007; Laidlaw & Skinner, 2004).

A variety of chordopoxvirus sub-family members besides VACV can be utilized as oncolytic viruses including myxoma, Yaba-like disease virus, Raccoonpox virus, squirrelpox virus (reviewed in Kim et al. 2015). Other chordopoxviruses including canary pox have been used to derive recombinant vaccine vectors and can be adapted for use in oncolytic virus therapy (for example, see Rerks-Ngarm, S. et al. 2009). In fact, any member of the chordopoxvirus subfamily can be modified for use as an oncolytic virus in the present invention by rendering decapping enzyme gene or genes (orthologs of VACV D9 or D10) non-functional to achieve preferential growth on cancer cells. This can be done using techniques well known to those of ordinary skill in the art as described in Example 1 below. Inactivation of decapping enzymes in other chordopoxviruses can be accompanied by additional mutations in other viral genes including ribonucleotide reductase or thymidine kinase (tk) as described in Example 11 below.

Non-limiting examples of Poxviruses for use in the present invention include Raccoonpox virus (ATCC® VR-2212™); Cowpox virus (ATCC® VR-302™); Rabbitpox virus (ATCC® VR-1591™); Myxoma virus (ATCC® VR-115™); Canarypox virus (ATCC® VR-111™); Yaba-like disease virus (ATC) Fowlpox virus (ATCC® VR-229™); Fowlpox virus (ATCC® VR-251™); Fowlpox virus (ATCC® VR-250™); Fowlpox virus (ATCC® VR-249™); Bovine papular stomatitis virus (ATCC® VR-801™); Pseudocowpox virus (ATCC® VR-634™); Rabbit fibroma virus (ATCC® VR-364™); Squirrel fibroma virus (ATCC® VR-236™); Ectromelia virus (ATCC® VR-1374™) and Yaba monkey tumor virus (ATCC® VR587™).

Additional Poxviruses include:
Squirrel pox virus [Kim, M., Ahn, J. S., Yun, C. O., and Kim, B Y. 2014a. Squirrel pox-virus as a novel oncolytic agent. The 40th annual meeting of Korean Cancer Association. Seoul Korea. June 20.]
Sheep and goat pox virus [(D. L. Rock) J Virol. 2002 June; 76(12): 6054-6061].
Lumpy skin disease virus [DL Rock, J. Virol. August 2001 Vol. 75 No. 15 7122-7130].
Nile crocodile poxvirus [natural outbreaks on commercial crocodile farms in Africa, USDA investigators i.e.: J. Virol. May 2006 vol. 80 No. 10, 4978-4991
Pigeon pox [commercially available from MERCK animal health].
Volepox virus [wild California mice or CDC (PLoS One. 2012; 7(8): e43881.)]
Junco pox [wild isolates or academic labs (Virus Res 10: 65-76).
Quail pox virus [commercially available live vaccines for use in quails (R. W. Winterfield (1985). Poultry Science 64:65-70 (1985)). Also wild isolates (described in Veterinary Microbiology Volume 140, Issues 1-2, 6 Jan. 2010, pages 1-8)]
Sparrow pox, Turkey pox [described in Veterinary Microbiology Volume 140, Issues 1-2, 6 Jan. 2010, pages 1-8)]
Mynah pox virus [disclosed in Hsieh Y C, Chen S H, Wang C W, Lee Y F, Chung W C, Tsai M C, Chang T C, Lien Y Y, Tsai S S. Avian Pathol. 2005 October 34(5):415-7.)]
Parapoxvirus of red deer [disclosed in Robinson A. J., Mercer A. A. (1995). Parapoxvirus of red deer: evidence for its inclusion as a new member in the genus parapoxvirus. Virology 208, 812-815)]

Preferred Poxviruses for use in the present invention include without limitation VacV strains Western Reserve (ATCC VR-1354), NYCBofH-Wyeth (ATCC VR-1536), Modified Vaccinia Virus Ankara (ATCC VR-1566) and Lister (ATCC VR-1549).

In addition, Poxviridae decapping deficient mutant viruses of the invention can be combined with immune checkpoint inhibitors well known to those of ordinary skill in the art. Among the immune checkpoint inhibitors useful in practicing the present invention are antibodies directed against the following cellular proteins: PD1, PDL1, CTLA4, Tim-3, BTLA, Lag-3 and Tigit.

A number of checkpoint inhibitors for use in the present invention are commercially available for administration to human patients suffering from cancer as set forth below:

Anti-CTLA4, Ipilimumab, Bristol Myers Sqibb [FDA approved]

Anti-PD1, pembrolizumab, Merck Sharp & Dohme Corp; [FDA approved]; Nivolumab Bristol Myers Sqibb [FDA approved]

Anti-PDL1, Durvalumab (MEDI4736), AstraZeneca/Medimmune; [FDA approved] MPDL3280A Roche/Genentech [FDA approved]

Additional checkpoint inhibitors for use in the present invention include Anti-Tim-3 (Tesaro, Inc); Anti-BTLA (Genentech, Inc.); and Anti-Tigit (Genentech, Inc.).

Pursuant to the present invention Poxviridae decapping deficient mutant viruses of the invention are used in a method of treating the human or animal body. In particular, viruses of the invention are used in methods of cancer therapy. Preferably, variant Poxviruses of the invention are used to treat cancer by oncolytic virus immunotherapy. This involves a two component mechanism wherein the virus replicates preferentially in the tumor and i) destroys the tumor by direct viral oncolysis; and ii) stimulates an anti-tumor immune response that facilitates a systemic anti-tumor adaptive immune response. Such treatment will reduce the tumor burden in the recipient.

Viruses of the invention are used in the therapeutic treatment of any solid or non-solid tumor in a mammal, preferably in a human, but can be an animal, including a laboratory animal in the context of a clinical trial or screening or activity experiment. Thus, as can be readily appreciated by those of ordinary skill in the art, the methods and compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

For veterinary medical use, it is preferred to use a Poxvirus that replicates in cells of the recipient but it does need to be a perfect match. For example, vaccinia virus replicates in canine cells and has been used in pre-clinical studies as an oncolytic virus to treat tumors in dogs. However, Poxviruses that replicate poorly in normal cells of a given species may actually replicate in tumor cells of that species. For example, myxoma was thought to be a rabbit specific poxvirus but replicates in human tumor cells. Therefore, the determination of the particular Poxvirus to administer can be determined by routine experimentation well known to those of ordinary skill in the art using in vitro assays for inhibition of tumor/cancer cell growth and/or for killing tumor cells, such as colony formation or dye uptake; antitumor/antitumor efficacy experiments are then performed in vivo.

The viruses of the invention are administered to a subject afflicted with prostate, breast, lung, liver, renal cell, endometrial, bladder, colon or cervical carcinoma; adenocarcinoma; melanoma; leukemia; lymphoma; glioma; sarcomas such as soft tissue and bone sarcomas; or cancer of the head and neck, and, preferably, bladder cancer.

The term "cancer" refers to all types of cancer, neoplasm or malignant tumors found in mammals, including leukemia, lymphoma, carcinomas and sarcomas. Non-limiting examples of cancers include cancer of the breast, brain, cervix, colon, head & neck, liver, kidney, lung, non-small cell lung, melanoma, mesothelioma, ovary, sarcoma, stomach, uterus and medulloblastoma. Additional examples include, blood dyscrasia's such as Hodgkin's Disease, Non-Hodgkin's Lymphoma, and multiple myeloma, as well as neuroblastoma, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniformi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, and carcinoma *villosum*.

As used herein the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

In certain embodiments, the oncolytic viruses provided herein are useful for killing tumor cells selected from the group consisting of astrocytoma, oligodendroglioma, meningioma, neurofibroma, glioblastoma, ependymoma, Schwannoma, neurofibrosarcoma, medulloblastoma, melanoma cells, pancreatic cancer cells, prostate carcinoma cells, breast cancer cells, lung cancer cells, colon cancer cells, hepatoma cells, mesothelioma and epidermoid carcinoma cells.

The variant Poxvirus oncolytic immunotherapy disclosed herein can be combined with conventional cancer therapies such as chemotherapy, radiation therapy, thermotherapy, surgery (tumor resection) and TACE (transarterial chemoembolization), to treat mammals suffering from tumors or harboring cancer cells. In addition, such therapy can be combined with other anti-tumor/anti-cancer therapies, including but by no means limited to small tyrosine kinase inhibitors (e.g., sorafenib, erlotinib, gefitinib, brivanib, sunitinib, lapatinib, cediranib, vatalanib), monoclonal antibodies (e.g. cetuximab, bevacizumab, IMC-A12, IMC1121B, panitumumab, trastuzumab), suicide gene therapy (i.e., introduction of genes that encode enzymes capable of conferring to tumor cells sensitivity to chemotherapeutic agents such as thymidine kinase of herpes simplex virus or varicella zoster virus and bacterial cytosine deaminase), anti-oncogene or tumor suppressor gene therapy (e.g., using anti-oncogene molecules including monoclonal antibodies, single chain antibody vectors, antisense oligonucleotide constructs, ribozymes, immunogenic peptides, etc.), administration of tumor growth inhibitors (e.g., interferon (IFN)-γ, tumor necrosis factor (TNF)-α, TNF-β, and similar cytokines, antagonists of tumor growth factor (TGF)-β and IL-10, etc.), administration of angiogenesis inhibitors (e.g., fragments of angiogenic polypeptides that are inhibitory [such as the ATF of urokinase], angiogenesis inhibitory factors [such as angiostatin and endostatin], tissue inhibitors of metalloproteinase, soluble receptors of angiogenic factors [such as the urokinase receptor or FGF/VEGF receptor], molecules which block endothelial cell growth factor receptors, and Tie-1 or Tie-2 inhibitors), vasoconstrictive agents (e.g., nitric oxide inhibitors), immune therapies with an immunologically active polypeptide (including immunostimulation, e.g., in which the active polypeptide is a cytokine, lymphokine, or chemokine [e.g., GM-CSF], and vaccination, in which the active polypeptide is a tumor specific or tumor associated antigen), and any other small molecules useful for treating cancer including pro-apoptotic agents (e.g. mapatumumab), proteosome inhibitors (e.g. bortezomib), cell cycle inhibitors (e.g. flavopiridol), DNA methylation inhibitors (e.g. 5-Aza-cytidine) and the like.

The mutant Poxviruses of the present invention can also be engineered to express additional immune stimulating cytokines including, but are not limited to: IL-1, IL-2, IL-3, IL-4, IL-5, IL-6 IL-7, IL-8, IL-9, IL-10, IL-11, IL-12, IL-13, IL-14, IL-15, IL-16 and IL-17. Additional cytokines include IL-18-IL-36. In addition to CCL17, other chemokines can also be used, including, but not limited to, CCL1-CCL27 and other CC chemokines, CXCL1-CXCL13 and other CXC chemokines, C chemokines, and CX3C chemokines. Cytokine or chemokine receptors and soluble receptors can also be used. In addition, different combinations of the above-mentioned (or alternative) cytokines can be used.

Once a variant Poxvirus of the invention has demonstrated some degree of activity in vitro at inhibiting tumor/cancer cell growth and/or at killing tumor cells, such as colony formation or dye uptake, antitumor/antitumor efficacy experiments may be performed in vivo. Rodent systems can be used for initial assays of antitumor activity since tumor growth rates and survival endpoints are well-defined, and since these animals generally reflect the same types of toxicity and drug metabolism patterns as in humans. For this work, syngeneic (same gene line) tumors are typically harvested from donor animals, disaggregated, counted and then injected back into syngeneic (same strain) host mice at two different sites on opposite flanks of the same animal. This bilateral implant model makes it possible to precisely measure the response of a locally treated tumor and an untreated tumor at a distant site. Variant Poxviruses are typically then injected at some later time point(s), preferably by in situ injection into the tumor site or by intravenous infusion into the tail vein. Tumor growth rates and/or survival are determined and compared to untreated controls. In these assays, growth rates are typically measured for tumors growing in the flank of the animal, wherein perpendicular diameters of tumor width are translated into an estimate of total tumor mass or volume. The time to reach a predetermined mass is then compared to the time required for equal tumor growth in the untreated control animals. The role of the virus in stimulating an anti-tumor adaptive immune response can be assessed by measuring IFN gamma production of isolated T cells exposed to killed tumor cells. In addition, the anti-tumor activity of variant Poxviruses of the invention can be evaluated in animals depleted for CD8+ T-cells. This can easily be achieved using anti-CD8+ T cell antibodies by those skilled in the art.

Human tumors have been successfully transplanted in a variety of immunologically deficient mouse models. A mouse called the nu/nu or "nude" mouse can be used to develop in vivo assays of human tumor growth. In nude mice, which are typically hairless and lack a functional thymus gland, human tumors (millions of cells) are typically injected in the flank and tumor growth occurs slowly thereafter. This visible development of a palpable tumor mass is called a "take". Anticancer drugs such as the mutant Poxviruses disclosed herein are then injected by some route (intravenous, intramuscular, subcutaneous, per os) into or distal to the tumor implant site, and growth rates are calculated by perpendicular measures of the widest tumor widths as described earlier. A number of human tumors are known to successfully "take" in the nude mouse model. An alternative mouse model for this work involves mice with a severe combined immunodeficiency disease (SCID), in which there is a defect in maturation of lymphocytes. Because of this, SCID mice do not produce functional B- and T-lymphocytes. However, these animals do have normal natural killer (NK) cell activity. Nonetheless, SCID mice will "take" a large number of human tumors. Tumor measurements and drug dosing are generally performed as above. Again, positive compounds in the SCID mouse model are those that inhibit tumor growth rate by >20-50% compared to the untreated control.

Administration

The variant Poxviruses of the invention or compositions, e.g., pharmaceutical formulations, comprising the variant Poxviruses, may be administered to a subject, e.g., patient, preferably a human patient suffering from cancer and in need of such treatment as described further below.

A subject or patient in need treatment with the variant Poxvirus of the invention or compositions, e.g., pharmaceutical formulations, comprising the variant Poxvirus is an individual suffering from cancer, preferably an individual with a solid tumor exhibiting metastases or a non-solid tumor such as leukemia, lymphoma, or myeloma, and preferably is one who would benefit by the administration of the variant Poxvirus or pharmaceutical formulations thereof. The aim of therapeutic treatment is to improve the condition of a patient. Typically, although not necessarily, therapeutic treatment using a variant Poxvirus of the invention or of the invention alleviates the symptoms of the cancer. A method of treatment of cancer according to the invention comprises administering a therapeutically effective amount of a variant Poxvirus of the invention or of a pharmaceutical formulation containing the variant Poxvirus to a patient suffering from cancer. Administration of an oncolytic Poxvirus variant or composition of the invention to an individual suffering from a tumor will typically kill the cells of the tumor, thus decreasing the size of the tumor and/or reducing or preventing spread of malignant cells from the tumor. In addition, intravenous administration of the variant Poxvirus will seed infections of tumor beds in metastases, thus facilitating immunotherapeutic responses throughout the patient, promoting a durable anti-tumor response, and leading to increases in overall patient survival.

The variant Poxvirus of the present invention or pharmaceutical formulations thereof are administered systemically, i.e. parenterally, transmucosally, e.g., orally (per os), nasally, rectally, or transdermally. Parental routes include intravenous, intra-arteriole, intra-muscular, intradermal, subcutaneous, intraperitoneal, intraventricular, and intracranial administration. For example, a variant Poxvirus-containing composition is administered by injection, intravenous infusion, instillation or inhalation. A preferred route of administration is by direct injection or by intravenous infusion. For example, therapeutic treatment may be carried out following direct injection of the variant composition into target tissue (i.e., "in situ administration"). The target tissue may be the tumor or a blood vessel supplying the tumor.

Variant Poxvirus containing compositions may be formulated for parenteral administration by injection, e.g., by bolus injection or continuous intravenous infusion. Formulations for injection may be prepared in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents as is well known in the art.

In addition to the formulations described previously, variant Poxviridae decapping deficient mutant virus-containing compositions may also be formulated as a depot preparation. Such long acting formulations may be administered by implantation (for example subcutaneously or intramuscularly) or by intramuscular injection. Thus, for example, the variant Poxvirus-containing compositions may be formulated with suitable polymeric or hydrophobic materials (for example, as an emulsion in an acceptable oil such as petroleum, an animal, vegetable or synthetic origin oil, such as peanut oil, soybean oil, mineral oil, sesame oil) or ion exchange resins, or as sparingly soluble derivatives, for example, as a sparingly soluble salt. In yet another embodiment, the therapeutic compound can be delivered in a controlled release system. For example, a variant Poxvirus may be administered using intravenous infusion with a continuous pump, in a polymer matrix such as poly-lactic/glutamic acid (PLGA), a pellet containing a mixture of cholesterol and the active ingredient (Silastic®; Dow Corning, Midland, Mich.; see U.S. Pat. No. 5,554,601) implanted subcutaneously, an implantable osmotic pump, a transdermal patch, liposomes, or other modes of administration. In another embodiment, the active ingredient can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

The routes of administration and dosages described are intended only as a guide since a practitioner of ordinary skill in the art will be able to determine readily the optimum route of administration and dosage. The dosage may be determined according to various parameters, especially according to the location of the tumor, the size of the tumor, the age, weight and condition of the patient to be treated and the route of administration. The optimum route of administration will depend on the location and size of the tumor.

Administration of a variant Poxvirus-containing composition may be once a day, twice a day, or more often, but frequency may be decreased during a maintenance phase of the disease or disorder, e.g., once every second or third day instead of every day or twice a day. The dose and the administration frequency will depend on the clinical signs, which confirm maintenance of the remission phase, with the reduction or absence of at least one or more preferably more than one clinical signs of the acute phase known to the person of ordinary skill in the art. More generally, dose and frequency will depend in part on recession of pathological signs and clinical and subclinical symptoms of a disease condition or disorder contemplated for treatment with the present compounds.

Keeping the above description in mind, the amount of virus administered by direct injection into the tumor (a therapeutically effective amount, as described below) in the case of Poxvirus will be in the range from between about $10^4$ and about $10^{10}$ pfu, preferably between about $10^5$ and about $10^8$ pfu, more preferably between about $10^6$ and about $10^9$ pfu. Typically 1-4 ml, such as 2 to 3 ml of a pharmaceutical composition comprising the virus and a pharmaceutically acceptable suitable carrier or diluent would be used for direct injection into an individual tumor. [See, Senzer et al. J Clin Oncol (2009) 27(34):5763-5771.] However for some oncolytic therapy applications larger volumes up to 10 ml may also be used, depending on the tumor type, tumor size and the inoculation site and method of delivery. Likewise, smaller volumes of less than 1 ml may also be used. Dosages and administration regimen can be adjusted depending on the age, sex and physical condition of the subject or patient as well as the benefit of the treatment and side effects in the patient or mammalian subject to be treated and the judgment of the physician, as is appreciated by those of ordinary skill in the art. The amount of virus administered by iv infusion into the tumor (a therapeutically effective amount, as described below) in the case of Poxvirus will be in the range from between about $10^4$ pfu per kg body weight to about $3 \times 10^7$ pfu per kg body weight or an absolute fixed dose of $10^9$ or $10^{10}$ pfu.

The term "therapeutically effective" when applied to a dose or an amount refers to that quantity of a compound or pharmaceutical composition that is sufficient to result in a desired activity upon administration to a mammal in need thereof. As used herein with respect to the Poxviridae decapping deficient mutant viruses of the invention, the term "therapeutically effective amount/dose" refers to the amount/dose of a virus or pharmaceutical composition containing the compound that is sufficient to produce an effective anti-tumor response upon administration to a mammal.

The dose to be administered ("therapeutically effective amount"), can be determined by escalating the dose from a minimum level to an effective concentration. Such dosage adjustments are well known to those of ordinary skill in the art. Knowledge of a dose at which signs of toxicity begin to show may be determined in a similar fashion. The minimum effective dose, determined by titration and monitoring, is preferred as a therapeutic dose, determined experimentally in murine models and in approved clinical trials for human usage. The present invention includes pharmaceutical formulations or dosage forms for treating mammals suffering from a tumor disclosed herein. When formulated in a pharmaceutical composition, the Poxviruses of the present invention can be admixed with a pharmaceutically acceptable carrier or excipient.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human.

Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicles with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The present invention is described further below in examples which are intended to further describe the present invention without limiting the scope thereof.

In the examples below the following materials and methods were employed.

Antibodies and Chemicals

Monoclonal E3L antiserum was a kind gift from S. Isaacs (Univ. Pennsylvania, PA). Polyclonal PABP1 antiserum was a kind gift of S. Morley (Univ. Sussex, UK). I3 antiserum was a kind gift of D. Evans (Univ. Alberta, Canada) All other antibodies were purchased commercially, as follows: Xrn1 (A300-443A; Bethyl Labs), α tubulin (6074; Sigma), eIF2α (5324; Cell Signaling), phospho(ser51)-eIF2α (3398; Cell Signaling), PKR (12297; Cell Signaling), phospho(T446)-PKR (32036; Abcam), PERK (5683; Cell Signaling), Hsc70 (10011384; Cayman Chemical); RNase L (13825; Abcam), dsRNA (J2; SciCons, Hungary). Phosphonoacetic acid (PAA) was from Sigma.

Immunofluorescence

Cells were seeded onto glass coverslips and transfected/infected cells fixed with 4% formaldehyde for 15 min and permeabilized with 0.5% Triton X-100. For RNase treatments cells were incubated in RNase Buffer (10 mM Tris: HCl [pH8.3], 10 mM $MgCl_2$, 1 mM DTT, 60 mM NaCl) containing 50 u/ml RNase III (E6146S; NEB) or 50 μl/ml RNase ANT1 mix (AM2286; Ambion), reflecting 25 u/ml and 1000 u/ml respectively for 15 min at 37° C. Samples were then blocked in 4% FBS, incubated with primary antisera and incubated with anti-mouse AlexaFluor 488 (A11029; Life technologies) secondary antibody for 1 h at room temperature. DNA was stained with 4', 6'-diamidino-2-phenylindole (DAPI). The fluorescence images were collected with a Zeiss LSM710 confocal microscope or a Zeiss Axiovert fluorescence microscope, using Zen 2008 software (Zeiss).

Immuno-Dot Blotting of dsRNA

NHDFs were lysed in cytoplasmic lysis buffer (15 mM Tris [pH 7.5], 0.3M NaCl, 15 mM $MgCl_2$, 1% Triton X-100, 100 u/ml RNase inhibitor (Fermentas)) containing complete EDTA-free protease inhibitors (Roche) for 15 min on ice. Samples were centrifuged for 1 min at 12,000 RCF at 4° C. and supernatants collected. 5 μl of extracts were dotted onto PVDF membrane and allowed to dry. RNA was then cross-linked using two pulses of 0.125 $J/cm^2$ UV light in a Stratalinker (Stratagene). The membrane was then processed as for an immunoblot. Dot blots were quantified from film using Licor Image studio software to calculate signal intensity adjusted for background.

dsRNA Immunoprecipitation

Approximately $4 \times 10^6$ siRNA-transfected VACV-infected (MOI=5) NHDFs were washed twice with cold PBS on ice and lysed in 1 ml IP buffer (15 mM Tris [pH 7.5], 0.1M NaCl, 5 mM $MgCl_2$, 0.5% Triton X-100, 1 mM dithiothreitol, 100 u/ml RNase inhibitor (Fermentas)) containing complete EDTA-free protease inhibitors (Roche) for 10 min on ice. Lysate was centrifuged for 1 min at 12,000 RCF at 4° C. and supernatant collected. This was pre-cleared with 40 μl of protein-G±agarose beads (25% slurry; Santa Cruz; SC-2002) for 1 h at 4° C. before incubation of lysate with 7 μg J2 dsRNA antibody overnight at 4° C. on a rotating wheel. Lysate was then incubated with 40 μl of protein-G±agarose beads for 3 h at 4° C. Beads were then washed with IP buffer 4 times then treated with either 20 u/ml RNase III or 20 μl/ml RNase A/T1 (25 u/ml/1000 u/ml respectively) for 15 min at 37° C. Beads were then washed 3 times and resuspended in 1 ml Trizol for RNA isolation.

Example 1: Preparation of VacV D9, D10, and D9/D10 Doubly-Deficient Mutant Viruses Although this example describes the preparation of a vaccinia virus decapping deficient mutant virus, these techniques, with minor modifications known to those of ordinary skill in the art, can be used to generate the Poxviridae decapping deficient mutant viruses of the invention.

Construction of Recombinant Viruses

VacV recombinants are derived from the WR strain of VACV (ATCC VR-1354). D9 and D10 deficient VACV are constructed by replacing the D9 or D10 open reading frames (ORF) with the EGFP ORF as described (Parrish & Moss, 2006). Alternatively, viruses with catalytic site mutations in D9, D10 or both ORFs are constructed as described (Liu et al, 2014; 2015). For example, vD10mu, with catalytic site mutations E144Q and E145Q (vD10mu) are isolated by repairing the EGFP mutation in D10-deleted VACV with a D10 allele containing E144Q and E145Q mutations via homologous recombination as described (Liu et al., 2014). Likewise, the D9 catalytic site (vD9mu) mutants are constructed by replacing the EGFP open reading frame (ORF) in D9-deleted VACV (Parrish and Moss, 2006) with a D9 allele containing the catalytic site mutations E129Q and E130Q. The D9/D10 doubly-deficient mutant is generated in two steps: homologous recombination is used to replace the D9 ORF of vD10mu with the EGFP ORF; second, the EGFP ORF is replaced by the D9 ORF with active site mutations E129Q and E130Q. D9/D10 doubly deficient mutants need to be isolated on BHK21 cells as described (Liu et al., 2015) whereas viruses individually deficient for D9 or D10 are isolated on standard monkey kidney cell lines (i.e., BSC40, BSC1). Plaques are screened (EGFP positive or negative, depending upon the isolation scheme) under a fluorescent microscope and clonally purified. The physical structure of viral recombinants is verified by Southern analysis and direct sequencing of relevant PCR amplified segments.

Virus Purification

Recombinant viruses, grown in BSC40 cells [available from the American Type Culture Collection, ATCC, as CRL-2761] are purified by centrifugation through a 36% sucrose cushion followed by centrifugation through a 24%-40% sucrose gradient as described (Liu et al., 2014). BHK-21 cells are used for plaque assay to determine infectivity.

Example 2: Inhibition of Infected Cell Protein Synthesis and VacV Replication by Xrn1-Depletion Although factors important for RNA metabolism and translation, including Xrn1, were identified in a high throughput format, genome-wide RNAi screen for host proteins affecting GFP-expressing VacV spread in an established, transformed cell line, the reliance of the virus on host mRNA decay pathways for infectious virus production was not further investigated (Sivan et al., 2013). Normal primary human fibroblasts (NHDFs) were treated with control, non-silencing (ns) siRNA or one of two independent Xrn1 specific siRNAs and infectious virus production quantified by plaque assay in permissive BSC40 cells. Compared to control, ns siRNA treated cultures, both individual Xrn1-specific siRNAs effectively depleted Xrn1 protein levels and reduced viral replication and spread 100-500-fold (FIG. 1A, 1B). To address the possibility that Xrn1-depletion might interfere with the VacV-induced suppression of host protein synthesis, mock and VacV-infected NHDFs were metabolically labeled with [$^{35}$S]-containing amino acids and the proteins that were synthesized were separated by SDS-PAGE and visualized by autoradiography. In control, ns siRNA-treated cultures, the global protein synthesis profile in mock-infected cells was effectively suppressed by VacV infection, which resulted in high level viral protein synthesis (FIG. 1C, compare lanes 1 vs 5). Surprisingly, while Xrn1 depletion had little detectable impact on protein synthesis in mock-infected NHDFs (FIG. 1C, lane 1 vs 2), it dramatically reduced all protein synthesis in VacV-infected cells (lanes 5 vs 6). This phenotype was dependent on viral gene expression, as it was not observed in cells infected with UV-inactivated virus (FIG. 1C, lanes 3 vs 4).

Figure 8:
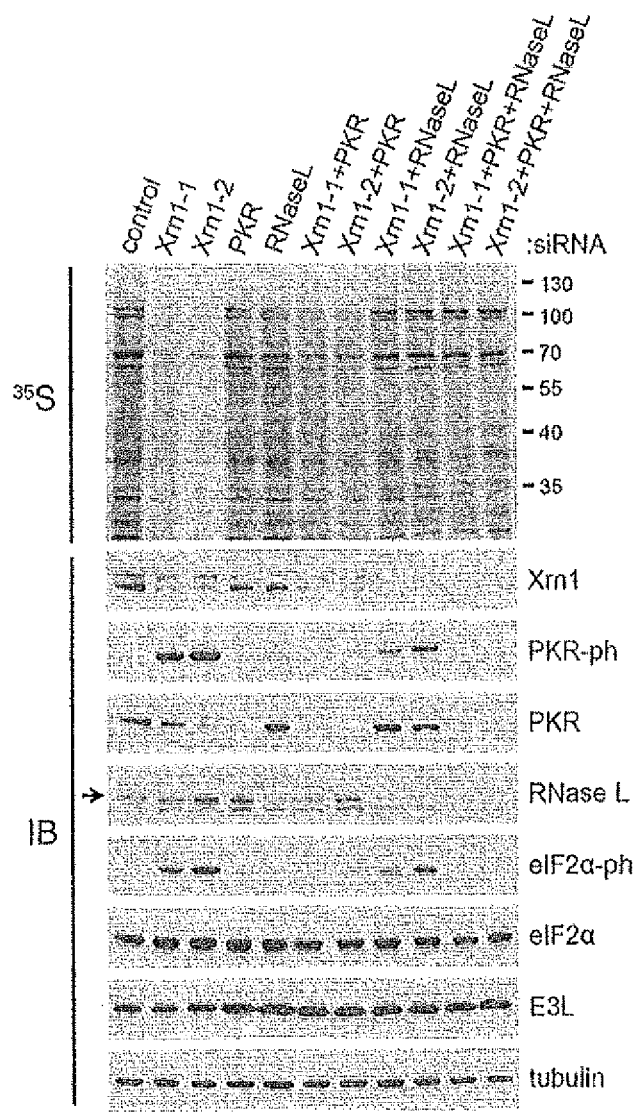
FIG. 8. Inhibition of VACV protein synthesis by Xrn1-depletion, related to FIG. 1. [$^{35}$S] incorporation into metabolically labeled samples in described in FIGS. 1D and 2 additional independent replicate experiments was quantified by TCA precipitation and scintillation counting. Means are plotted ±SEM.

As D9 and D10 decapping enzymes stimulate mRNA decay (Parrish et al., 2007), uncapped mRNAs will accumulate in Xrn1-depleted, VacV-infected cells and perhaps inhibit translation or result in cell stress. To determine if either D9 or D10 were required to globally inhibit translation in Xrn1-depleted NHDFs, the dependence of ongoing protein synthesis on Xrn1 was examined in cells infected with a D9 (ΔD9) or D10-deficient (ΔD10) virus. However, rather than suppressing the phenotype, the inhibition of protein synthesis in Xrn1-depleted cells was even more pronounced in cells infected with ΔD9 compared to ΔD10 or WT VacV (FIGS. 1D, 8). Thus, while the inhibition of protein synthesis in Xrn1-depleted, VacV-infected NHDFs was readily observed in the absence of D9 or D10, Xrn1 and the VacV-encoded D9 decapping enzyme showed a synthetic genetic interaction, consistent with their participation in a common pathway (FIGS. 1D; 8).

The global inhibition of ongoing protein synthesis in Xrn1-depleted cells infected with VacV is reminiscent of the cellular response to physiological stresses achieved by inactivation of eIF2α, a critical translation initiation factor required to load 40S ribosome subunits with initiator tRNA, via phosphorylation of S51 on its α subunit (Mohr and Sonenberg, 2012; Walsh and Mohr, 2011). Significantly, the inhibition of protein synthesis in Xrn1-depleted, VacV-infected cells correlated with phosphorylated eIF2α accumulation (FIG. 1C). While levels of phosphorylated eIF2α observed in control, ns siRNA-treated NHDFs infected with ΔD9 or ΔD10 were modestly elevated compared to WT VacV (FIG. 1D, compare lanes 7, 10 vs 4), they were not sufficient to detectably suppress protein synthesis. Moreover, phosphorylated eIF2α abundance was further augmented in ΔD9 and ΔD10-infected cells by Xrn1-depletion (FIG. 1D, compare lanes 7 vs 8, 9; lanes 10 vs 11, 12). In all cases, the substantial increase in eIF2α phosphorylation in Xrn1-depleted, VacV-infected cells was unexpected, as VacV, like numerous viruses, encodes multiple functions thought to prevent eIF2α phosphorylation (Walsh et al., 2013; Walsh and Mohr, 2011).

Figure 2:
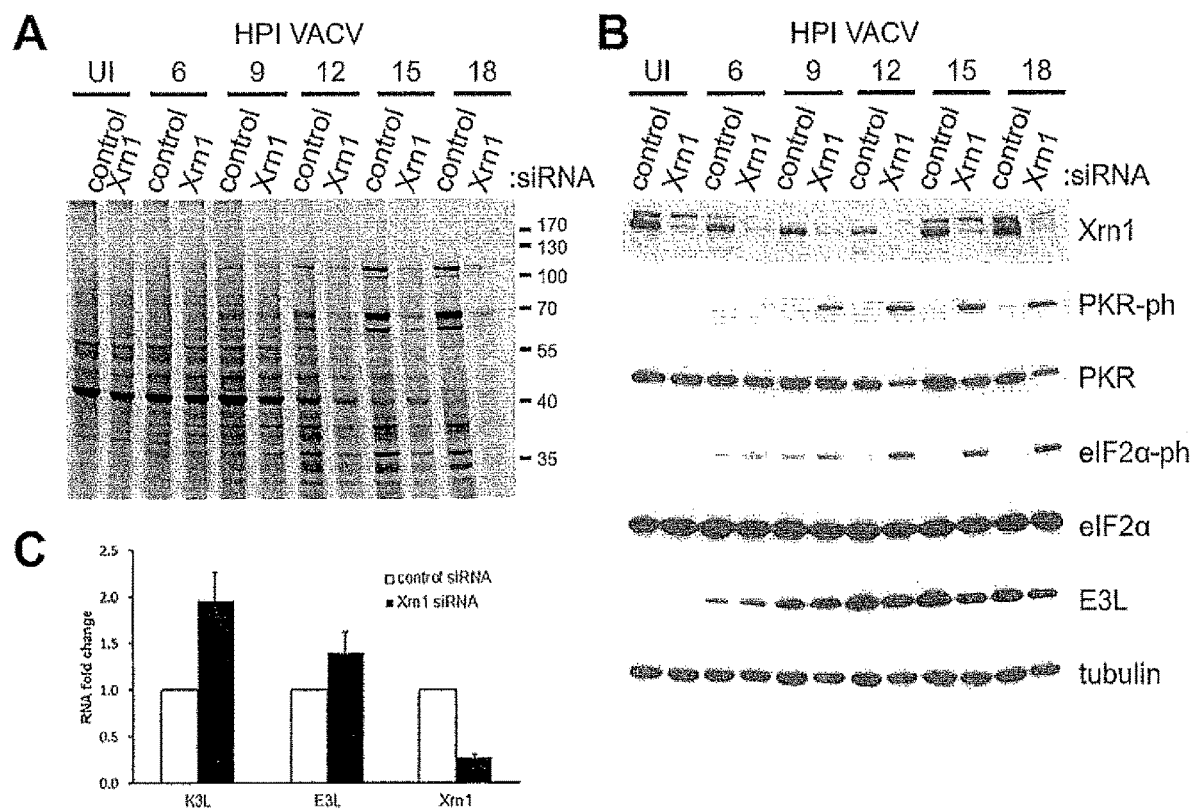
FIG. 2A-2C. Phosphorylated eIF2α accumulation in Xrn1-depleted cells correlates with global protein synthesis inhibition late in the VacV lifecycle NHDFs transfected with ns control or Xrn1-specific siRNAs were infected with VacV (MOI=5). At the indicated times (hpi) cells were metabolically pulse-labeled with [$^{35}$S] Met-Cys for 30 min. Uninfected cells (UI) were harvested in parallel with 18 hpi samples. (2A) Total protein was isolated, separated by SDS-PAGE and the fixed, dried gel exposed to X-ray film. Molecular mass standards (in kDa) are shown to the right. (2B) The same lysates were immunoblotted with the indicated antibodies. Tubulin served as a loading control. (2C) RNA from NHDFs treated with the indicated siRNAs and infected as in 2A was harvested at 6 hpi and subject to RT-qPCR using primers specific for K3L, E3L or Xrn1 mRNAs. Each reaction product was normalized to the signal obtained using primers specific for 18S rRNA and expressed as the fold change relative to control siRNA-treated cells. Means of 3 independent experiments are plotted ±SEM.

Example 4: Accumulation of Phosphorylated eIF2α is Dependent Upon a Virus-Specific Transcription Factor in Xrn1-Depeted Cells To more precisely define the point in the viral lifecycle where mRNA translation was inhibited in Xrn1-depleted cells, protein synthesis was analyzed by separating metabolically radiolabeled proteins by SDS-PAGE at different times post-infection. Little or no qualitative differences were detected between overall protein banding profiles of proteins produced in VacV-infected cells treated with control, ns siRNA vs Xrn1 siRNA at all-time points. From 9 h onward, however, radiolabeled VacV proteins were readily detected and total [$^{35}$S] incorporation into proteins throughout the lane was reduced in Xrn1-depleted cultures vs those treated with control ns siRNA (FIG. 2A). The magnitude to which protein synthesis was suppressed in Xrn1-depleted cultures vs control siRNA treated cultures increased progressively over time, and was greatest at 18 hpi when the virus-imposed suppression of host protein synthesis was strongest (FIG. 2A). Analysis of these samples by immunoblotting indicated that phosphorylated eIF2α was more abundant in Xrn1-depleted cultures at all time points tested and the inhibition of protein synthesis correlated precisely with i) phosphorylated eIF2α levels; and ii) activation of the dsRNA-dependent eIF2α kinase PKR by phosphorylation (FIG. 2B).

As vaccinia encodes two proteins to antagonize eIF2α phosphorylation (Chang et al., 1992; Seo et al., 2008), one of which is a dsRNA-binding protein that prevents PKR activation (E3L) while the other is an eIF2α kinase pseudosubstrate (K3L), it was puzzling that robust eIF2α phosphorylation was observed in Xrn1-depleted cells. One possible explanation for this was a failure to produce E3L and K3L. FIG. 2B shows that E3L is expressed at similar levels in control and Xrn1 knockdown cells at 6 and 9 hpi, when eIF2α becomes noticeably more phosphorylated in knockdown cells (FIG. 2B). It is therefore not an insufficiency of this protein that is responsible for the phenotype. In the absence of suitable antisera available for K3L, qPCR was performed and showed that E3L and K3L mRNAs were expressed in Xrn1-depleted cells, exceeding those detected in control ns siRNA treated cultures (FIG. 2C).

Figure 3:
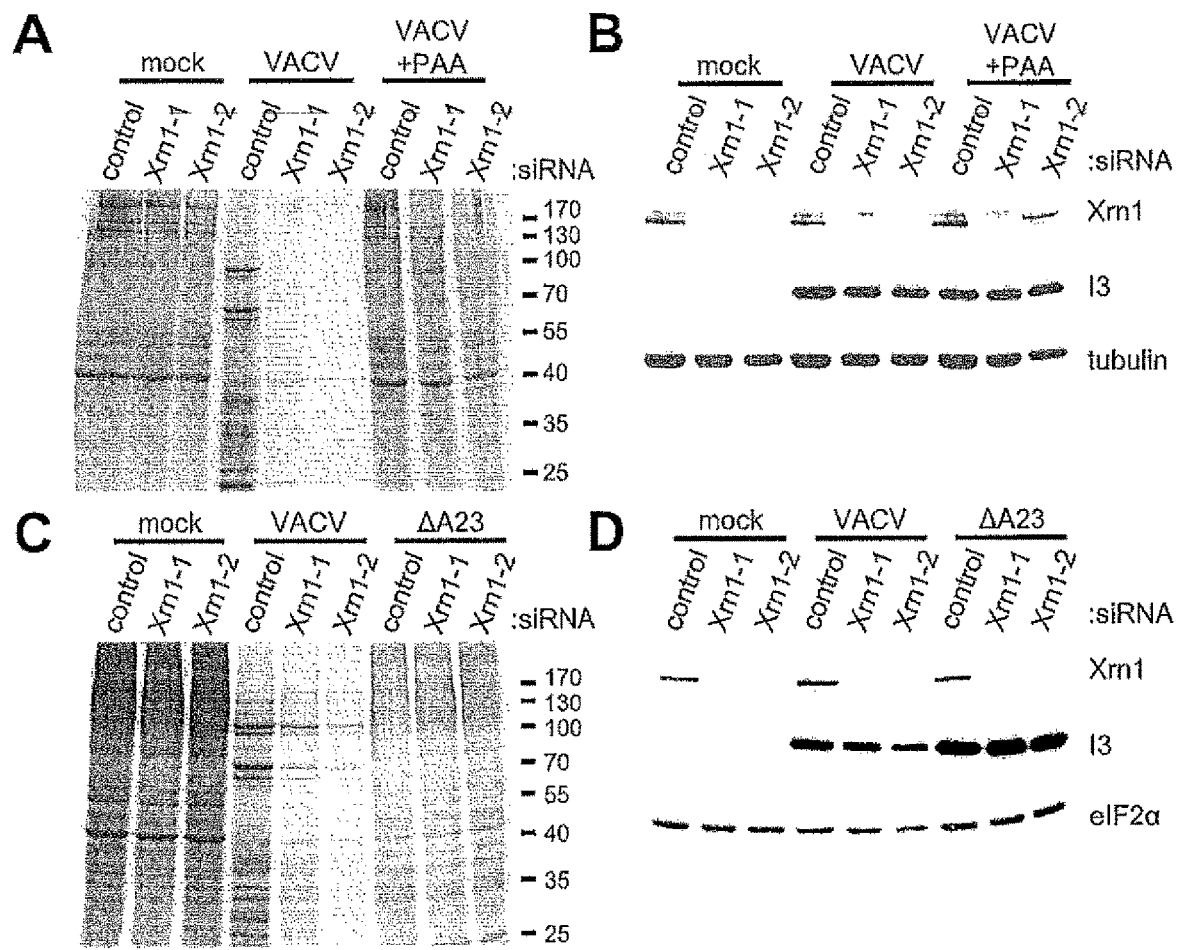
FIG. 3A-3D. Inhibition of protein synthesis following Xrn1-depletion requires a VacV specific late gene transcription factor (3A) NHDFs transfected with ns control or Xrn1-specific siRNAs (−1 and −2) were mock-infected or infected with VacV (MOI=5) in the presence or absence of PAA. At 18 hpi, cells were metabolically pulse-labeled with [$^{35}$S]Met-Cys for 30 min. Total protein was collected, separated by SDS-PAGE and [$^{35}$S]-labeled proteins visualized by exposing the fixed, dried gel to X-ray film. Molecular mass standards (in kDa) are shown to the right. (3B) The same lysates were also immunoblotted with the indicated antibodies. Tubulin was used as a loading control. VacV I3 (early expressed) serves as an infection control. (3C) As in 3A except NHDFs were infected with WT VacV or an A23-deficient virus (ΔA23). (3D) Lysates from C were immunoblotted with the indicated antibodies. eIF2α was used as a loading control.

Having shown that infection with UV-inactivated VacV, which delivers virion cargo into infected cells but cannot express viral genes, is insufficient to inhibit protein synthesis in Xrn1-depleted cells (FIG. 1C), infected NHDFs were treated with phosphonoaceitic acid (PAA) to inhibit the viral DNA dependent DNA polymerase. Importantly, PAA treatment prevented the cessation of protein synthesis observed in Xrn1-depleted, VacV-infected NHDFs, suggesting that viral DNA synthesis or an event closely associated with viral DNA synthesis like intermediate/late gene expression were required to trigger this phenotype (FIG. 3A). As VacV-induced inhibition of host protein synthesis is typically visible late in infection and is suppressed by PAA, expression of the viral early/intermediate gene product I3L was used to verify that the PAA-treated cells were indeed infected and had advanced to a stage preceding viral DNA replication (FIG. 3B). To further parse the requirements to trigger the inhibition of VacV infected cell protein synthesis by Xrn1-depletion, NHDFs were infected with a virus deficient in the intermediate transcription factor A23 (ΔA23) (Warren et al., 2012). While ΔA23-infected cells replicate viral DNA, they do not express intermediate or late genes whose transcription follows viral DNA synthesis and is absolutely dependent upon the A23 protein. Unlike WT VacV-infected cultures, protein synthesis proceeds and is not detectably impaired in Xrn1-depleted NHDFs infected with ΔA23 (FIG. 3C, D). This indicates that the global inhibition of translation in Xrn1-depleted, VacV-infected cells is not triggered by viral DNA synthesis, but is instead dependent upon a specific virus transcription factor required for the biogenesis of discrete intermediate and late populations of VacV mRNAs.

Figure 4:
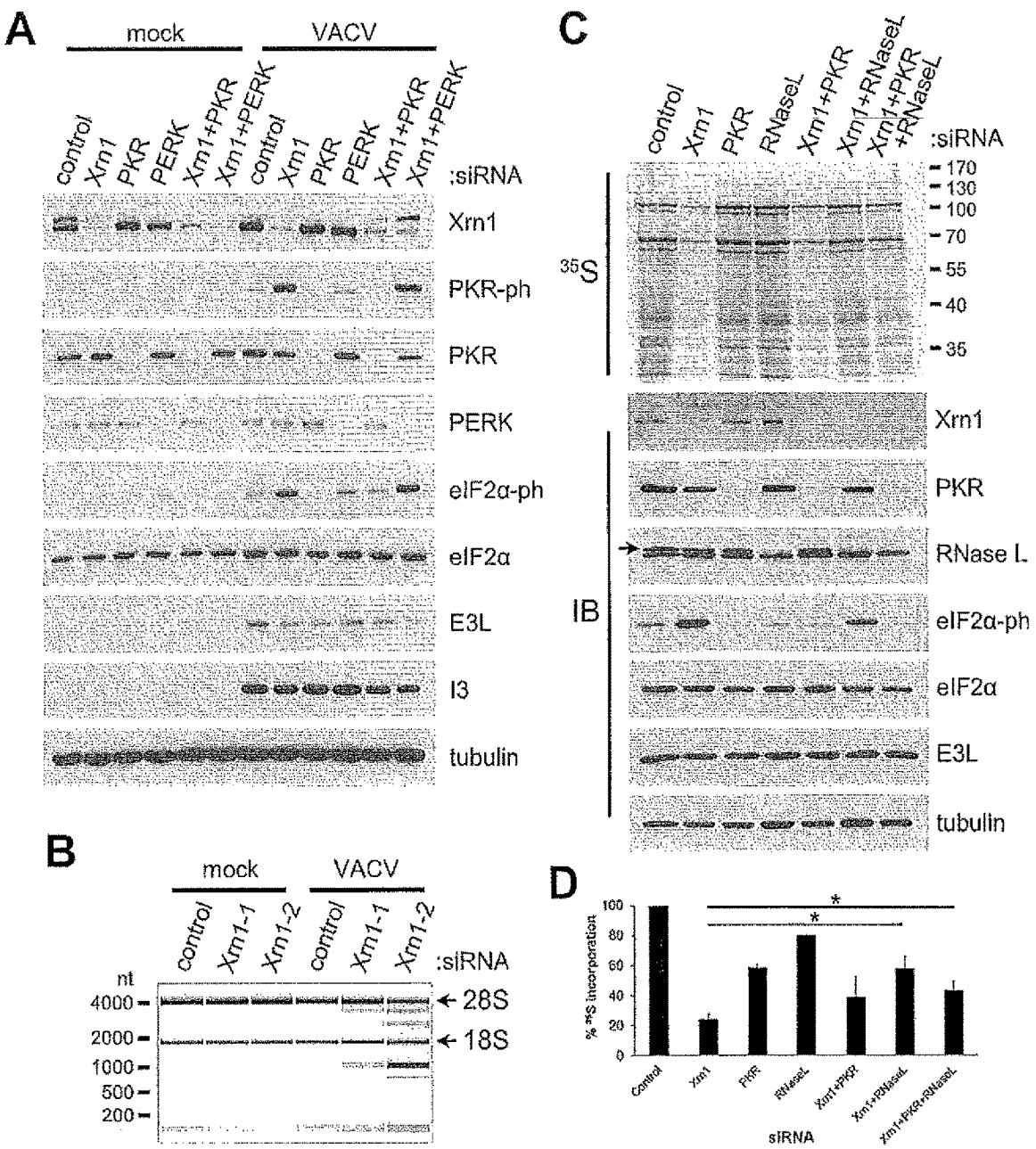
FIG. 4A-4D. PKR-dependent eIF2α phosphorylation and RNase L-mediated rRNA degradation in Xrn1-depleted cells infected with VacV. (4A) NHDFs transfected with the indicated siRNAs were mock-infected or infected with VacV (MOI=5). Total protein was collected at 18 hpi and analyzed by immunoblotting with the indicated antibodies. Tubulin served as a loading control. (4B) NHDFs transfected with the indicated siRNAs were mock-infected or infected with VacV (MOI=5). At 18 hpi, total RNA was isolated and analyzed (4C) NHDFs transfected with the indicated siRNAs were infected as in (4A). At 18 hpi, cells were metabolically pulse-labeled with [$^{35}$S]Met-Cys for 30 min. Total protein was collected, separated by SDS-PAGE and [$^{35}$S]-labeled proteins visualized by exposing the fixed, dried gel to X-ray film. Molecular mass standards (in KDa) are shown to the right (upper panel). The same lysates were also immunoblotted (IB) with the indicated antibodies (lower panel). The RNase L-specific immunoreactive band is indicated by an arrow. Tubulin served as a loading control. (4D) metabolically radiolabeled samples from 4C together with two additional independent replicate experiments were TCA precipitated. [$^{35}$S] incorporation into newly synthesized proteins was quantified by liquid scintillation counting. Means are plotted ±SEM. * indicates P≤0.05 by paired students t-test compared to Xrn1 siRNA-treated cells. See also FIGS. 9 and 10.

Example 5: Activation of PKR and RNase L is Restricted by Xrn1 in VacV-Infected Cells Of the four known mammalian eIF2α kinases that control translation in response to discrete stress, PKR, PERK, and GCN2 possess documented anti-viral activity while only one, PKR, is encoded by an interferon-induced gene (Walsh et al., 2013). Importantly, although the inhibition of translation in Xrn1-depleted NHDFs infected with VacV correlated with PKR activation (FIG. 2B), both PKR and PERK activities are antagonized by VacV-encoded effectors (Walsh et al., 2013). To determine which of these kinases might be required for eIF2α phosphorylation in Xrn1-depleted, VacV-infected NHDFs, each was depleted by RNAi in NHDFs treated with control ns or Xrn1-specific siRNA. While little detectable change in eIF2α phosphorylation was observed in mock-infected cells, only depleting the dsRNA-activated eIF2α kinase PKR reduced phosphorylated eIF2α levels in Xrn1-depleted, VacV-infected cells and basal phosphorylated eIF2α levels observed in VacV-infected, control ns siRNA-treated NHDFs (FIG. 4A). In addition, PKR activation above basal levels present in control, ns siRNA-treated cultures was readily detected in Xrn1-depleted NHDFs (FIG. 4A). In contrast, depletion of PERK, a distinct eIF2α kinase activated in response to unfolded protein accumulation in the ER, did not detectably reduce eIF2α phosphorylation in Xrn1-depleted cells and acted as a negative control (FIG. 4A).

Besides PKR, 2'-5' oligoadenylate synthetases (OAS) are also encoded by a family of interferon-stimulated genes and are components of a separate arm of host dsRNA-dependent innate defenses. The resulting 2'-5' oligoadenylate chains produced by OAS in response to dsRNA in turn selectively activate RNase L, an endonuclease that indiscriminately cleaves mRNAs and ribosomal RNA (rRNA) to inactivate ribosomes and inhibit protein synthesis (Sadler and Williams, 2008). To determine if RNase L was activated in Xrn1-depleted NHDFs infected with VacV, total RNA isolated from mock vs VacV-infected NHDFs treated with control ns or either Xrn1 siRNA was analyzed using a Bioanalyzer Nano LabChip. While Xrn1-depletion resulted in little detectable difference in rRNA abundance in mock-infected cells, 28S and 18S rRNA breakdown products were only detected in VacV-infected NHDFs treated with Xrn1 specific compared to control ns siRNA (FIGS. 4B; 9). Thus, two dsRNA-activated innate immune defense pathways are specifically stimulated upon VacV infection of Xrn1-depleted cells. This shows that Xrn1 is required to restrict the activity of both the eIF2α kinase PKR and RNase L, which is activated by the dsRNA-responsive OAS.

Figure 10:
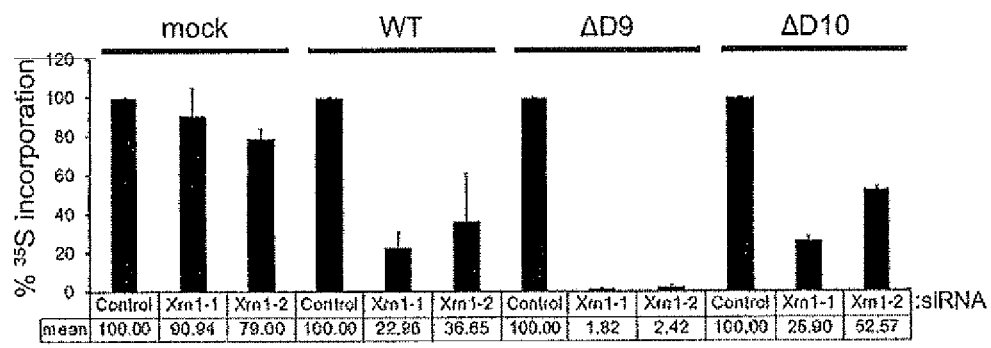
FIG. 10. PKR-dependent eIF2α phosphorylation and RNase L-mediated inhibition of protein synthesis in Xrn1-depleted cells infected with VacV, related to FIG. 4. NHDFs transfected with the indicated siRNAs were mock-infected or infected with VacV (MOI=5). At 22 hpi, cells were metabolically pulse-labeled with [$^{35}$S]Met-Cys for 30 min. Total protein was collected, separated by SDS-PAGE and [$^{35}$S]-labeled proteins visualized by exposing the fixed, dried gel to X-ray film. Molecular mass standards (in kDa) are shown to the right. (Upper panel). The same lysates were also immunoblotted (IB) with the indicated antibodies (Lower panel). The RNase L-specific immunoreactive band is indicated by an arrow. Tubulin served as a loading control.

To determine the relative contribution of RNAse L and/or PKR to the global inhibition of translation in Xrn1-depleted NHDFs upon VacV-infection, the capacity of RNAse L or PKR knockdown to prevent the inhibition of protein synthesis in Xrn1-depleted cells infected with VacV was evaluated. While infected cell protein synthesis was similar in cultures treated with control, ns siRNA or siRNAs specific for PKR or RNase L, the inhibition of translation associated with Xrn1-knockdown was most effectively suppressed by co-depletion of RNase L (FIG. 4C, 4D). Furthermore, knockdown of both Xrn1 and RNase L reduced phosphorylated eIF2α abundance compared to cultures treated with Xrn1 siRNA alone (FIG. 4C, 4D). Triple depletion of Xrn1, RNase L and PKR reduced phosphorylated eIF2α levels to below those observed in cultures treated with control ns siRNA, demonstrating the involvement of the eIF2α kinase PKR (FIG. 4C, 4D). This did not, however, detectably augment protein synthesis beyond levels observed in Xrn1-RNase L doubly depleted cultures. Surprisingly, co-depletion of Xrn1 and PKR at best only modestly increased [$^{35}$S]-amino acid incorporation into protein despite its efficacy at reducing phosphorylated eIF2α abundance below levels observed in VacV-infected cultures treated with control ns siRNA (FIG. 4C). This is a consequence of sustained RNase L activation, which destroys both mRNA and rRNA and would be expected to restrict protein synthesis even though eIF2 activity is preserved. Equivalent results were obtained using a different Xrn1-specific siRNA (FIG. 10). Taken together, these results show that the observed inhibition of protein synthesis in Xrn-depleted cells results primarily from activation of RNase L.

Example 6: Control of dsRNA Accumulation in VacV-Infected Cells by Xrn1

Figure 5:
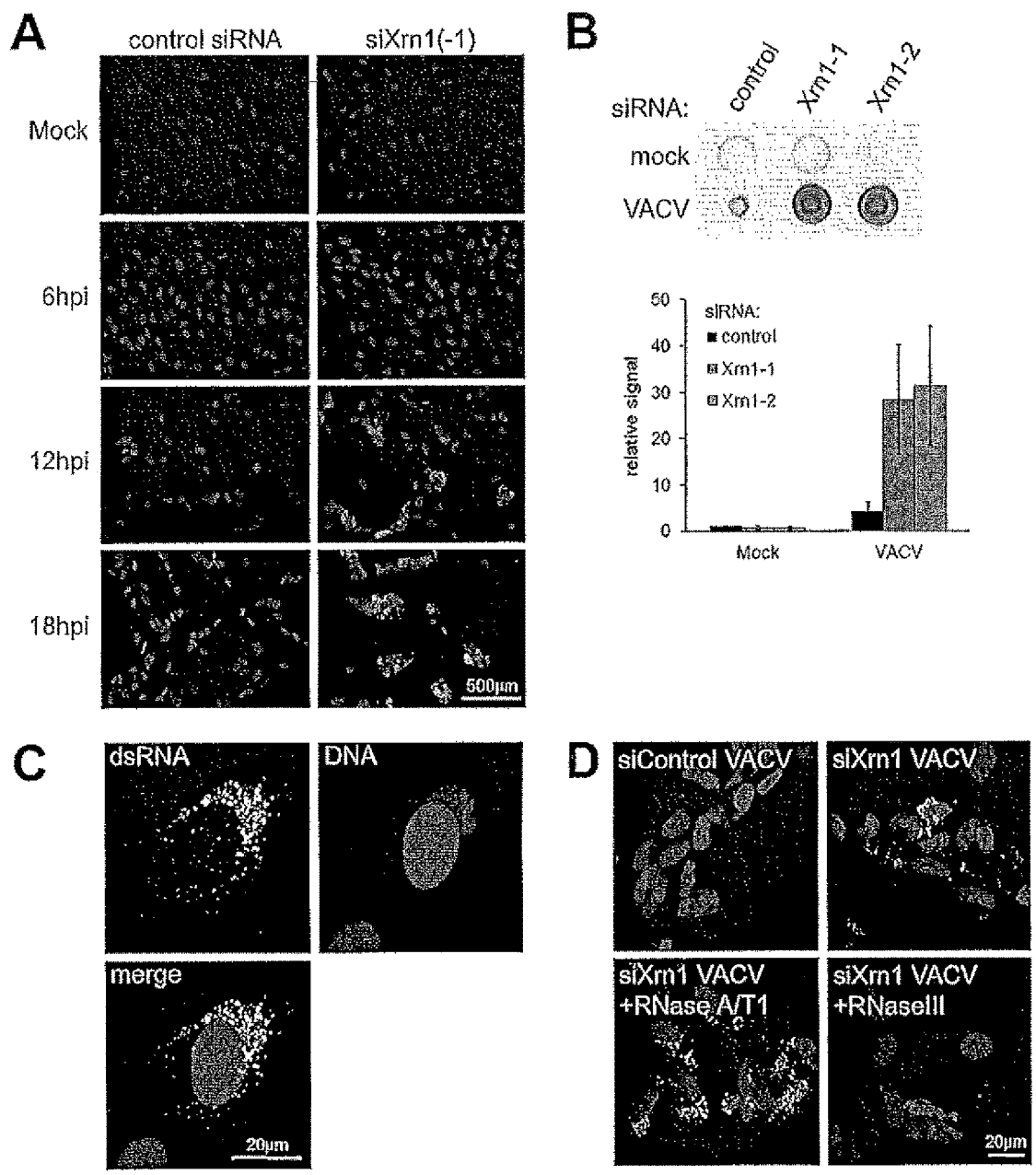
FIG. 5A-5D. Massive dsRNA accumulation in Xrn1-depleted cells infected with VacV. NHDFs transfected with the indicated siRNAs were mock-infected or infected with VacV (MOI=5). Cells were fixed at 6, 12, and 18 hpi and stained for immunofluorescence with J2 anti-dsRNA antibody (green). DNA was stained using DAPI (blue). (5A) Cells were visualized using fluorescence microscopy with a 20× objective. (5B) NHDFs treated with siRNAs and infected as in (5A) were harvested and cell free lysates prepared at 18 hpi. Equal volumes of lysates were dotted onto membrane and dsRNA detected by Immunoblotting (upper panel). The dsRNA signal from 5B together with two independent replicates was quantified and the means plotted ±SEM (lower panel). (5C) Confocal image of Xrn1 siRNA-treated, infected cells from 5A, fixed at 18 hpi using 63× objective. (5D) Xrn1 siRNA-treated, infected cells fixed at 18 hpi were treated with a mixture of single strand-specific RNase A/T1, dsRNA-specific RNase III or buffer alone prior to immunostaining of dsRNA.

Since dsRNA-responsive host defense proteins were activated in Xrn1-depleted, VacV-infected NHDFs, this demonstrated that overall steady-state dsRNA levels are greater in VacV-infected cells. To test this possibility, control, ns siRNA-treated and Xrn1-depleted NHDFs were mock-infected or infected with VacV. At different times post-infection, cultures were fixed and processed for indirect immunofluorescence using a monoclonal antibody that specifically detects dsRNA. Unlike earlier studies that detected dsRNA in VacV-infected cells with this antibody (Weber et al., 2006), the fluorophore signal was visualized without using tyramide signal amplification. By 12 hpi, cells containing elevated levels of dsRNA were readily detected in Xrn1-depleted NHDFs infected with VacV vs NHDFs treated with control, ns siRNA (FIG. 5A). The fraction of dsRNA-containing VacV-infected cells increased through 18 hpi for cultures treated with Xrn1 siRNA compared to control ns siRNA (FIG. 5A). This was confirmed by immuno dot-blotting on immobilized cytoplasmic extracts (FIG. 5B). Furthermore, dsRNA specific staining was consistently most intense coincident with DAPI-staining cytoplasmic compartments (FIG. 5C), showing that dsRNA accumulation is occurring specifically within viral replication compartments.

Figure 6:
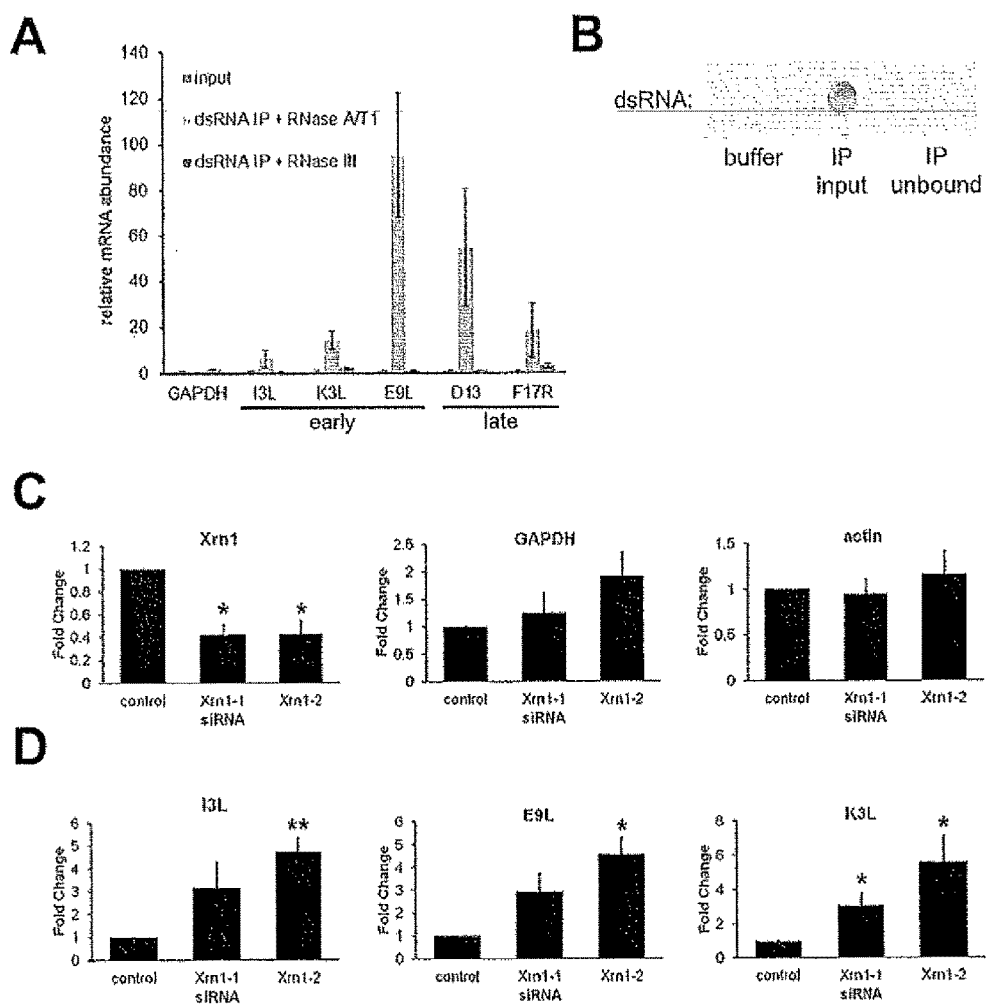
FIG. 6A-6D. Elevated viral mRNA abundance and their enrichment in dsRNA isolated from Xrn1-depleted, VacV-infected cells. Cell free lysates from NHDFs transfected with Xrn1-1 siRNA and infected with VacV (MOI=5) were prepared at 22 hpi and immunoprecipitated using J2 anti-dsRNA antibody. After treating with RNase A/T1 or RNase III, isolated RNA was analyzed by RT-qPCR using the indicated viral or cellular mRNA primers. mRNA abundances were normalized to actin and calculated relative to input (set to 1). The means of three independent experiments were plotted ±SEM. (6B) Equal volumes of buffer, input lysate (IP input), or the unbound fraction (IP unbound) were dotted onto a membrane and dsRNA detected by immunoblotting to demonstrate dsRNA depletion in the unbound fraction. (6C, 6D) NHDFs were treated with the indicated siRNAs and RNA isolated from uninfected cells (6C) or 3 hpi with VACV (MOI=5) (6D). RNA was subject to RT-qPCR analysis for the indicated cellular or early viral mRNAs and each reaction product normalized to 18S rRNA and presented as the fold change relative to control siRNA-treated cells. The means of 3 independent experiments are plotted ±SEM. A significant difference by paired students t-test compared to control siRNA treated cells is indicated by * (P≤0.05) or ** (P≤0.01).
Figure 9:
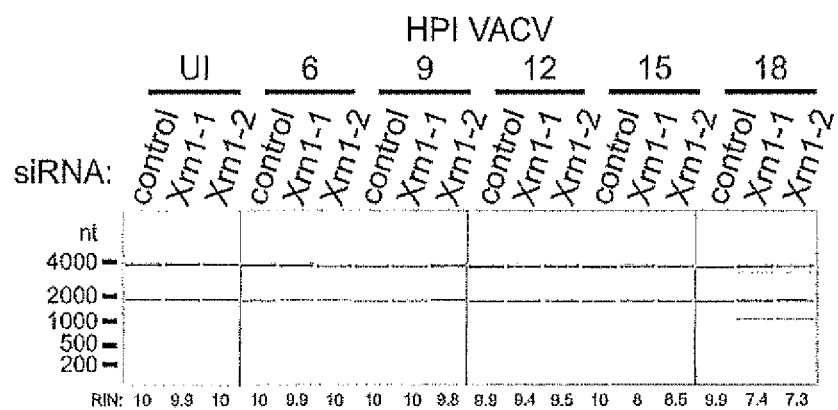
FIG. 9. rRNA degradation in Xrn1-depleted cells infected with VacV, related to FIG. 4. NHDFs transfected with ns control or Xrn1-specific siRNAs were infected with VacV (MOI=5). At the indicated times (hpi) cells were lysed and RNA isolated. Uninfected (UI) samples were collected at 0 h. RNA was then analyzed on a Bioanalyzer Nano LabChip. RNA integrity (RIN) values calculated by Agilent Bioanalyser 2100 Expert software are displayed below.

To verify that the immunoreactive signal was indeed due to dsRNA, fixed permeabilized cells were treated with either the single strand specific ribonucleases A and T1 or the dsRNA specific RNase III. FIG. 5D shows that dsRNA immunoreactivity in Xrn1-depleted NHDFs infected with VacV was insensitive to RNAse A/T1 digestion, but abolished by pre-treatment with RNase III, indicating that this immunostaining is in fact specific for dsRNA. Immunopurification of dsRNA revealed enrichment for selected viral early and late mRNAs, but not two representative host mRNAs (actin, GAPDH). While this enrichment was readily observed in preparations treated with single-strand ribonucleases A and T1, it was eliminated upon treatment with the dsRNA specific nuclease RNase III (FIG. 6A, 6B). This shows that dsRNA accumulating in VacV replication compartments contains virus-encoded mRNAs, although the possibility that cellular mRNAs may also be represented cannot be excluded. While overall actin and GAPDH mRNA levels remain relatively constant in Xrn1-depleted, VacV-infected NHDFs, the abundance of representative viral early mRNAs increased significantly (FIG. 6C, 6D). Activation of RNase L late in infection (FIG. 9) precluded analysis of how late VacV mRNA abundance is influenced by Xrn1-depletion. This is consistent with i) a mechanism whereby the host 5-3' mRNA exoribonuclease Xrn1 restricts dsRNA accumulation by accelerating viral mRNA turnover; and ii) the possibility that the dsRNA originates from the products of overlapping VacV transcription units on opposite DNA strands.

Example 7: Regulation of the Response to Exogenous dsRNA in Uninfected Cells by Xrn1

Figure 7:
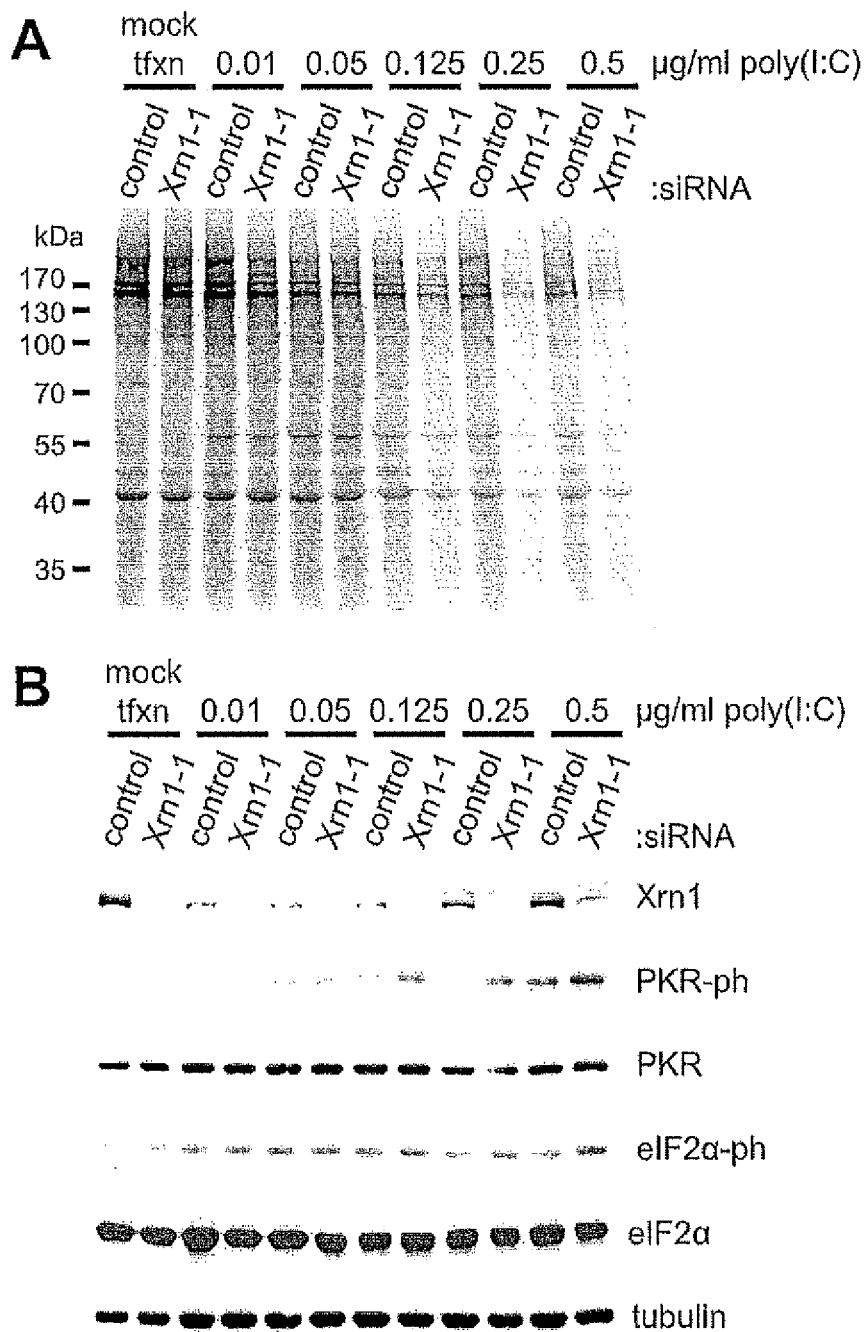
FIGS. 7A and 7B. Increased sensitivity to the dsRNA analog poly (I:C) in response to Xrn1-depletion in uninfected cells. NHDFs treated with the indicated siRNAs were mock-transfected or transfected with increasing amounts of poly (I:C). After 3 h, cells were metabolically pulse-labeled with [$^{35}$S] Met-Cys for 30 min. Total protein was collected, separated by SDS-PAGE, and [$^{35}$S]-labeled proteins directly visualized by exposing the fixed, dried gel to X-ray film. Molecular mass standards (in kDa) are shown to the left (7A). The same lysates were also immunoblotted with the indicated antibodies (7B). Tubulin served as a loading control. See also FIG. 11.
Figure 11:
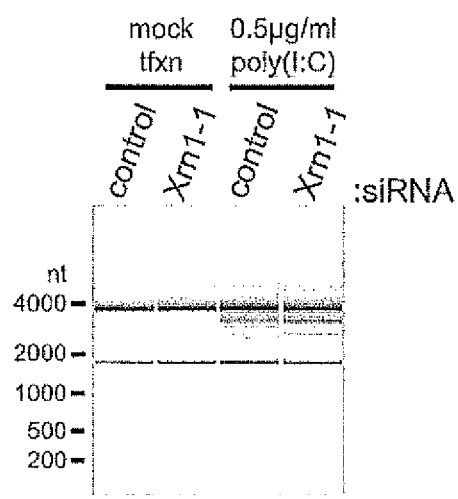
FIG. 11. rRNA degradation in Xrn1-depleted cells transfected with poly (I:C), related to FIG. 7. NHDFs treated with the indicated siRNAs were mock-transfected or transfected with 0.5 µg/ml poly (I:C). At 3 hpi cells were lysed and RNA isolated and analyzed on a Bioanalyzer Nano LabChip.

The accumulation of dsRNA in Xrn1-depleted NHDFs infected with VacV raised the possibility that Xrn1 might regulate dsRNA responsiveness in uninfected cells and naturally buffer dsRNA accumulation. To investigate the impact of Xrn1-depletion on dsRNA responsiveness of uninfected cells, NHDFs treated with control ns or Xrn1-specific siRNA were transfected with increasing amounts of synthetic poly(I:C) dsRNA and rates of protein synthesis were evaluated. While reductions in the intensity of individual protein bands were detected in Xrn1-depleted NHDFs exposed to 0.01-0.05 µg/ml poly (I:C) compared to NHDFs treated with control ns siRNA, global protein synthesis in Xrn1-depleted NHDFs exposed to poly (I:C) concentrations of 0.125 µg/ml and greater was significantly inhibited by poly (I:C) compared to corresponding controls (FIG. 7A). The reduction in ongoing mRNA translation in Xrn1-depleted NHDFs in response to poly (I:C) was mirrored by greater amounts of activated PKR and phosphorylated eIF2α compared to cultures treated with control ns siRNA (FIG. 7B). However, while rRNA breakdown products were observed in poly (I:C)-treated cultures, further increase upon Xrn1-depletion was not detected (FIG. 11). This indicates differences in how infected vs uninfected NHDFs respond to Xrn1-depletion or reflects technical limitations in the assay. Nevertheless, the cellular 5'-3' mRNA exonuclease unexpectedly control the host response to exogenous dsRNA, an important pathogen associated molecular pattern capable of activating potent innate defenses, in uninfected primary human cells.

Example 8: Treatment of a Patient Harboring a Malignant Tumor with the VacV of the Present Invention Patients with advanced hepatocellular carcinoma (HCC), are treated with the oncolytic decapping-deficient VacV mutants of the present invention. The patients are treated by directly injecting $10^9$ pfu of the virus into the tumors using a 21 gauge needle once per week over a 6-10 week period. The tumors are injected with virus-containing solution whose volume is equivalent to approximately 25% of the total volume of the tumor spaced at approximately 1 cm intervals.

It is expected that patients receiving the virus will experience a significant reduction in their tumor burden.

Figure 12:
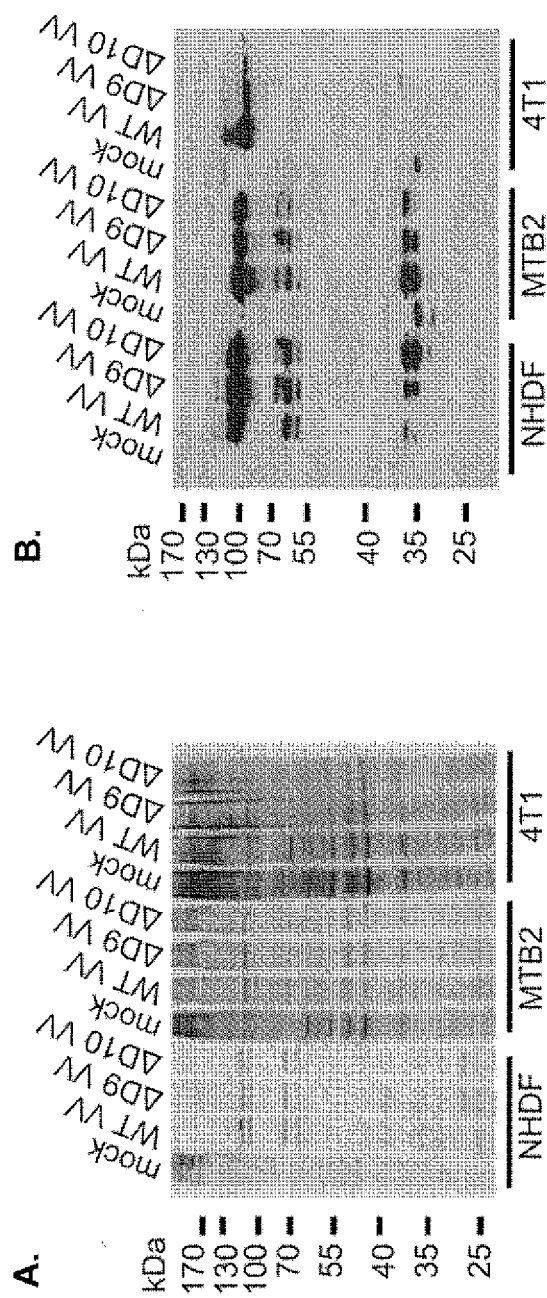
FIG. 12A-12B. Protein synthesis and accumulation in murine cancer cells infected with D9 or D10-deficient VACV. A.) Murine MBT2 bladder carcinoma, murine 4T1 breast carcinoma, or normal human fibroblasts were mock-infected (mock) or infected (MOI=3) with WT VACV, D9-deficient VACV (ΔD9) or D10-deficient VACV (ΔD10). At 18 hpi, cells were metabolically pulse labeled with [$^{35}$S]Met-Cys for 30 min. Total protein was collected, separated by SDS-PAGE and [$^{35}$S]-labeled proteins visualized by exposing the fixed, dried gel to X ray film. Molecular mass standards (in kDa) are shown on the left. B.) Samples in A. were analyzed by immunoblotting using anti-VACV polyclonal antisera.

Example 9: Decapping-Deficient VACV Replicates Similar to Wild-Type VACV in Murine Cancer Cells D10-deficient VACV recombinants (a single D10 mutation or a doubly-deficient D9/D10) were attenuated in mice relative to a D9-deficient mutant (Liu et al., 2014, 2015). To evaluate the capacity of the decapping-deficient VACV mutants to replicate in murine tumor cell lines, MBT2 murine bladder carcinoma and 4T1 murine breast carcinoma were infected with either WT VacV, D9-deficient (ΔD9) VacV, or D10-deficient (ΔD10) VACV (MOI=3). After 18 h, cultures were metabolically radiolabeled with [$^{35}$S] amino acids for 1 h. Total protein was subsequently harvested, fractionated by SDS PAGE and analyzed by autoradiography (FIG. 12A) or immunoblotting (FIG. 12B). Compared to control human fibroblasts (NHDFs), less virus-induced suppression of ongoing host cell protein synthesis (host cell shutoff) was observed in cells infected with either WT, D9, or D10-deficient VACV (FIG. 12A). Notwithstanding the absence of detectable host cell shut-off, VACV proteins accumulated to similar levels in 4T1 or MBT2 cells infected with either WT, D9, or D10-deficient VACV (FIG. 12B). Thus, viral proteins accumulate similarly in murine cancer cell lines infected with decapping-deficient VACVs lacking either the D9 or D10 genes compared to WT VACV.

Figure 13:
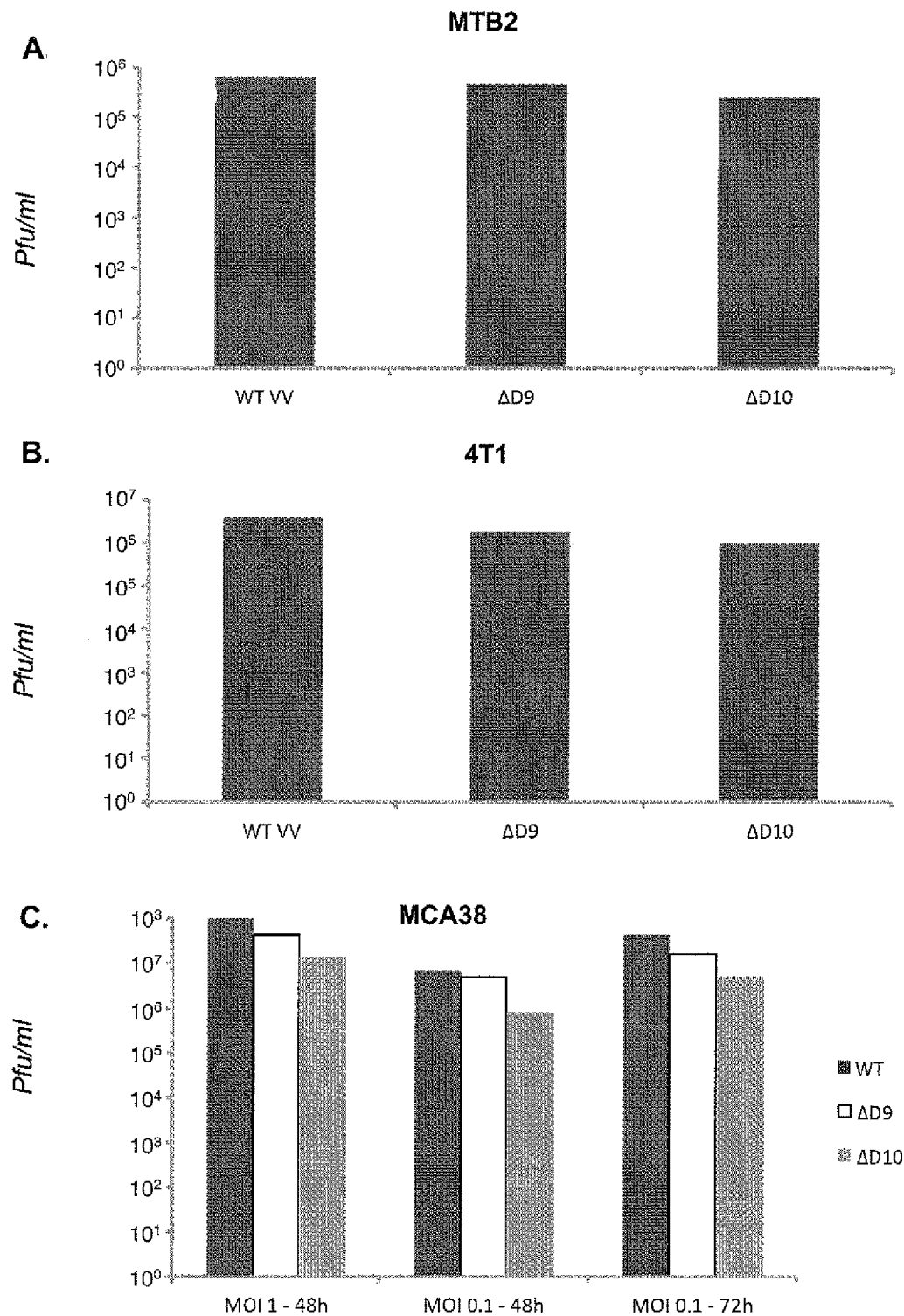
FIG. 13A-13C. Replication of VACV D9 and D10-deficient mutants in murine cancer cells. Murine bladder carcinoma cells (A) or murine 4T1 breast carcinoma cells (B) seeded in 12 well dishes (approx. $5 \times 10^5$ cells/well) were infected (300 pfu/well) with either WT VACV, D9-deficient VACV (ΔD9) or D10-deficient VACV (ΔD10). After 48 h, cultures were lysed by freeze thawing and the amount of infectious virus quantified by plaque assay in BSC40 cells. (C) As in (A) and (B) except murine MCA38 adenocarcinoma cells were infected at either MOI=1 ($5.5 \times 10^5$ pfu) or MOI=0.1 ($5.5 \times 10^4$ pfu). At the indicated times post-infection, cultures were lysed and infectious virus quantified as in (A) and (B).

To compare the capacity of decapping-deficient VACV to lytically replicate in and kill murine cancer cell lines, MBT2 bladder carcinoma or 4T1 breast carcinoma cells were infected with either WT, D9, or D10-deficient virus at low MOI (FIG. 13A,B). After 48 h, cell free lysates were prepared by freeze thawing and the amount of infectious virus produced quantified by plaque assay in permissive BSC40 cells. In both MBT2 or 4T1 mouse cancer cell lines, decapping deficient VACV mutants grew to similar levels as WT VACV, with only a minor reduction in yield (no more than 4-fold) detected in cells infected with either D9 or D10-deficient viruses. Lytic replication was evaluated in an additional murine cancer cell line, MCA38 colon adenocarcinoma (FIG. 13C). Similar to findings in 4T1 and MBT2, decapping deficient VAV mutants replicated to a similar extent as WT virus. Thus, decapping deficient VACV are nearly as proficient as WT VACV in lytically replicating in representative murine cancer cell lines derived from different mouse genetic backgrounds and can be tested for their oncolytic capacity in mouse tumors.

Example 10: VACV Decapping-Deficient Mutants Display Oncolytic Virus Anti-Tumor Activity in Immunocompetent Murine Models To determine if decapping-deficient VACV lacking D9 or D10 have oncolytic virus activity, subcutaneous tumors were established in syngeneic mice prior to mock treatment with D9 or D10-deficient VACV. 4T1 cells (1x $10^4$) in DMEM without additives were injected sc into the right flank of 8 week old, female BALB/c mice anesthetized by ip injection of Ketamine (100 mg/Kg) and Xylazine (10 mg/Kg). Tumor growth was monitored every day using an electronic digital caliper and tumor volume calculated as described (Demaria et al., 2005). When tumors reached approximately 50 mm$^3$ (8-9 days after 4T1 inoculation), they were directly injected on days 0, 3 and 6 with $5.4 \times 10^6$ pfu of D10-deficient VACV (N=10 mice) or an equivalent virus-free control preparation from uninfected cells (N=10 mice). Tumor size was monitored over time and animals were euthanized when control-treated tumors reached approximately 1200 mm$^3$.

Figure 14:
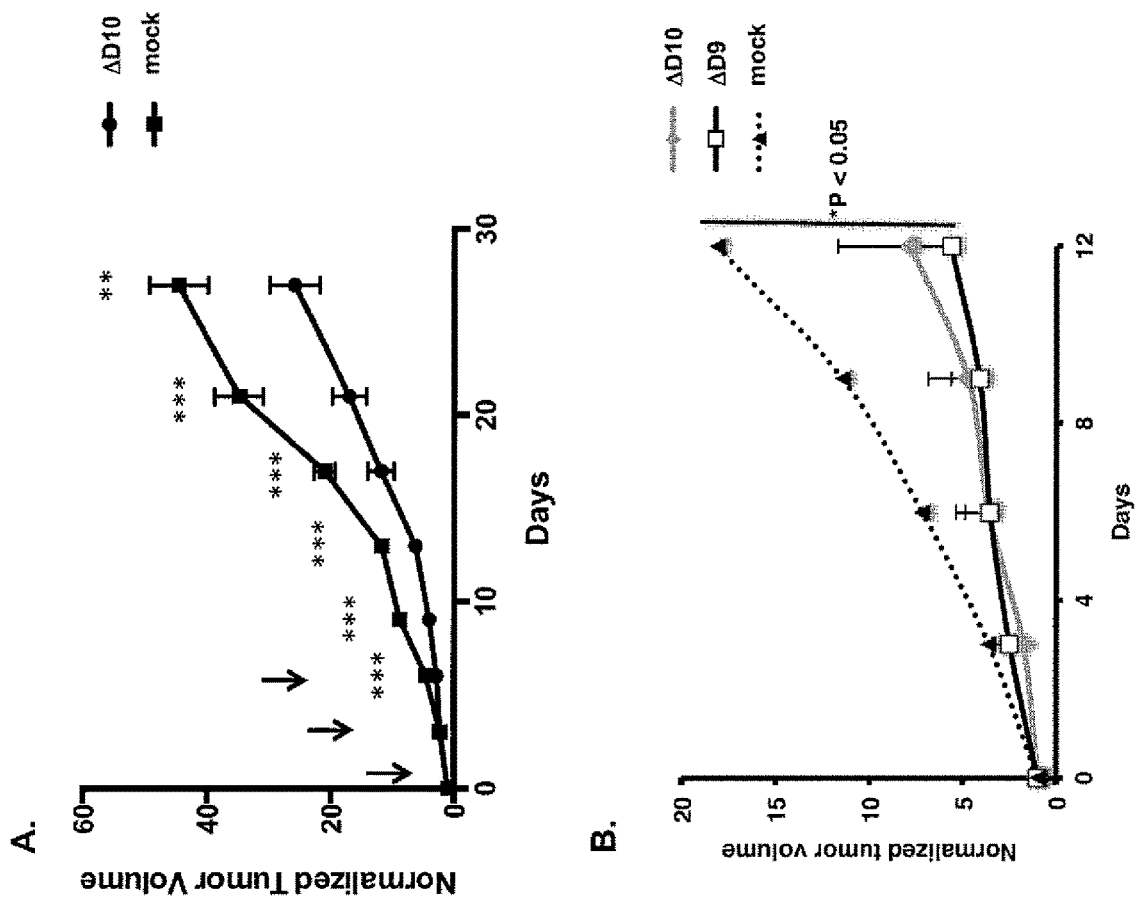
FIG. 14A-14B. Anti-tumor activity of VACV D9 and D10-deficient mutants in murine cancer cells. A.) Murine 4T1 breast carcinoma cells ($1 \times 10^4$) in DMEM without additives were injected subcutaneously (sc) into the right flank of 8 week old, female BALB/c mice anesthetized by ip injection of Ketamine (100 mg/Kg) and Xylazine (10 mg/Kg). Tumor growth was monitored every day using an electronic digital caliper and tumor volume calculated as described (Demaria et al., 2005). When tumors reached approximately 50 mm$^3$ (8-9 days after 4T1 inoculation), they were directly injected on days 0, 3 and 6 (indicated by downward pointing arrows) with $5.4 \times 10^6$ pfu of D10-deficient (ΔD10) VACV (N=10 mice) or an equivalent virus-free control preparation (Mock) from uninfected cells (N=10 mice). Tumor size was monitored over time and animals were euthanized when control-treated tumors reached approximately 1200 mm$^3$. Error bars indicate standard error of the mean (SEM). P-values were obtained by multiple T-test. *P<0.001; P<0.01. B.) As in (A) except murine MCA38 colon adenocarcinoma cells ($1 \times 10^5$) were injected sc into the flank of 4-6 week old, female C57/Bl6 mice. When tumors reached approximately 50 mm$^3$ (approx. 7 days after MCA38 inoculation), they were directly injected on days 0, 3 and 6 with $1.0 \times 10^6$ pfu of D10-deficient (ΔD10) VACV (N=10 mice), $1.0 \times 10^6$ pfu of D9-deficient (ΔD9) VACV (N=10 mice), or an equivalent virus-free control preparation from uninfected cells (N=10 mice). Tumor size was monitored over time and animals were euthanized when control-treated tumors reached approximately 1200 mm$^3$. Between days 9-12, three mice died in the mock-treated group, two mice died in the ΔD10-treated group, and one mouse died in the ΔD9-treated group. Error bars indicate standard error of the mean (SEM). P-values were obtained by multiple T-test. *P<0.05.

Between 6-9 days post-treatment, a statistically significant difference between mock and ΔD10-treated tumors was readily observed (FIG. 14A). The volume of mock-treated tumors increased to a greater extent and more rapidly than ΔD10-treated tumors. This difference increased and persisted through the entire time course of the experiment (FIG. 14A). This establishes that VACV treatment has anti-tumor activity against 4T1 tumors in syngeneic Balb/c mice and demonstrates that decapping-deficient VACV, such as ΔD10, are effective oncolytic viruses.

To evaluate the anti-tumor activity of decapping deficient VACV in a different murine genetic background, an MCA38 model in C57/Bl6 mice was utilized. MCA38 murine adenocarcinoma cells in media were injected ($1 \times 10^5$) subcutaneously into the flank of 4-6 week old, female C57/Bl6 mice. When tumors reached approximately 50 mm$^3$ (approx. 7 days after MCA38 inoculation), they were directly injected on days 0, 3 and 6 with $1.0 \times 10^6$ pfu of D10-deficient (ΔD10) VACV (N=10 mice), $1.0 \times 10^6$ pfu of D9-deficient (ΔD9) VACV (N=10 mice), or an equivalent virus-free control preparation from uninfected cells (N=10 mice). Tumor size was monitored over time and animals were euthanized when control-treated tumors reached approximately 1200 mm$^3$.

By 6 days post-treatment, a statistically significant difference between mock and ΔD9 or ΔD10-treated tumors was readily observed (FIG. 14B). The volume of mock-treated tumors increased to a greater extent and more rapidly than ΔD9 or ΔD10-treated tumors. This difference increased and persisted through entire time course of the experiment (FIG. 14B). This establishes that D9 or D10-deficient VACV treatment has anti-tumor activity against MCA38 tumors in syngeneic C57/Bl6 mice and demonstrates that a decapping-deficient VACV lacking either D9 or D10 decapping enzymes are effective oncolytic viruses. In addition, this activity is not limited to a particular murine genetic background. The MCA38A tumors were much more aggressive, progressing more rapidly than 4T1 as evidenced by the death of 3 mice treated with the virus-free control preparation. This may reflect the greater dose of cells used to seed the tumor in these experiments. The rapid growth of the tumors necessitated that the animals be euthanized on day 12, effectively ending the experiment. While one mouse died in the ΔD9-treated group and two mice died in the ΔD10-treated group, the fatalities in each experimental group were less than the control group treated with a virus-free preparation.

Example 11: Preferential Replication of D9 or D10 Decapping-Deficient VACV in Human Tumor Cells Compared to Non-Tumorigenic Cells To determine if replication of D9 or D10 decapping-deficient VACVs was preferentially restricted in non-tumorigenic human cells compared to tumor cells, the activation state of the Interferon-induced, double-strand RNA (dsRNA) dependent protein kinase PKR was investigated. PKR is an interferon-induced host gene that is activated by dsRNA, a pathogen associated molecular pattern (PAMP) that accumulates in virus-infected cells and is a signature of virus infection. Upon activation, PKR phosphorylates the host translation initiation factor eIF2 on its alpha subunit, inactivating this critical translation initiation factor and restricting virus protein synthesis and replication (reviewed by Mohr & Sonenberg, 2012). PKR activation is routinely measured by immunoblotting for the phosphorylated form using a T446 phospho-specific anti-PKR antibody (for example see Burgess & Mohr, 2015).

Figure 15:
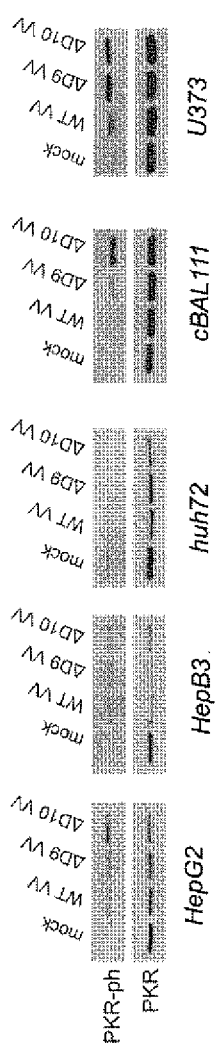
FIG. 15. Activation of cell intrinsic anti-viral defenses in untransformed, non-tumorigenic human cells following infection with D9 or D10-deficient VACV. Human hepatocarcinoma (HepG2, HepB3, Huh7), malignant glioma (U373), or untransformed, non-tumorigenic cBAL111 human liver cells were either mock-infected or infected (MOI=3) with WT VACV, D9-deficient VACV (ΔD9) or D10-deficient VACV (ΔD10). After 18 h, total protein was isolated and analyzed by immunoblotting with either total PKR or a PKR T446 phospho-specific antibody (cat #32036; Abcam) as described (Burgess & Mohr, 2015)

Following mock-infection or infection with ΔD9, ΔD10, or WT VACV (at high MOI) in a variety of tumorigenic human hepatocarcinoma cell lines (HepG2, HepB3, Huh7) or a human malignant glioma cell line (U373), the overall abundance of total PKR and phosphorylated (activated) PKR were measured by immunoblotting. In HepG2, Heb3B, and U373 cells, infection with WT, ΔD9 or ΔD10 activated PKR, as evidenced by phosphorylated PKR levels, was similarly above levels detected in mock-infected cells (FIG. 15). While a background level of activated PKR was detected in mock-infected Huh 7 cells, activated PKR abundance was reduced similarly upon infection with WT, ΔD9, or ΔD10 VACV (FIG. 15). Thus, in tumorigenic human cell lines, PKR was not detectably hyperactivated following infection with ΔD9 or ΔD10 VACV compared to WT VACV.

To compare PKR activation upon infection of non-tumorigenic cells with WT, ΔD10 or ΔD10 VACV, cBAL111 cells were either mock-infected or infected. The cBAL111 cell line was derived from human fetal liver cells that were immortalized by overexpressing the telomerase reverse transcriptase (Deurholt et al. 2009). These cells display hepatic functionality similar to the parental cells prior to immortalization, expressing immature hepatocyte markers, including glutathione S transferase, cytokeratin 19, CD146 (progenitor cell marker), and produce urea, albumin and cytokeratin 18 (Deurholt et al. 2009). They eliminate galactose and are negative for lidocaine elimination.

When transplanted in the spleen of immunodeficient mice, cBAL111 engrafted into the liver and partly differentiated into hepatocytes showing expression of human albumin and carbamoylphosphate synthetase without signs of cell fusion (Deurholt et al. 2009). Significantly, cBAL111 cells did not grow in soft agar and were not tumorigenic in nude mice (Deurholt et al. 2009). Remarkably, while phosphorylated PKR was not detected in mock infected or WT VACV-infected cBAL111 cells, activated, phosphorylated PKR was readily detected in cells infected with either ΔD9 or ΔD10 VACV (FIG. 15). This demonstrates that PKR is selectively hyperactivated upon infection with ΔD9 or ΔD10 decapping-deficient VACV, compared to WT VACV, in normal, non-tumorigenic cBAL111 cells. Moreover, it establishes that ΔD9 or ΔD10 decapping-deficient VACV hyperactivate cell intrinsic antiviral responses, like PKR, selectively in untransformed, non-tumorigenic, normal cells compared to tumorigenic cells. Since activated PKR is known to restrict virus protein production, viral protein accumulation, a vital marker for productive virus growth, will be restricted in normal cells infected with ΔD9 or ΔD10 decapping-deficient VACV compared to tumorigenic cancer cells.

To determine if VACV protein accumulation is restricted in normal, non-tumorigenic cells compared to tumor cells, cBAL111 and HepG2 cells were mock-infected or infected (MOI=0.01) with ΔD9 or ΔD10 decapping-deficient VACV and viral protein accumulation measured at 48 hpi by immunoblotting using total anti-VACV polyclonal sera.

Figure 16:
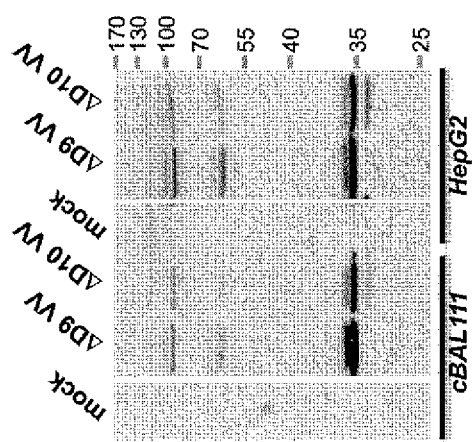
FIG. 16. Viral protein accumulation in untransformed, non-tumorigenic human cells vs. tumorigenic human cells infected with D9 or D10-deficient VACV. HepG2 human hepatocarcinoma cells or untransformed, non-tumorigenic c-BAL111 human liver cells were either mock-infected or infected (MOI=0.01) D9-deficient VACV (ΔD9) or D10-deficient VACV (ΔD10). After 48 h, total protein was isolated and total protein accumulation, which reflects virus growth and spread through the culture, analyzed by immunoblotting with anti-VACV polyclonal antisera.

FIG. 16 demonstrates VACV proteins accumulated to greater levels in tumorigenic HepG2 cells than in normal, non-tumorigenic cBAL111 cells 48 h post-infection with either ΔD9 or ΔD10 VACV. This establishes that ΔD9 or ΔD10 decapping-deficient VACV preferentially produce viral proteins in tumorigenic cancer cells compared to normal, non-tumorigenic cells, underscoring their predilection to preferentially replicate in cancer cells compared to normal cells. The restricted accumulation of viral proteins in normal, non-tumorigenic cells infected with ΔD9 or ΔD10 VACV reflects hyperactivation of these cell intrinsic host defenses like PKR and RNase L in normal cells, but not in cancer cells as shown in FIG. 15. Preferential production of viral proteins by ΔD9 or ΔD10 VACV in cancer cells compared to normal cells helps restrict virus replication and spread to cancer cells, a desirable feature for an oncolytic virus.

Significantly, OV efficacy and direct replication in treated tumors correlates strongly with viral protein production (Mohr 1996, Mulvey 1999, Taneja 2001; Mohr, 2005; Mohr & Mulvey, U.S. Pat. No. 7,731,952.). Indeed, restricting protein synthesis in virus-infected cells is a powerful host defense that inhibits virus replication by reducing protein accumulation and limits oncolytic virus replication (Mohr, 2005; Walsh & Mohr, 2004; 2011; Walsh et al, 2008; Burgess & Mohr 2015, this application FIG. 1). It is expected that oncolytic VACV deficient in D9 or D10 will preferentially replicate in tumorigenic cells like HepG2 compared to cBALL11, reflecting the enhanced accumulation of viral proteins in HepG2 compared to cBAL111 observed in FIG. 16.

In addition, HepG2 human hepatocarcinoma cells or untransformed, non-tumorigenic c-BAL111 human liver cells are either mock-infected or infected (MOI=0.01 or less) with a D9-deficient VACV (ΔD9), D10-deficient VACV (ΔD10), or a ΔD9/ΔD10 doubly deficient VACV. Cell free lysates are prepared by freeze thawing at 24, 36, and 48 hpi and the resulting amount of infectious VACV produced quantified by plaque assay in permissive BSC40 cells. It is expected that more infectious D9-deficient VACV (ΔD9) or D10-deficient VACV (ΔD10) will result from infecting tumorigenic cells like HepG2 than non-tumorigenic cBAL111, showing the preferential replication of ΔD9 and/or ΔD10 VACV as measured by infectious virus production in tumorigenic cells.

Example 12: VACV Decappin$_2$-Deficient Mutants Display Oncolytic Virus Anti-Tumor Activity in Human Tumor Xenografts in Athymic Mice To address the anti-tumor capacity of decapping-deficient VACV against human tumors, HepG2 hepatocellular carcinoma xenografts were established in the flanks of 8 week old, female, athymic (nude) mice. HepG2 human hepatocellular carcinoma cells in media were injected ($1\times10^7$) subcutaneously into the flank of athymic, Balb/c nude mice. When tumors reached approximately 50 mm$^3$ (approx. 7 days after HepG2 inoculation), they were directly injected on days 0, 3, 6 and 9 with $1.0\times10^6$ pfu of D10-deficient (ΔD10) VACV (N-10 mice), $1.0\times10^6$ pfu of D9-deficient (ΔD9) VACV (N=10 mice), or an equivalent virus-free control preparation from uninfected cells (N=10 mice). Tumor size was monitored over time.

Figure 17:
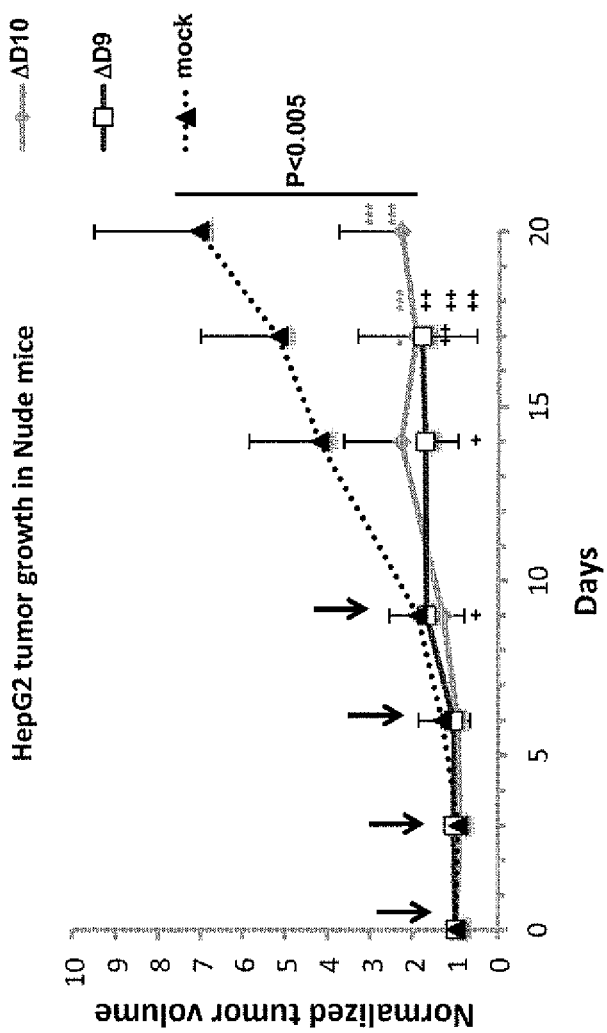
FIG. 17. Anti-tumor activity of VACV D9 and D10-deficient mutants in human tumor xenografts in immunocompromised mice. HepG2 human hepatocellular carcinoma cells in media were injected ($1 \times 10^7$) subcutaneously into the flank of 8 week old, female athymic, Balb/c nude mice. When tumors reached approximately 50 mm$^3$ (approx. 7 days after HepG2 inoculation), they were directly injected on days 0, 3, 6 and 9 (indicated by downward black arrows) with $1.0 \times 10^6$ pfu of D10-deficient (ΔD10) VACV (N-10 mice), $1.0 \times 10^6$ pfu of D9-deficient (ΔD10) VACV (N=10 mice), or an equivalent virus-free control preparation (Mock) from uninfected cells (N=10 mice). Tumor size was monitored over time. Error bars indicate standard error of the mean (SEM). P-value was obtained by multiple T-test (P<0.005). Day of death or euthanasia of individual mice is indicated by (+) for ΔD9-treated mice, (*) for ΔD10-treated mice. All mock treated mice were sacrificed on day 20.

A statistically significant difference between tumors treated with a virus-free "mock" preparation and ΔD9 or ΔD10-treated tumors was readily observed by day 14 (FIG. 17). The volume of mock-treated tumors increased to a greater extent and more rapidly than D10-treated tumors (FIG. 17). This difference increased and persisted through the entire 20 day time course of the experiment. This establishes that D9 or D10-deficient VACV treatment has anti-tumor activity against human HepG2 tumors in athymic, nude mice. Compared to the large tumors in mice treated with a control, virus-free preparation, mice treated with either D9 or D10-deficient viruses had at most small, palpable masses remaining and one had no palpable mass remaining.

While all the mice treated with a control, virus-free preparation survived until they were euthanized on day 20, 40% of the ΔD9-treated mice died by day 17, 40% of the ΔD10-treated mice died between day 17-18, and the remainder of the VACV-treated mice were euthanized (due to weight loss) on day 18 (ΔD9-treated) or day 20 (ΔD10-treated). Without wishing to be bound by theory it is believed that in athymic nude mice, the absence of the capacity to mount an acquired immune response accounts for the virulence of VACV deficient in only D9 or D10. Other VACV mutants that are attenuated in immunocompetent mouse models are likewise more virulent in athymic, immunocompromised mice, including multi-mutated strains being investigated in human trials as therapeutic oncolytic virus candidates (U.S. Pat. No. 7,208,313 B2).

In a further embodiment, D9 or D10-deficient virus are engineered to contain one or more additional mutations. This is achieved by using a VACV doubly-deficient in both D9 and D10 or by combining VACV deficient in producing functional D9 or D10 with loss of function mutations in other VACV genes to further curb virulence, including but not limited to VACV growth factor, VACV ribonucleotide reductase, VACV E3, VACV K3, or VACV tk (McCart et al., 2001; U.S. Pat. No. 7,208,313 B2; Fend et al., 2015; Kim et al., 2006; Thorne et al., 2007). This is also a strategy to retain VACV thymidine kinase function, which is often rendered non-functional in other VACV OVs (Buller et al., 1985; 1988; Gammon et al., 2010; Brandt & Jacobs, 2001; Brandt et al., 2005; Rice et al., 2011). This allows for better oncolytic virus replication in cancer cells and spread through the tumor tissue.

Alternatively, VACV recombinants expressing herpesvirus thymidine kinase (tk) are constructed (Panicali & Paoletti, 1982). This is a desirable feature for an oncolytic VACV because VACV replication is inhibited by the anti-herpetic antiviral drugs acyclovir and ganciclovir and derivatives thereof in cells expressing the HSV tk gene (Darby et al., 1980). This embodiment capitalizes on the capacity of herpesvirus tk enzymes (HSV1, HSV2, VZV and EBV) to specifically activate these anti-viral prodrugs, a particularly useful feature given the safety spectrum of acyclovir and derivatives and the paucity of anti-viral agents with activity against Poxviruses. Such a recombinant VACV expressing a herpesvirus tk gene allows VACV oncolytic virus therapies to be easily controlled with effective, safe anti-virals that are dependent upon herpesvirus tk activity.

Those skilled in the art can construct a recombinant Poxvirus deficient in either D9, D10 or both decapping orthologs expressing the tk derived from HSV1, HSV2, VZV, or EBV or any other herpesvirus by homologous recombination techniques. In a preferred embodiment, Poxviruses deficient in D9, D10 or both D9 and D10 are engineered to express a herpesvirus tk gene. The 5'-end of the herpesvirus tk gene is first fused to a VACV promoter (for example, the VACV tk gene promoter or the VACV 7.5K promoter), and the 3'-end of the tk gene to a VACV transcriptional terminator sequence element. By selectively cloning appropriate VACV flanking sequences upstream and downstream of the herpesvirus tk gene fused to a VACV promoter in a targeting plasmid vector backbone, the herpesvirus tk gene is integrated and ectopically expressed at nearly any site in the VACV genome as long as it does not disrupt an essential VACV function required for productive virus growth. For example, the herpesvirus tk gene modified with a VACV promoter and transcriptional terminator sequence elements replaces or inactivates the endogenous VACV tk gene. Alternatively, the herpesvirus tk gene is modified with a VACV promoter and transcriptional terminator and inserted as a transgene elsewhere in the viral genome (i.e. a location other than within the VACV tk gene) at a site which is not essential for replication in cultured cells (including but not limited to the VACV ribonucleotide reductase gene, the D9 decapping enzyme, or the D10 decapping enzyme), replacing or rendering the gene at the insertion site non-functional by insertion of the herpesvirus tk gene fused to the VACV promoter and transcriptional terminator.

To construct the VACV recombinant, VACV viral DNA prepared from a D9, D10, or D9/D10 doubly deficient strain is co-transfected with the aforementioned herpesvirus tk targeting plasmid into permissive cells. To simplify the identification of recombinants, the starting decapping-deficient strain is first modified by inserting a reporter gene (such as eGFP, RFP, YFP, β-galactosidease or β-glucuronidase) at the desired site of herpesvirus tk insertion. For example, the D9 and/or D10 genes are replaced with eGFP. Next, homologous recombination is used to replace the eGFP reporter gene with the herpesvirus tk gene fused to a VACV promoter and transcription terminator element. This results in an eGFP-negative recombinant VACV where the D9 and/or D10 genes have been replaced by the herpesvirus gene which is expressed from a VACV promoter. Alternatively, the VACV tk gene is first replaced with an eGFP reporter by homologous recombination as described above. Next, homologous recombination is used to screen for eGFP-negative viruses following transfection of the herpesvirus tk targeting plasmid. This results in a eGFP-negative recombinant VACV where the endogenous VACV tk gene has been replaced by the herpesvirus tk gene which is expressed from a VACV promoter. Restriction digestion, Southern blotting, and PCR are used to verify the physical structure of recombinant VACV genomes.

The VACV recombinants expressing herpesvirus tk are sensitive to anti-viral drugs including acyclovir (ACV) and ganciclovir (GCV) and derivatives thereof, whereas VACV that do not express herpesvirus tk are insensitive to ACV, GCV and derivatives thereof. The productive growth of VACV expressing herpesvirus tk is inhibited by ACV and GCV and derivatives thereof whereas VACV unable to express herpesvirus tk is unaffected by the drugs. The decapping deficient poxviruses like VACV expressing herpesvirus TK have a considerable safety advantage, enabling antiviral therapy of oncolytic VACV with ACV, GCV and derivatives should it become necessary to control the oncolytic VACV with safe, efficacious antiviral drugs. For example, should a patient being treated with oncolytic VACV expressing herpesvirus tk become immunosuppressed, or the OV therapy proceeds for some reason in an uncontrolled manner or spread to other organ systems, it is possible to effectively halt the OV therapy by administering ACV, GCV or derivatives by IV or oral administration.

Example 13: Reduction in Tumor Volume is Associated with an Increase in Infectious Virus Titer The oncolytic Poxviridae decapping deficient mutant viruses of the present invention are administered one or more times to an individual with cancer, for example hepatocellular carcinoma, by imaging guided intratumoral injection or iv ($1\times10^5$-$1\times10^9$ pfu/kg). Once in the liver, the oncolytic virus of the present invention preferentially accumulates proteins and replicates within tumor cells, effectively spreading through the tumor mass. Thus, in tumorigenic cells, sustained virus replication results in increasing amounts of virus available to continue spreading through the tumor.

Reduction in tumor volume is associated with an increase in infectious virus titer, indicating virus replication within the tumor. This not only results in cytolytic destruction of the tumor, but allows for the release of tumor associated antigens (TAAs) from the tumor. The resulting TAAs in turn are presented to the immune system by antigen presenting cells and assist in the development of host anti-tumor immune responses that synergize with oncolytic viruses, such as the virus of the present invention, to achieve a reduction in tumor volume locally and systemically (metastases). Even further synergy between the oncolytic viruses of the present invention is achieved by using therapeutic antibodies that function as immune checkpoint inhibitors (like anti-CTLA4, anti-PD1, and anti-PDL1).

The oncolytic Poxviridae decapping deficient mutant viruses of the present invention activate cell intrinsic host defenses like PKR and RNase L within non-tumorigenic cells, limiting viral protein accumulation, replication and spread in non-tumorigenic tissue. Because the oncolytic Poxviridae decapping deficient mutant viruses of the present invention preferentially replicate in tumorigenic tissue, compared to non-tumorigenic tissue, there will be little or minimal collateral damage caused by the virus to normal, non-tumorigenic tissue neighboring the tumor masses as the oncolytic Poxvirus does not replicate in a prolonged, sustainable manner in non-tumorigenic tissue. Treatment with the oncolytic Poxviridae decapping deficient mutant virus of the present invention will reduce the mass of tumors locally and systemically, leading to a lasting remission or possible cure, without the toxicity to normal cells associated with conventional radiotherapy and chemotherapy.

REFERENCES

Aloni, Y. (1972). Extensive symmetrical transcription of Simian Virus 40 DNA in virus-yielding cells. Proc Natl Acad Sci USA 69, 2404-2409.

Aloni, Y., and Locker, H. (1973). Symmetrical in vivo transcription of polyoma DNA and the separation of self-complementary viral and cell RNA. Virology 54, 495-505.

Arribas-Layton, M., Wu, D., Lykke-Andersen, J., and Song, H. (2013). Structural and functional control of the eukaryotic mRNA decapping machinery. Biochim Biophys Acta 1829, 580-589.

Beckham, C. J., and Parker, R. (2008). P bodies, stress granules, and viral life cycles. Cell Host Microbe 3, 206-212.

Baez M., Taussig R., Zazra J. J., Young J. F., Palese P., Reisfeld A., Skalka A. M. (1980). Complete nucleotide sequence of the influenza A/PR/8/34 virus NS gene and comparison with the NS genes of the A/Udom/72 and A/FPV/Rostock/34 strains. Nucleic Acids Res. 8:5845-5858.

Boone, R. F., Parr, R. P., and Moss, B. (1979). Intermolecular duplexes formed from polyadenylylated vaccinia virus RNA. J Virol 30, 365-374.

Braun, J. E., Truffault, V., Boland, A., Huntzinger, E., Chang, C. T., Haas, G., Weichenrieder, O., Coles, M., and Izaurralde, E. (2012). A direct interaction between DCP1 and XRN1 couples mRNA decapping to 5' exonucleolytic degradation. Nat Struct Mol Biol 19, 1324-1331.

Burgess, H. M. and Mohr, I. (2015). Cellular 5'-3' mRNA Exonuclease Xrn1 Controls Double-Stranded RNA Accumulation and Anti-Viral Responses. Cell Host & Microbe 17, 332-344.

Chang, H. W., Watson, J. C., and Jacobs, B. L. (1992). The E3L gene of vaccinia virus encodes an inhibitor of the interferon-induced, double-stranded RNA-dependent protein kinase. Proc Natl Acad Sci USA 89, 4825-4829.

Chapman, E. G., Costantino, D. A., Rabe, J. L., Moon, S. L., Wilusz, J., Nix, J. C., and Kieft, J. S. (2014). The structural basis of pathogenic subgenomic flavivirus RNA (sfRNA) production. Science 344, 307-310.

Chroboczek, J. 1., Bieber, F., Jacrot, B. (1992). The sequence of the genome of adenovirus type 5 and its comparison with the genome of adenovirus type 2. Virology, 186(1):280-5.

Chee, M. S., A. T. Bankier, S. Beck, R. Bohni, C. M. Brown, R. Cerny, T. Horsnell, C. A. I. Hutchison, T. Kouzarides, J. A. Martignetti, E. Preddie, S. C. Satchwell, P. Tomlinson, K. M. Weston, and B. G. Barrell. (1990). Analysis of the protein-coding content of the sequence of human cytomegalovirus strain AD169. Curr. Top. Microbiol. Immunol. 154:125-170.

Covarrubias, S., Gaglia, M. M., Kumar, G. R., Wong, W., Jackson, A. O., and Glaunsinger, B. A. (2011). Coordinated destruction of cellular messages in translation complexes by the gammaherpesvirus host shutoff factor and the mammalian exonuclease Xrn1. PLoS Pathog 7, e1002339.

Daugherty, M. D., and Malik, H. S. (2012). Rules of engagement: molecular insights from host-virus arms races. Annu Rev Genet 46, 677-700.

Darby G, Larder B A, Bastow K F, Field H J (1980). Sensitivity of viruses to phosphorylated 9-(2-hydorxymethyl) guanine revealed in TK-transformed cells. J. Gen. Virol. 48: 451-454.

Decker, C. J., and Parker, R. (1993). A turnover pathway for both stable and unstable mRNAs in yeast: evidence for a requirement for deadenylation. Genes Dev 7, 1632-1643.

Demaria, et al. (2005). Immune-mediated inhibition of metastases after treatment with local radiation and ctla-4 blockade in a mouse model of breast cancer Clin. Cancer Res., 11: 728-734.

Deurholt T, van Til N P, Chhatta A A, ten Bloemendaal L, Schwartlander R, Payne C, Plevris J N, Sauer I M, Chamuleau R A, Elferink R P, Seppen J, Hoekstra R. (2009). Novel immortalized human fetal liver cell line, cBAL111, has the potential to differentiate into functional hepatocytes. *BMC Biotechnol.* 9:89. doi: 10.1186/1472-6750-9-89.

Dougherty, J. D., White, J. P., and Lloyd, R. E. (2011). Poliovirus-mediated disruption of cytoplasmic processing bodies. J Virol 85, 64-75.

Elgadi, M. M., Hayes, C. E., and Smiley, J. R. (1999). The herpes simplex virus vhs protein induces endoribonucleolytic cleavage of target RNAs in cell extracts. J Virol 73, 7153-7164.

Everly, D. N., Jr., Feng, P., Mian, I. S., and Read, G. S. (2002). mRNA degradation by the virion host shutoff (Vhs) protein of herpes simplex virus: genetic and biochemical evidence that Vhs is a nuclease. J Virol 76, 8560-8571.

Gaglia, M. M., Covarrubias, S., Wong, W., and Glaunsinger, B. A. (2012). A common strategy for host RNA degradation by divergent viruses. J Virol 86, 9527-9530.

Gaglia, M. M., and Glaunsinger, B. A. (2010). Viruses and the cellular RNA decay machinery. Wiley Interdiscip Rev RNA 1, 47-59.

Garneau, N. L., Wilusz, J., and Wilusz, C. J. (2007). The highways and byways of mRNA decay. Nat Rev Mol Cell Biol 8, 113-126.

Gershon, P. D., Ahn, B. Y., Garfield, M., and Moss, B. (1991). Poly(A) polymerase and a dissociable polyadenylation stimulatory factor encoded by vaccinia virus. Cell 66, 1269-1278.

Giantini, M., Seliger, L. S., Furuichi. Y, Shatkin, A. J. (1984) Reovirus type 3 genome segment S4: nucleotide sequence of the gene encoding a major virion surface protein. J Virol. December; 52(3):984-7.

Haralambieva, I. H., Oberg, A. L., Dhiman, N., Ovsyannikova, I. G., Kennedy, R. B., Grill, D. E., Jacobson, R. M., and Poland, G. A. (2012). High-dimensional gene expression profiling studies in high and low responders to primary smallpox vaccination. J Infect Dis 206, 1512-1520.

He, B., Gross, M., and Roizman, B. (1997). The gamma(1) 34.5 protein of herpes simplex virus 1 complexes with protein phosphatase 1 alpha to dephosphorylate the alpha subunit of the eukaryotic translation initiation factor 2 and preclude the shutoff of protein synthesis by double-stranded RNA-activated protein kinase. Proc Natl Acad Sci USA 94, 843-848.

Jacobs, B. L., and Langland, J. O. (1996). When two strands are better than one: the mediators and modulators of the cellular responses to double-stranded RNA. Virology 219, 339-349.

Jacquemont, B., and Roizman, B. (1975). RNA synthesis in cells infected with herpes simplex virus. X. Properties of viral symmetric transcripts and of double-stranded RNA prepared from them. J Virol 15, 707-713.

Jagger, B. W., Wise, H. M., Kash, J. C., Walters, K. A., Wills, N. M., Xiao, Y. L., Dunfee, R. L., Schwartzman, L. M., Ozinsky, A., Bell, G. L., et al. (2012). An overlapping protein-coding region in influenza A virus segment 3 modulates the host response. Science 337, 199-204.

Jinek, M., Coyle, S. M., and Doudna, J. A. (2011). Coupled 5' nucleotide recognition and processivity in Xrn1-mediated mRNA decay. Mol Cell 41, 600-608.

Jonas, S., and Izaurralde, E. (2013). The role of disordered protein regions in the assembly of decapping complexes and RNP granules. Genes Dev 27, 2628-2641.

Kamitani, W., Narayanan, K., Huang, C., Lokugamage, K., Ikegami, T., Ito, N., Kubo, H., and Makino, S. (2006). Severe acute respiratory syndrome coronavirus nsp1 protein suppresses host gene expression by promoting host mRNA degradation. Proc Natl Acad Sci USA 103, 12885-12890.

Katsafanas, G. C., and Moss, B. (2007). Colocalization of transcription and translation within cytoplasmic poxvirus factories coordinates viral expression and subjugates host functions. Cell Host Microbe 2, 221-228.

Kwong, A. D., and Frenkel, N. (1987). Herpes simplex virus-infected cells contain a function(s) that destabilizes both host and viral mRNAs. Proc Natl Acad Sci USA 84, 1926-1930.

Li, Y., Dai, J., Song, M., Fitzgerald-Bocarsly, P., and Kiledjian, M. (2012). Dcp2 decapping protein modulates mRNA stability of the critical interferon regulatory factor (IRF) IRF-7. Mol Cell Biol 32, 1164-1172.

Liu, S. W., Katsafanas, G. C., Liu, R., Wyatt, L. S. and Moss, B. (2015). Poxvirus Decapping Enzymes Enhance Virulence by Preventing the Accumulation of dsRNA and the Induction of Innate Antiviral Responses. Cell Host & Microbe 17, 320-331.

Liu, S. W., Wyatt, L. S., Orandle, M. S., Minai, M., and Moss, B. (2014). The D10 decapping enzyme of vaccinia virus contributes to decay of cellular and viral mRNAs and to virulence in mice. J Virol 88, 202-211.

Lucas, J. J., and Ginsberg, H. S. (1972). Identification of double-stranded virus-specific ribonucleic acid in KB cells infected with type 2 adenovirus. Biochem Biophys Res Commun 49, 39-44.

Maran, A., and Mathews, M. B. (1988). Characterization of the double-stranded RNA implicated in the inhibition of protein synthesis in cells infected with a mutant adenovirus defective for VA RNA. Virology 164, 106-113.

McCart J A, Bartlett D L, Moss B. (2007) Combined growth factor deleted and thymidine kinase deleted Vaccinia Virus Vector. U.S. Pat. No. 7,208,313 B2.

McGeoch, D. J., Dolan, A., Donald, S. & Rixon, F. J. (1985). Sequence determination and genetic content of the short unique region in the genome of herpes simplex virus type 1. Journal of Molecular Biology 181, 1-13.

Mohr, I., and Sonenberg, N. (2012). Host translation at the nexus of infection and immunity. Cell Host Microbe 12, 470-483.

Morgan, J. R., Cohen, L. K., and Roberts, B. E. (1984). Identification of the DNA sequences encoding the large subunit of the mRNA-capping enzyme of vaccinia virus. J Virol 52, 206-214.

Moss, B. (2013). Poxvirus DNA replication. Cold Spring Harb Perspect Biol 5.

Moss, B., Rosenblum, E. N., and Gershowitz, A. (1975). Characterization of a polyriboadenylate polymerase from vaccinia virions. J Biol Chem 250, 4722-4729.

Mulvey, M., Poppers, J., Sternberg, D., and Mohr, I. (2003). Regulation of eIF2alpha phosphorylation by different functions that act during discrete phases in the herpes simplex virus type 1 life cycle. J Virol 77, 10917-10928.

Nagarajan, V. K., Jones, C. I., Newbury, S. F., and Green, P. J. (2013). XRN 5'→3' exoribonucleases: structure, mechanisms and functions. Biochim Biophys Acta 1829, 590-603.

Nevins, J. R., and Joklik, W. K. (1977). Isolation and partial characterization of the poly(A) polymerases from HeLa cells infected with vaccinia virus. J Biol Chem 252, 6939-6947.

Niles, E. G., Lee-Chen, G. J., Shuman, S., Moss, B., and Broyles, S. S. (1989). Vaccinia virus gene D12L encodes the small subunit of the viral mRNA capping enzyme. Virology 172, 513-522.

Orban, T. I., and Izaurralde, E. (2005). Decay of mRNAs targeted by RISC requires XRN1, the Ski complex, and the exosome. Rna 11, 459-469.

Panicali, D, Paoletti E. (1982) Construction of poxviruses as cloning vectors: insertion of the thymidine kinase gene from herpes simplex virus into the DNA of infectious vaccinia virus. Proc. Natl. Acad. Sci. USA 79: 4927-4931.

Parker, R., and Song, H. (2004). The enzymes and control of eukaryotic mRNA turnover. Nat Struct Mol Biol 11, 121-127.

Parrish, S., and Moss, B. (2006). Characterization of a vaccinia virus mutant with a deletion of the D10R gene encoding a putative negative regulator of gene expression. J Virol 80, 553-561.

Parrish, S., and Moss, B. (2007). Characterization of a second vaccinia virus mRNA-decapping enzyme conserved in poxviruses. J Virol 81, 12973-12978.

Parrish, S., Resch, W., and Moss, B. (2007). Vaccinia virus D10 protein has mRNA decapping activity, providing a mechanism for control of host and viral gene expression. Proc Natl Acad Sci USA 104, 2139-2144.

Plotch, S. J., Bouloy, M., Ulmanen, I., and Krug, R. M. (1981). A unique cap(m7GpppXm)-dependent influenza virion endonuclease cleaves capped RNAs to generate the primers that initiate viral RNA transcription. Cell 23, 847-858.

Poole, T. L., and Stevens, A. (1997). Structural modifications of RNA influence the 5' exoribonucleolytic hydrolysis by XRN1 and HKE1 of *Saccharomyces cerevisiae*. Biochem Biophys Res Commun 235, 799-805.

Read, G. S. (2013). Virus-encoded endonucleases: expected and novel functions. Wiley Interdiscip Rev RNA 4, 693-708.

Read, G. S., and Frenkel, N. (1983). Herpes simplex virus mutants defective in the virion-associated shutoff of host polypeptide synthesis and exhibiting abnormal synthesis of alpha (immediate early) viral polypeptides. J Virol 46, 498-512.

Rivas, C., Gil, J., Melkova, Z., Esteban, M., and Diaz-Guerra, M. (1998). Vaccinia virus E3L protein is an inhibitor of the interferon (i.f.n.)-induced 2-5A synthetase enzyme. Virology 243, 406-414.

Sadler, A. J., and Williams, B. R. (2008). Interferon-inducible antiviral effectors. Nat Rev Immunol 8, 559-568.

Sciortino, M. T., Parisi, T., Siracusano, G., Mastino, A., Taddeo, B., and Roizman, B.

(2013). The virion host shutoff RNase plays a key role in blocking the activation of protein kinase R in cells infected with herpes simplex virus 1. J Virol 87, 3271-3276.

Seo, E. J., Liu, F., Kawagishi-Kobayashi, M., Ung, T. L., Cao, C., Dar, A. C., Sicheri, F., and Dever, T. E. (2008). Protein kinase PKR mutants resistant to the poxvirus pseudosubstrate K3L protein. Proc Natl Acad Sci USA 105, 16894-16899.

Shuman, S., Surks, M., Furneaux, H., and Hurwitz, J. (1980). Purification and characterization of a GTP-pyrophosphate exchange activity from vaccinia virions. Association of the GTP-pyrophosphate exchange activity with vaccinia mRNA guanylyltransferase. RNA (guanine-7-) methyltransferase complex (capping enzyme). J Biol Chem 255, 11588-11598.

Silva, P. A., Pereira, C. F., Dalebout, T. J., Spaan, W. J., and Bredenbeek, P. J. (2010). An RNA pseudoknot is required for production of yellow fever virus subgenomic RNA by the host nuclease XRN1. J Virol 84, 11395-11406.

Sivan, G., Martin, S. E., Myers, T. G., Buehler, E., Szymczyk, K. H., Ormanoglu, P., and Moss, B. (2013). Human genome-wide RNAi screen reveals a role for nuclear pore proteins in poxvirus morphogenesis. Proc Natl Acad Sci USA 110, 3519-3524.

Stoecklin, G., Mayo, T., and Anderson, P. (2006). ARE-mRNA degradation requires the 5'-3' decay pathway. EMBO Rep 7, 72-77.

Venkatesan, S., Gershowitz, A., and Moss, B. (1980). Modification of the 5' end of mRNA. Association of RNA triphosphatase with the RNA guanylyltransferase-RNA (guanine-7-)methyltransferase complex from vaccinia virus. J Biol Chem 255, 903-908.

Walsh, D., Arias, C., Perez, C., Halladin, D., Escandon, M., Ueda, T., Watanabe-Fukunaga, R., Fukunaga, R., and Mohr, I. (2008). Eukaryotic translation initiation factor 4F architectural alterations accompany translation initiation factor redistribution in poxvirus-infected cells. Mol Cell Biol 28, 2648-2658.

Walsh, D., Mathews, M. B., and Mohr, I. (2013). Tinkering with translation: protein synthesis in virus-infected cells. Cold Spring Harb Perspect Biol 5, a012351.

Walsh, D., and Mohr, I. (2011). Viral subversion of the host protein synthesis machinery. Nat Rev Microbiol 9, 860-875.

Warren, R. D., Cotter, C. A., and Moss, B. (2012). Reverse genetics analysis of poxvirus intermediate transcription factors. J Virol 86, 9514-9519.

Weber, F., Wagner, V., Rasmussen, S. B., Hartmann, R., and Paludan, S. R. (2006). Double-stranded RNA is produced by positive-strand RNA viruses and DNA viruses but not in detectable amounts by negative-strand RNA viruses. J Virol 80, 5059-5064.

Laidlaw, S. M., and M. A. Skinner. 2004. Comparison of the genome sequence of FP9, an attenuated, tissue culture-adapted European strain of fowlpox virus, with those of virulent American and European viruses. J. Gen. Virol. 85:3 05-322.

Parrish, S, Moss B. (2007). Characterization of a second vaccinia virus mRNA-decapping enzyme conserved in poxviruses. J Virol. 81:12973-12978.

Parrish, S., W. Resch, and B. Moss. (2007). Vaccinia virus D10 protein has mRNA decapping activity, providing a mechanism for control of host and viral gene expression. Proc. Natl. Acad. Sci. USA 104: 2139-2144.

Koonin E V (1993) A highly conserved sequence motif defining the family of MutT-related proteins from eubacteria, eukaryotes and Viruses. Nucleic Acids Res 21:4847.

Bessman M J, Frick D N, O'Handley S F (1996) The MutT Proteins or "Nudix" Hydrolases, a Family of Versatile, Widely Distributed, "Housecleaning" Enzymes J Biol Chem 271:25059-25062.

Dunckley, T. and Parker, R. 1999. The DCP2 protein is required for mRNA decapping in Saccharomyces cerevisiae and contains a functional MutT motif EMBO J. 18: 5411-5422.

Wang Z, Jiao X, Carr-Schmid A, Kiledjian M (2002) The hDcp2 protein is a mammalian mRNA decapping enzyme. Proc Natl Acad Sci USA 99:12663-12668.

Van Dijk E, Cougot N, Meyer S, Babajko S, Wahle E, Seraphin B (2002) Human Dcp2: a catalytically active mRNA decapping enzyme located in specific cytoplasmic structures. EMBO J 21:6915-6924.

Cohen L S, Mikhli C, Jiao X, Kiledjian M, Kunkel G, Davis R E (2005) Dcp2 Decaps m2,2,7GpppN-Capped RNAs, and Its Activity Is Sequence and Context Dependent. Mol Cell Biol 25:8779-8791.

Kim M. (2015) Replicating poxviruses for human cancer therapy. J. Microbiology 53: 209-218.

Rerks-Ngarm, S. et al. (2009) Vaccination with ALVAC and AIDSVAX to prevent HIV-1 infection in Thailand. N. Engl. J. Med. 361, 2209-2220.

Laidlaw, S. M., and M. A. Skinner. 2004. Comparison of the genome sequence of FP9, an attenuated, tissue culture-adapted European strain of fowlpox virus, with those of virulent American and European viruses. J. Gen. Virol. 85:3 05-322.

Parrish, S, Moss B. (2007). Characterization of a second vaccinia virus mRNA-decapping enzyme conserved in poxviruses. J. Virol. 81:12973-12978.

Parrish, S., W. Resch, and B. Moss. (2007). Vaccinia virus D10 protein has mRNA decapping activity, providing a mechanism for control of host and viral gene expression. Proc. Natl. Acad. Sci. USA 104: 2139-2144.

Koonin E V (1993) A highly conserved sequence motif defining the family of MutT-related proteins from eubacteria, eukaryotes and Viruses. Nucleic Acids Res 21:4847.

Bessman M J, Frick D N, O'Handley S F (1996) The MutT Proteins or "Nudix" Hydrolases, a Family of Versatile, Widely Distributed, "Housecleaning" Enzymes J Biol Chem 271:25059-25062.

Dunckley, T. and Parker, R. 1999. The DCP2 protein is required for mRNA decapping in Saccharomyces cerevisiae and contains a functional MutT motif EMBO J. 18: 411-5422.

Wang Z, Jiao X, Carr-Schmid A, Kiledjian M (2002) The hDcp2 protein is a mammalian mRNA decapping enzyme. Proc Natl Acad Sci USA 99:12663-12668.

Van Dijk E, Cougot N, Meyer S, Babajko S, Wahle E, Seraphin B (2002) Human Dcp2: a catalytically active mRNA decapping enzyme located in specific cytoplasmic structures. EMBO J 21:6915-6924.

Cohen L S, Mikhli C, Jiao X, Kiledjian M, Kunkel G, Davis R E (2005) Dcp2 Decaps m2,2,7GpppN-Capped RNAs, and Its Activity Is Sequence and Context Dependent. Mol Cell Biol 25:8779-8791.

Kim M. (2015) Replicating poxviruses for human cancer therapy. J. Microbiology 53: 209-218.

Rerks-Ngarm, S. et al. Vaccination with ALVAC and AIDSVAX to prevent HIV-1 infection in Thailand. N. Engl. J. Med. 361, 2209-2220 (2009).

Burgess H M, Mohr I., (2015) Cellular 5'-3' mRNA exonuclease Xrn1 controls double-stranded RNA accumulation and anti-viral responses. Cell Host Microbe. 11; 17(3): 332-44.

Walsh D, Mohr I. (2011), Viral subversion of the host protein synthesis machinery, Nat Rev Microbiol. 2011 Oct. 17; 9(12):860-75.

Mohr I. (2005). To replicate or not to replicate: achieving selective oncolytic virus replication in cancer cells through translational control. Oncogene 24(52):7697-709.

Taneja S, MacGregor J, Markus S, Ha S, Mohr I. (2001), Enhanced antitumor efficacy of a herpes simplex virus mutant isolated by genetic selection in cancer cells. Proc Natl Acad Sci USA.; 98(15):8804-8.

Mulvey M, Poppers J, Ladd A, Mohr I. (1998), A herpesvirus ribosome-associated, RNA-binding protein confers a growth advantage upon mutants deficient in a GADD34-related function. J Virol. 73(4):3375-85.

Mohr I, Gluzman Y, EMBO J. 1996 Sep. 2; 15(17):4759-66. A herpesvirus genetic element which affects translation in the absence of the viral GADD34 function.

Walsh D, Mohr I. Genes Dev. 2004 Mar. 15; 18(6):660-72. Phosphorylation of eIF4E by Mnk-1 enhances HSV-1 translation and replication in quiescent cells.

Walsh D, Arias C, Perez C, Halladin D, Escandon M, Ueda T, Watanabe-Fukunaga R,

Fukunaga R, Mohr I., Mol Cell Biol. 2008 April; 28(8): 2648-58. Eukaryotic translation initiation factor 4F architectural alterations accompany translation initiation factor redistribution in poxvirus-infected cells.

Mohr, I. and M. Mulvey. U.S. Pat. No. 7,731,952. Oncolytic HSV-1 strains engineered to counter the innate host response.

Laidlaw, S. M., and M. A. Skinner. 2004. Comparison of the genome sequence of FP9, an attenuated, tissue culture-adapted European strain of fowlpox virus, with those of virulent American and European viruses. J. Gen. Virol. 85:3 05-322.

Parrish, S, Moss B. (2007). Characterization of a second vaccinia virus mRNA-decapping enzyme conserved in poxviruses. J. Virol. 81:12973-12978.

Parrish, S., W. Resch, and B. Moss. (2007). Vaccinia virus D10 protein has mRNA decapping activity, providing a mechanism for control of host and viral gene expression. Proc. Natl. Acad. Sci. USA 104: 2139-2144.

Koonin E V (1993) A highly conserved sequence motif defining the family of MutT-related proteins from eubacteria, eukaryotes and Viruses. Nucleic Acids Res 21:4847.

Bessman M J, Frick D N, O'Handley S F (1996) The MutT Proteins or "Nudix" Hydrolases, a Family of Versatile, Widely Distributed, "Housecleaning" Enzymes J Biol Chem 271:25059-25062.

Dunckley, T. and Parker, R. 1999. The DCP2 protein is required for mRNA decapping in Saccharomyces cerevisiae and contains a functional MutT motif EMBO J. 18: 5411-5422.

Wang Z, Jiao X, Carr-Schmid A, Kiledjian M (2002) The hDcp2 protein is a mammalian mRNA decapping enzyme. Proc Natl Acad Sci USA 99:12663-12668.

Van Dijk E, Cougot N, Meyer S, Babajko S, Wahle E, Seraphin B (2002) Human Dcp2: a catalytically active mRNA decapping enzyme located in specific cytoplasmic structures. EMBO J 21:6915-6924.

Cohen L S, Mikhli C, Jiao X, Kiledjian M, Kunkel G, Davis R E (2005) Dcp2 Decaps m2,2,7GpppN-Capped RNAs, and Its Activity Is Sequence and Context Dependent. Mol Cell Biol 25:8779-8791.

Kim M. (2015) Replicating poxviruses for human cancer therapy. J. Microbiology 53: 209-218.

Rerks-Ngarm, S. et al. (2009) Vaccination with ALVAC and AIDSVAX to prevent HIV-1 infection in Thailand. N. Engl. J. Med. 361, 2209-2220.

The present invention is not to be limited in scope by the specific embodiments described herein. Indeed, various modifications of the invention in addition to those described herein will be apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entirety for all uses.

What is claimed is:

1. A method for treating a subject suffering from a tumor comprising administering to a subject in need of such treatment a therapeutically effective amount of a vaccinia virus (VacV) decapping deficient mutant virus.

2. The method of claim 1, wherein the VacV is selected from the group consisting of D9, D10, and D9/10 doubly deficient mutants.

3. The method of claim 1, wherein the effective amount comprises between about $10^4$ pfu per kg body weight to about $3 \times 10^7$ pfu per kg body weight of the subject.

4. The method of claim 1, wherein the subject is a human.

5. The method of claim 1, wherein the VacV decapping deficient mutant virus is parenterally administered in a pharmaceutical formulation.

6. The method of claim 5, wherein the pharmaceutical formulation comprises a pharmaceutically acceptable carrier or diluent.

7. The method of claim 6, further comprising administering a checkpoint inhibitor.

8. The method of claim 7, which comprises co-administering the checkpoint inhibitor with the pharmaceutical formulation.

9. The method of claim 7, which comprises administering the checkpoint inhibitor separately from the pharmaceutical formulation.

10. The method of claim 9, further comprising treating said subject with an anti-cancer therapy selected from the group consisting of chemotherapy, radiation therapy, thermotherapy and transarterial chemoembolization (TACE).

11. The method of claim 2, wherein the VacV is created from a VacV selected from the group consisting of VacV strains Western Reserve (ATCC VR-1354), NYCBofH-Wyeth-(ATCC VR-1536), Modified Vaccinia Virus Ankara (ATCC VR-1566) and Lister (ATCC VR-1549).

12. The method of claim 1, wherein said VacV decapping deficient mutant virus further comprises an immune stimulating cytokine selected from the group consisting of IL-1, IL-2, IL-3, IL-4, IL-5, IL-6, IL-7, IL-8, IL-9, IL-10, IL-11, IL-12, IL-13, IL-14, IL-15, IL-16, IL-17 and IL-18-IL-36.

13. The method of claim 1, wherein said VacV decapping deficient mutant virus further comprises a chemokine selected from the group consisting of CC chemokines, CXC chemokines, C chemokines, and $CX_3C$ chemokines.

14. The method of claim 1, wherein said VacV decapping deficient mutant virus comprises a PKR/Ribonuclease L inhibitor selected from the group consisting of Herpes Simplex virus Type 1 (HSV1) Us11, human cytomegalovirus (HCMV) TRS1, reovirus sigma 3, influenza virus NS1, vaccinia virus E3L or K3L genes.

15. A pharmaceutical formulation comprising a VacV decapping deficient mutant virus, an immune checkpoint inhibitor and a pharmaceutically acceptable carrier or diluent.

16. The pharmaceutical formulation of claim 15, wherein said immune checkpoint inhibitor comprises an antibody directed against a cellular protein selected from the group consisting of PD1, PDL1, CTLA4, Tim-3, BTLA, Lag-3 and Tigit.

17. The pharmaceutical formulation of claim 16, wherein the VacV is created from a VacV selected from the group consisting of strains Western Reserve (ATCC VR-1354), NYCBofH-Wyeth (ATCC VR-1536), Modified Vaccinia Virus Ankara (ATCC VR-1566) and Lister (ATCC VR-1549).

18. A method for reducing the tumor burden in a mammal which comprises administering to a subject in need of such treatment an effective amount of a vaccinia virus mutant deficient for one or more viral genes that encode decapping enzymes.

19. The method of claim 1, wherein said VacV decapping deficient mutant virus further comprises an immune stimulating cytokine selected from the group consisting of a TAP inhibitor and granulocyte macrophage colony stimulating factor (GM-CSF).

* * * * *

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: polypeptide with a nudix hydrolase or MuT motif
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa; with Xaa = U or A; with U = an aliphatic,
      hydrophobic residue
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: MISC_FEATURE
<222> LOCATION: (23)..(23)
<223> OTHER INFORMATION: Xaa; with Xaa = U = an aliphatic, hydrophobic
      residue

<400> SEQUENCE: 1
```

```
Gly Xaa Xaa Xaa Xaa Xaa Glu Xaa Xaa Xaa Xaa Xaa Xaa Arg Glu
1               5               10                  15

Xaa Xaa Glu Glu Xaa Gly Xaa
            20
```